US011702398B2

(12) United States Patent
Kusano et al.

(10) Patent No.: US 11,702,398 B2
(45) Date of Patent: Jul. 18, 2023

(54) PHOTORESPONSIVE LOW-MOLECULAR WEIGHT MATERIAL, ADHESIVE, TONER, AND IMAGE FORMING METHOD

(71) Applicant: KONICA MINOLTA, INC., Tokyo (JP)

(72) Inventors: Yukiko Kusano, Toyohashi (JP); Haruo Horiguchi, Koganei (JP); Kouji Sugama, Musashino (JP); Seijiro Takahashi, Kokubunji (JP); Toyoko Shibata, Tokyo (JP); Hirofumi Hayata, Fuchu (JP); Tomohiro Oshiyama, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/788,518

(22) Filed: Feb. 12, 2020

(65) Prior Publication Data
US 2020/0264530 A1    Aug. 20, 2020

(30) Foreign Application Priority Data

Feb. 14, 2019  (JP) ................. 2019-024903
Nov. 1, 2019   (JP) ................. 2019-200312

(51) Int. Cl.
| | |
|---|---|
| *C07D 333/28* | (2006.01) |
| *C07D 333/22* | (2006.01) |
| *C07D 207/335* | (2006.01) |
| *C07D 307/56* | (2006.01) |
| *C07D 333/36* | (2006.01) |
| *C07D 207/34* | (2006.01) |
| *C07D 233/64* | (2006.01) |
| *C07D 209/86* | (2006.01) |
| *C07D 409/12* | (2006.01) |
| *C07D 231/38* | (2006.01) |
| *C07D 403/12* | (2006.01) |
| *C07C 251/24* | (2006.01) |
| *C07D 307/52* | (2006.01) |
| *C07D 233/88* | (2006.01) |
| *C07D 231/12* | (2006.01) |
| *G03G 9/09* | (2006.01) |

(52) U.S. Cl.
CPC .......... *C07D 333/22* (2013.01); *C07C 251/24* (2013.01); *C07D 207/335* (2013.01); *C07D 207/34* (2013.01); *C07D 209/86* (2013.01); *C07D 231/12* (2013.01); *C07D 231/38* (2013.01); *C07D 233/64* (2013.01); *C07D 233/88* (2013.01); *C07D 307/52* (2013.01); *C07D 307/56* (2013.01); *C07D 333/28* (2013.01); *C07D 333/36* (2013.01); *C07D 403/12* (2013.01); *C07D 409/12* (2013.01); *G03G 9/0922* (2013.01)

(58) Field of Classification Search
CPC .................................................. C07D 333/28
See application file for complete search history.

(56) References Cited

U.S. PATENT DOCUMENTS

| | | | | |
|---|---|---|---|---|
| 3,859,440 | A | * | 1/1975 | Serban ................. C07D 307/52 514/438 |
| 4,064,142 | A | | 12/1977 | Stein et al. |
| 4,578,390 | A | * | 3/1986 | Jensen ................. C07D 333/38 514/255.06 |
| 6,451,728 | B1 | | 9/2002 | Matsui et al. |
| 2013/0066068 | A1 | | 3/2013 | Norikane et al. |

FOREIGN PATENT DOCUMENTS

| | | |
|---|---|---|
| CN | 1257081 A | 6/2000 |
| CN | 105218711 A | 1/2016 |
| CN | 106938976 A | 7/2017 |
| DE | 79025 A | 1/1971 |
| EP | 0779353 A2 | 6/1997 |
| EP | 1008595 A2 | 6/2000 |
| EP | 1623971 A1 | 2/2006 |
| EP | 3401377 A1 | 11/2018 |
| EP | 3428727 A1 | 1/2019 |
| FR | 2306988 A1 | 11/1976 |
| JP | 2011-256155 A | 12/2011 |
| JP | 2011-256291 A | 12/2011 |
| JP | 2014-201538 A | 10/2014 |

OTHER PUBLICATIONS

Palitis et al. (Latvijas PSR Zinatnu Akademijas Vestis, Kimijas Serija (1983), (6), 722-4). Abstarct. (Year: 1983).*
Mihovilovic et al. (Journal fuer Praktische Chemie (Weinheim, Germany) (2000), 342(6), 585-590). Abstarct.*
Vinsova et al. (Bioorganic & Medicinal Chemistry (2006), 14(17), 5850-5865). Abstarct.*
Pokhrel et al. (Journal of Electronic Materials (2011), 40(2), 149-156). Abstarct.*
Ryabukhin et al. (Molecular Diversity (2012), 16(4), 625-637). Abstract.*
Angert et al. (Zhurnal Prikladnoi Khimii (Sankt-Peterburg, Russian Federation) (1959), 32, 408-18). Abstarct.*
Profft et al. (Wissenschaftliche Zeitschrift der Technischen Hochschule fuer Chemie "Carl Schorlemmer" Leuna-Merseburg (1960), vol. Date 1959-1960, 2, 181-5). Abstract.*
Sone et al. (Nippon Kagaku Zasshi (1962), 83, 496-9). Abstract.*
Sone et al. (Bulletin of the Chemical Society of Japan (1963), 36(5), 618-20). Abstarct.*
Nabeshima et al. (Chemistry of Materials (1997), 9(6), 1480-1487). Abstarct.*

(Continued)

*Primary Examiner* — Bruck Kifle
(74) *Attorney, Agent, or Firm* — Lucas & Mercanti, LLP

(57) ABSTRACT

Disclosed is a compound containing a specific structure having an azomethine part, the compound being reversibly fluidized and non-fluidized by being irradiated with light.

10 Claims, 3 Drawing Sheets

(56) References Cited

OTHER PUBLICATIONS

Epo, Office Action for the corresponding European Patent Application No. 20156958.9, dated Mar. 17, 2021.
Bheeter Linus P., et al., "Cyclopentadienyl N-heterocyclic carbenenickel complexes as efficient pre-catalysts for the hydrosilylation of imines," Catalysis Science & Technology, vol. 3, No. 12, Jan. 1, 2013, p. 3111, UK, Retrieved from the Internet: https://pubs.rsc.org/en/content/articlepdf/2013/cy/c3cy00514c.
Siopa Filipa, et al., "Ruthenium-Catalyzed C—H Arylation and Alkenylation of Furfural Imines with Boronates," European Journal of Organic Chemistry, vol. 2018, No. 44, Aug. 10, 2018, pp. 6101-6106, Germany, Retrieved from the Internet: https://api.wiley.com/onlinelibrary/tdm/v1/articles/10.1002%2Fejoc.201800767.
JPO, Office Action for the corresponding Japanese Patent Application No. 2019-024903, dated Jun. 21, 2022, with English translation.
Yuki Nabeshima, et al., "Synthesis of Novel Liquid-Crystalline Thiophene Derivatives and Evaluation of Their Photoresponsive Behavior," Chemistry of Materials, 1997, vol. 9(6), pp. 1480-1487.
Zeitschrif fuer Naturforschung, Teil B Anorganische Chemie, Organische Chemie, 1985, vol. 40B(9), pp. 1199-1213 with English concise explanation.
RN 2218003-90-6, etc., Database Registry (STN)[Online], Apr. 24, 2018.
Alex N. Borque, et al., "Thiophene-Phenyl Azomethines with Varying Rotational Barriers—Model Compounds for Examining Imine Fluorescence Deactivation," Journal of Physical Chemistry, 2009, vol. 113 (45), pp. 19677-19685.
Office Action dated Feb. 28, 2023, for the corresponding Chinese patent application No. 202010094619.9, with English translation.

\* cited by examiner

BEFORE LIGHT IRRADIATION

AFTER LIGHT IRRADIATION

AFTER STOPPING OF LIGHT IRRADIATION

PHOTORESPONSIVE LOW-MOLECULAR WEIGHT MATERIAL, ADHESIVE, TONER, AND IMAGE FORMING METHOD

CROSS-REFERENCE TO RELATED APPLICATION

Japanese Patent Application No. 2019-024903 filed on Feb. 14, 2019, and Japanese Patent Application No. 2019-200312 filed on Nov. 1, 2019, including description, claims, drawings, and abstract the entire disclosure is incorporated herein by reference in its entirety.

BACKGROUND

1. Technical Field

The present invention relates to a photoresponsive low-molecular weight material, an adhesive, a toner, and an image forming method.

2. Description of Related Arts

As materials whose fluidity changes as a result of light irradiation, photoresponsive liquid crystal materials are known. For example, in Japanese Patent Application Laid-Open No. 2011-256155 (corresponding to US 2013/066068A1) and Japanese Patent Application Laid-Open No. 2011-256291, polymeric liquid crystal materials using azobenzene derivatives are suggested. These respond to light and cause a cis-trans isomerization reaction of the azobenzene part. It is considered that a change in the molecular structure caused thereby induces phase transition from a solid state to a fluid state. Furthermore, when the polymeric liquid crystal materials are irradiated with light again after changing the wavelength, heated, or left to stand at room temperature in the dark, a reverse reaction occurs, and the materials are solidified again.

SUMMARY

However, the azobenzene derivatives described in Japanese Patent application Laid-Open No. 2011-256155 (corresponding to US 2013/066068A1) and Japanese Patent Application Laid-Open No. 2011-256291 are all colored in yellow to orange, and there is a problem that desired colors cannot be reproduced when the azobenzene derivatives are applied to industrial products such as toners and adhesives. Furthermore, according to the investigation of the present inventors, it was also found that in regard to coloration in yellow to orange, although the color can be slightly adjusted by changing the substituents of the azobenzene derivatives, it is basically impossible to make the azobenzene derivatives colorless or to bring the compounds to a state close to colorlessness.

Thus, it is an object of the present invention to provide a compound that is reversibly fluidized and non-fluidized by irradiating with light and does not undergo noticeable coloration.

It is another object of the present invention to provide an industrial product such as a toner or an adhesive, which uses the above-described compound.

It is still another object of the present invention to provide an image forming method using the above-described toner.

The present inventors repeatedly conducted a thorough investigation in view of the problems described above. As a result, the inventors found that a photoresponsive compound that is reversibly fluidized and non-fluidized and does not undergo, when applied to a toner or an adhesive, noticeable coloration to the extent that will not affect the reproduction of a desired color, is realized by using a compound having an azomethine part, and thereby the problems described above are solved. Thus, the inventors finally completed the present invention.

Furthermore, the present inventors found that the problems described above are solved by using a compound having an azomethine part, in which the activation energy for the isomerization from a cis-form to a trans-form is in a predetermined range, and thus finally completed the present invention.

That is, a first embodiment of the present invention is achieved by a photoresponsive low-molecular weight material, an adhesive, a toner, and an image forming method as shown in the following items 1 to 16.

1. A compound represented by the following Chemical Formula 1, which is reversibly fluidized and non-fluidized by being irradiated with light:

[Chemical Formula 1]

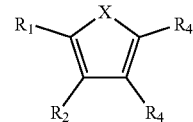

<Chemical Formula 1>

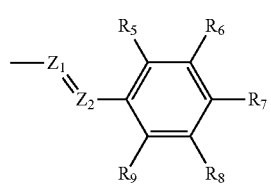

<Chemical Formula 2> wherein in the Chemical Formula 1,
X represents $NR_{10}$, O, or S;
$Z_1$ and $Z_2$ each independently represent N or CH, while $Z_1 \neq Z_2$;
$R_1$ and $R_2$ each independently represent a hydrogen atom, a halogen atom, an alkyl group, an alkoxy group, an acyl group, an alkoxycarbonyl group, a cyano group, a nitro group, or a hydroxy group;
$R_3$ and $R_4$ each independently represent a group represented by Chemical Formula 2, a hydrogen atom, a halogen atom, an alkyl group, an alkoxy group, an acyl group, an alkoxycarbonyl group, a cyano group, a nitro group, or a hydroxy group;
wherein either of $R_3$ and $R_4$ is a group represented by Chemical Formula 2; and
$R_{10}$ represents a hydrogen atom, a halogen atom, an alkyl group, an alkoxycarbonyl group, or a hydroxy group;
in the Chemical Formula 2,
$R_5$ to $R_9$ each independently represent a hydrogen atom, a halogen atom, an alkyl group, an alkoxy group, an acyl group, an alkoxycarbonyl group, a cyano group, a nitro group, or a hydroxy group; and
wherein at least one of $R_5$ to $R_9$ represents an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms.

2. The compound as described in the item 1, wherein at least one of $R_1$ to $R_4$ in the Chemical Formula 1 represents a halogen atom, a cyano group, a nitro group, a hydroxy group, an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms, and/or $R_{10}$ represents a halogen atom, a hydroxy group, an alkyl group having 1 to 18 carbon atoms, or an alkoxycarbonyl group having 2 to 19 carbon atoms.

3. The compound as described in the item 1 or 2, wherein the $R_7$ represents an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms.

4. The compound as described in any one of the items 1 to 3, wherein the $R_7$ represents an alkyl group having 4 to 12 carbon atoms, an alkoxy group having 4 to 12 carbon atoms, an acyl group having 5 to 13 carbon atoms, or an alkoxycarbonyl group having 5 to 13 carbon atoms.

5. The compound as described in any one of the items 1 to 4, wherein at least one of the $R_5$, $R_6$, $R_8$, and $R_9$ represents an alkyl group having 1 to 4 carbon atoms which may be branched, an alkoxy group having 1 to 4 carbon atoms which may be branched, or a halogen atom.

6. The compound as described in any one of the items 1 to 5, wherein the wavelength of irradiated light at the time when the compound is fluidized by being irradiated with light is 280 nm or more and 480 nm or less.

7. A toner containing the compound as described in any one of the items 1 to 6.

8. The toner as described in the item 7, further containing a binder resin.

9. The toner as described in the item 8, wherein the binder resin includes at least one selected from the group consisting of a styrene-acrylic resin and a polyester resin.

10. The toner as described in any one of the items 7 to 9, further containing a colorant.

11. The toner as described in any one of the items 7 to 10, further containing a release agent.

12. An image forming method, including forming a toner image formed from the toner as described in any one of the items 7 to 11 on a recording medium; and irradiating the toner image with light and thereby softening the toner image.

13. The image forming method as described in the item 12, wherein the wavelength of light at the time of irradiating the toner image with light and softening the toner image is 280 nm or more and 480 nm or less.

14. The image forming method as described in the item 12 or 13, further including pressing the toner image.

15. The image forming method as described in the item 14, wherein in the pressing, the toner image is further heated.

16. A photosensitive adhesive containing the compound as described in any one of the items 1 to 6.

A second embodiment of the present invention is achieved by a photoresponsive compound, an adhesive, a toner, and an image forming method as shown in the following items 17 to 40.

17. A photoresponsive compound represented by a following General Formula (1), the photoresponsive compound being fluidized by being irradiated with light and is reversibly non-fluidized:

[Chemical Formula 2]

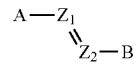

General Formula (1)

wherein in the General Formula (1), $Z_1$ and $Z_2$ each independently represent N or CH, while $Z_1 \neq Z_2$;

A and B each independently represent a substituted or unsubstituted aromatic hydrocarbon group or a substituted or unsubstituted aromatic heterocyclic group; and an activation energy Ea represented by a following Formula (1) is 60 kJ/mol or greater:

$$Ea(kJ/mol)=(\text{Total energy of } TS(kJ/mol))-(\text{Total energy of cis-form}(kJ/mol))\quad \text{Formula (1):}$$

wherein in the Formula (1), TS represents a transition state represented by General Formula (2); and the cis-form represents an isomer represented by General Formula (3):

[Chemical Formula 3]

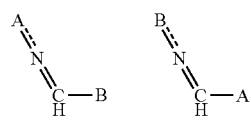

General Formula (2)

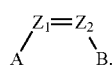

General Formula (3)

18. The compound as described in the item 17, wherein in the General Formula (1), A and B each independently represent a substituted or unsubstituted phenyl group or a substituted or unsubstituted aromatic heterocyclic group.

19. The compound as described in the item 18, wherein in the General Formula (1), A and B each independently represent a substituted or unsubstituted phenyl group, and at least one of A and B has at least one substituent selected among an alkyl group having 1 to 18 carbon atoms, an alkoxy group having 1 to 18 carbon atoms, and a dialkylamino group having 2 to 10 carbon atoms.

20. The compound as described in the item 19, wherein at least one of A and B has the substituent at a para-position with respect to $Z_1$ or $Z_2$.

21. The compound as described in the item 20, wherein both A and B have the substituent.

22. The compound as described in any one of the items 19 to 21, wherein at least one of A and B is a phenyl group unsubstituted at two ortho-positions and two meta-positions with respect to $Z_1$ or $Z_2$, or substituted with a group selected among an alkyl group having 1 to 4 carbon atoms, an alkoxy group having 1 to 4 carbon atoms, and a halogen atom.

23. The compound as described in the item 18, wherein one of A and B is a phenyl group substituted with at least one substituent selected among an alkyl group having 1 to 18 carbon atoms, an alkoxy group having 1 to 18 carbon atoms, and a dialkylamino group having 2 to 10 carbon atoms, and the other one is a substituted or unsubstituted aromatic heterocyclic group.

24. The compound as described in the item 23, wherein the phenyl group has the substituent at a para-position with respect to $Z_1$ or $Z_2$.

25. The compound as described in the item 24, wherein the aromatic heterocyclic group is unsubstituted, or the aromatic heterocyclic group is substituted with a halogen atom, a cyano group, a nitro group, an alkyl group having 1 to 18 carbon atoms, an alkoxy group having 1 to 18 carbon atoms, a dialkylamino group having 2 to 10 carbon atoms, an acyl group having 2 to 19 carbon atoms, or an alkoxycarbonyl group having 2 to 19 carbon atoms.

26. The compound as described in the item 18, wherein one of A and B is a substituted or unsubstituted phenyl group, and the other one is an aromatic heterocyclic group substituted with at least one substituent selected among an alkyl group having 1 to 18 carbon atoms, an alkoxy group having 1 to 18 carbon atoms, and a dialkylamino group having 2 to 10 carbon atoms.

27. The compound as described in the item 26, wherein the phenyl group is a phenyl group substituted with a halogen atom, a cyano group, a nitro group, an alkyl group having 1 to 18 carbon atoms, an alkoxy group having 1 to 18 carbon atoms, or a dialkylamino group having 2 to 10 carbon atoms.

28. The compound as described in the item 18, wherein in the General Formula (1), A and B each independently represent a substituted or unsubstituted aromatic heterocyclic group, and at least one of A and B has at least one substituent selected among an alkyl group having 1 to 18 carbon atoms, an alkoxy group having 1 to 18 carbon atoms, and a dialkylamino group having 2 to 10 carbon atoms.

29. The compound as described in the item 28, wherein one of A and B is an aromatic heterocyclic group having at least one substituent selected among an alkyl group having 1 to 18 carbon atoms, an alkoxy group having 1 to 18 carbon atoms, and a dialkylamino group having 2 to 10 carbon atoms, and the other one is an unsubstituted aromatic heterocyclic group or an aromatic heterocyclic group substituted with a halogen atom, a cyano group, a nitro group, an alkyl group having 1 to 18 carbon atoms, an alkoxy group having 1 to 18 carbon atoms, a dialkylamino group having 2 to 10 carbon atoms, an acyl group having 2 to 19 carbon atoms, or an alkoxycarbonyl group having 2 to 19 carbon atoms.

30. The compound as described in any one of the items 17 to 29, wherein the wavelength of the light is 280 nm or more and 480 nm or less.

31. A toner containing the compound as described in any one of the items 17 to 30.

32. The toner as described in the item 31, further containing a binder resin.

33. The toner as described in the item 31 or 32, wherein the binder resin includes at least one selected from the group consisting of a styrene-acrylic resin and a polyester resin.

34. The toner as described in any one of the items 31 to 33, further containing a colorant.

35. The toner as described in any one of the items 31 to 34, further containing a release agent.

36. An image forming method, including forming a toner image formed from the toner as described in any one of the items 31 to 35 on a recording medium; and irradiating the toner image with light and thereby softening the toner image.

37. The image forming method as described in the item 36, wherein the wavelength of the light is 280 nm or more and 480 nm or less.

38. The image forming method as described in the item 36 or 37, further including pressing the toner image.

39. The image forming method as described in the item 38, wherein in the pressing, the toner image is further heated.

40. A photoresponsive adhesive containing the compound as described in any one of the items 17 to 30.

BRIEF DESCRIPTION OF THE DRAWING

The advantages and features provided by one or more embodiments of the invention will become more fully understood from the detailed description given hereinbelow and the appended drawings which are given by way of illustration only, and thus are not intended as a definition of the limits of the present invention:

In FIG. 1, reference numeral 1 denotes a photoreceptor, reference numeral 2 denotes a charging device, reference numeral 3 denotes an exposure device, reference numeral 4 denotes a developing unit, reference numeral 5 denotes a transfer unit (transfer roller), reference numeral 7 denotes a paper conveyance system, reference numeral 8 denotes a cleaning unit, reference numeral 9 denotes a compression unit, reference numeral 10 denotes an image forming unit, reference numeral 11 denotes a paper feeder, reference numeral 12 denotes a conveyance roller, reference numeral 13 denotes a conveyance belt, reference numeral 14 denotes a paper ejection unit, reference numeral 15 denotes a manual paper feeder, reference numeral 16 denotes a tray, reference numeral 17 denotes a thermometer/hygrometer, reference numeral 20 denotes an image processing unit, reference numeral 24 denotes a paper inverting unit, reference numeral 40 denotes an irradiation unit, reference numeral 71 denotes an image reading apparatus, reference numeral 72 denotes an automatic document feeder, reference numeral 85 denotes a blade, reference numeral 90 denotes a control unit, reference numerals 91 and 92 denote a pressing member, reference numeral 100 denotes an image forming apparatus, reference numeral d denotes a document and reference numeral S denotes a recording paper, respectively;

In FIG. 2, reference numeral 1 denotes a photoreceptor, reference numeral 2 denotes a charging device, reference numeral 3 denotes an exposure device, reference numeral 4 denotes a developing unit, reference numeral 5 denotes a transfer unit (transfer roller), reference numeral 8 denotes a cleaning unit, reference numeral 9 denotes a compression unit, reference numeral 10 denotes an image forming unit, reference numeral 13 denotes a conveyance belt, reference numeral 40 denotes an irradiation unit, reference numeral 85 denotes a blade, and reference numerals 91 and 92 denote a pressing member, respectively;

FIG. 3A is a diagram showing a polarizing microscopic photograph of observing the state before light irradiation (solid before phase transition, non-fluid state). FIG. 3B is a diagram showing a polarizing microscopic photograph of observing a change in the state after light irradiation (softening caused by photo-induced phase transition, fluidized state). FIG. 3C is a diagram showing a polarizing microscopic photograph of observing a change in the state after stopping of light irradiation (re-solidification caused by a reverse reaction, non-fluidized state)

DETAILED DESCRIPTION OF EMBODIMENTS

Figure 1:
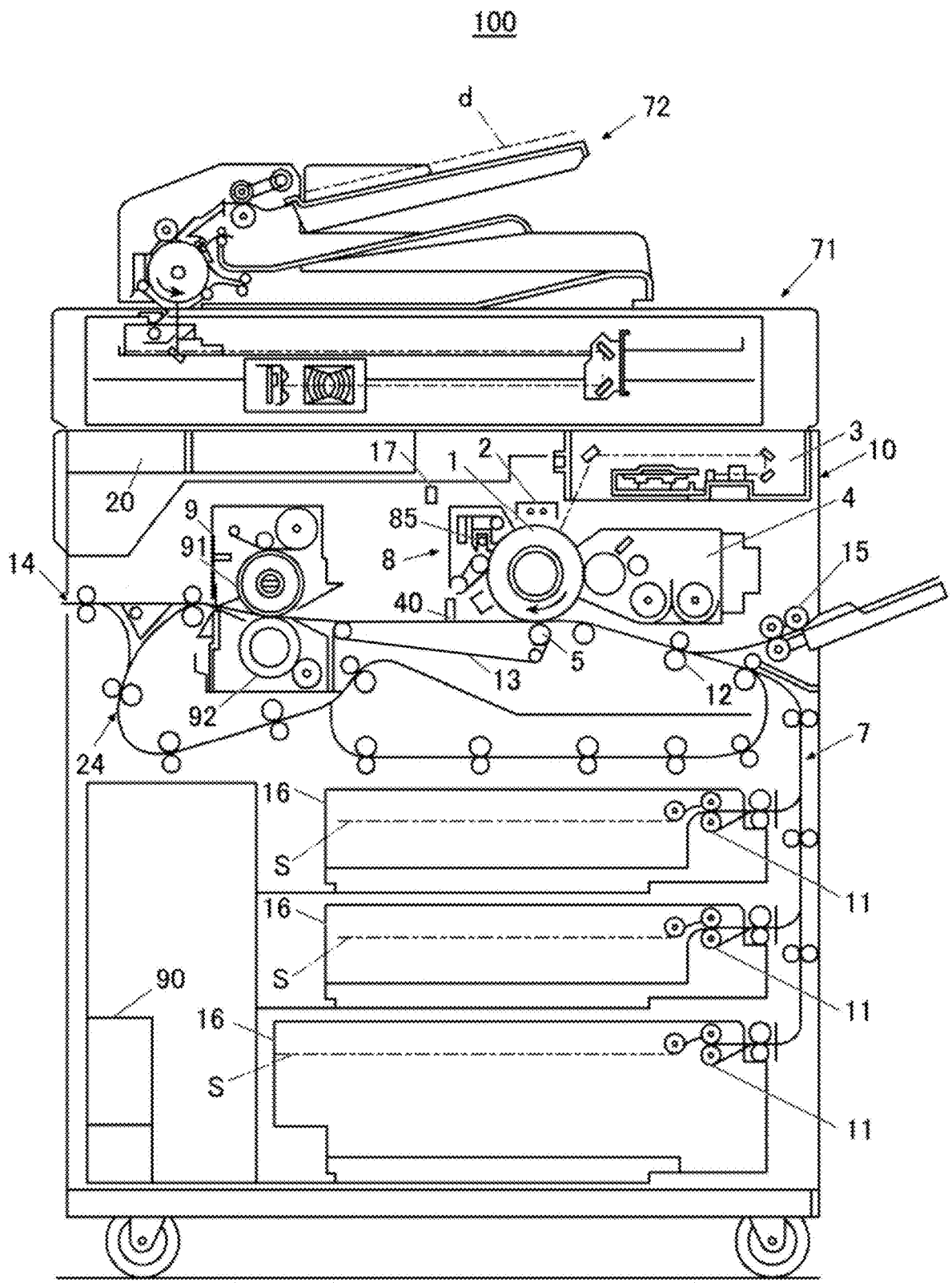
FIG. 1 is an outline configuration diagram illustrating an image forming apparatus used in an image forming method according to an embodiment of the present invention.

Hereinafter, one or more embodiments of the present invention will be described with reference to the drawings. However, the scope of the invention is not limited to the disclosed embodiments.

Meanwhile, according to the present specification, unless particularly stated otherwise, operations and measurement of physical properties and the like are carried out under the conditions of room temperature (20° C. to 25° C.)/relative humidity 40% to 50% RH.

First Embodiment

A first embodiment of the present invention is a compound represented by the following Chemical Formula 1, which is reversibly fluidized and non-fluidized by being irradiated with light.

[Chemical Formula 4]

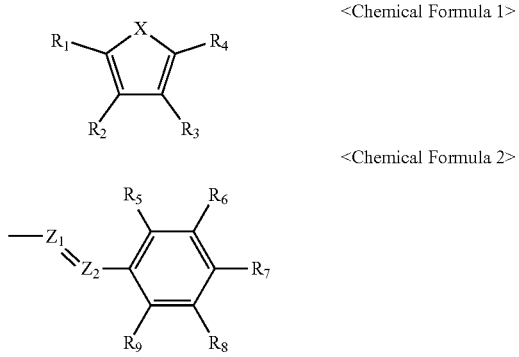

<Chemical Formula 1>

<Chemical Formula 2>

In the Chemical Formula 1,
X represents $NR_{10}$, O, or S;
$Z_1$ and $Z_2$ each independently represent N or CH, while $Z_1 \neq Z_2$;
$R_1$ and $R_2$ each independently represent a hydrogen atom, a halogen atom, an alkyl group, an alkoxy group, an acyl group, an alkoxycarbonyl group, a cyano group, a nitro group, or a hydroxy group;
$R_3$ and $R_4$ each independently represent a group represented by the Chemical Formula 2, a hydrogen atom, a halogen atom, an alkyl group, an alkoxy group, an acyl group, an alkoxycarbonyl group, a cyano group, a nitro group, or a hydroxy group;
wherein either of $R_3$ and $R_4$ represents a group represented by the Chemical Formula 2;
$R_{10}$ represents a hydrogen atom, a halogen atom, an alkyl group, an alkoxycarbonyl group, or a hydroxy group; and
in the Chemical Formula 2, $R_5$ to $R_9$ each independently represent a hydrogen atom, a halogen atom, an alkyl group, an alkoxy group, an acyl group, an alkoxycarbonyl group, a cyano group, a nitro group, or a hydroxy group; and wherein at least one of $R_5$ to $R_9$ represents an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms.

By using such a compound having an azomethine part represented by the Chemical Formula 1, a photoresponsive compound that is reversibly fluidized and non-fluidized by being irradiated with light and does not undergo coloration to the extent that will not affect the reproduction of a desired color when applied to a toner or an adhesive, can be realized.

That is, according to the first embodiment of the present invention, a compound that is reversibly fluidized and non-fluidized by being irradiated with light and does not undergo noticeable coloration, can be provided.

Furthermore, according to the first embodiment of the present invention, a toner containing the above-described compound, in which the rate of softening caused by light irradiation and the fixability of an image are excellent, and an image forming method of using this toner can be provided.

Furthermore, according to the first embodiment of the present invention, a photosensitive adhesive containing the above-described compound, in which the adhesiveness caused by light irradiation is excellent, can be provided.

The details of why the above-described effects are obtained by the compound of the present invention are not clearly known; however, a mechanism such as described below can be considered. Meanwhile, the following mechanism is based on speculation, and the present invention is not to be limited to the mechanism described below. In the following description, a compound represented by the Chemical Formula 1 will also be referred to as "compound having an azomethine part".

An azobenzene compound is known to be a material that absorbs light and is softened from a solid state (photo-induced phase transition), and that photo-induced phase transition is considered to occur as the crystal structure is destroyed by cis-trans isomerization. In the azobenzene compounds described in Japanese Patent Application Laid-Open No. 2011-256155 (corresponding to US 2013/066068A1) or Japanese Patent Application Laid-Open No. 2011-256291, phase change occurs concomitantly with an isomerization reaction caused by light irradiation; however, these compounds exhibit strong absorption originating from n-π* transition in the long wavelength region and are colored in orange. Therefore, there has been a problem that a desired color cannot be reproduced when the compounds are applied to industrial products.

In the present invention, providing a compound that is reversibly fluidized and non-fluidized by being irradiated with light and does not undergo noticeable coloration was realized by using a compound having an azomethine part. By introducing an azomethine part in place of azobenzene, the strong n-π* absorption in an azobenzene compound can be weakened, and therefore, a compound that does not undergo noticeable coloration can be realized.

Furthermore, it is speculated that in a compound that is reversibly fluidized and non-fluidized concomitantly with photo-isomerization, a regular structure is destroyed and undergoes a phase transition change as a non-fluid transform (E) is irradiated with light and is isomerized into a cis-form (Z), and thereby a reversible fluidization and non-fluidization phenomenon can be induced. Therefore, in order to induce a reversible fluidization and non-fluidization phenomenon, it is considered that many trans-forms (E) need to be isomerized into cis-forms (Z). However, generally, an azomethine compound is known to have a fast rate of isomerization from the Z-form to the E-form compared to an azobenzene compound, and in an azomethine compound having benzene introduced into both terminals, it was anticipated to be disadvantageous to induce a reversible fluidization and non-fluidization phenomenon.

In the present invention, it is thought that when a heterocyclic ring is introduced into an azomethine compound, the amount of the cis-form (Z) increases at the time of light irradiation, and fluidization concomitant with a photo-induced isomerization reaction can be induced. This is considered to be because the rate of isomerization from the Z-form to the E-form is decreased by introducing not benzene but a heterocyclic ring.

As described above, it is thought that photo-induced phase transition of an azomethine compound occurs as the crystal structure is destroyed by cis-trans isomerization, similarly to an azobenzene compound. Generally, since the intermolecular π-π interaction is strong, the photo-induced phase transition occurs only at the outermost surface of the crystal structure. On the other hand, the compound having an azomethine part of the present invention is such that at least one of the substituents of the benzene ring is an alkyl group, an alkoxy group, an acyl group, or an alkoxycarbonyl group. Since an alkyl group, an alkoxy group, an acyl group, or an alkoxycarbonyl group has thermal mobility, the compound having an azomethine part of the present invention forms a unique crystal structure in which within a periodic structure in which a π-π interaction is predominant, a structure that is isotropically disordered due to such thermal motion co-exists. Therefore, when a cis-trans isomerization reaction proceeds locally, and the π-π interaction of the azomethine part is reduced, isotropic fusion occurs in a chain reaction over the entire system. In addition, the compound having an azomethine part of the present invention is preferably such that at least one of the substituents of the heterocyclic ring is a halogen atom, a cyano group, a nitro group, a hydroxy group, an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms. When such a structure is adopted, production of lattice defects, exhibition of free volume, reduction of the π-π interaction, and the like that act advantageously on cis-trans isomerization occur. Therefore, it is considered that cis-trans isomerization can proceed more easily, and fluidization can be exhibited easily.

From the reasons described above, it is thought the compound having an azomethine part of the present invention is colorless and is able to induce a reversible fluidization and non-fluidization phenomenon in association with isomerization. Thus, by introducing a compound having an azomethine part into a toner, a toner that can be fixed by being irradiated with light and has high color reproducibility can be obtained.

The compound of the present invention varies from a non-fluid state to a fluid state as a result of light irradiation and further varies to a non-fluid state. The change from a fluid state to a non-fluid state does not necessarily require light irradiation.

Meanwhile, fluid state according to the present invention refers to a state in which the system is transformed without any external force or by a small external force.

Hereinafter, a preferred embodiment of the present invention will be described. Meanwhile, according to the present invention, the expression "X to Y" that represents a range means "X or more and Y or less". Furthermore, according to the present specification, unless particularly stated otherwise, operations and measurement of physical properties and the like are carried out under the conditions of room temperature (20° C. to 25° C.)/relative humidity 40% to 50% RH.

<Compound Having Azomethine Part>

The compound having an azomethine part of the present invention is a compound represented by the following Chemical Formula 1, which is reversibly fluidized and non-fluidized by being irradiated with light. In the present invention, it is speculated that by introducing not benzene but a heterocyclic ring represented by the following Chemical Formula 1 into the compound having an azomethine part, the rate of isomerization from the Z-form to the E-form was decreased, the amount of the cis-form (Z) increased at the time of light irradiation, and fluidization concomitantly with a photo-induced isomerization reaction could be induced.

[Chemical Formula 5]

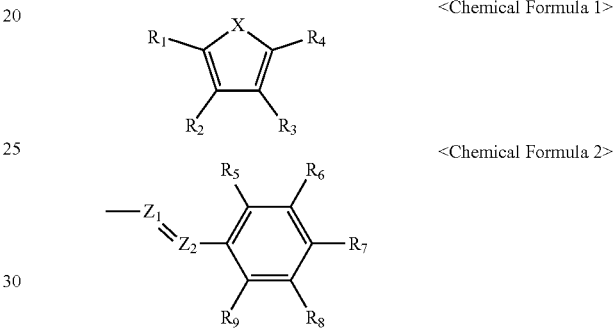

<Chemical Formula 1>

<Chemical Formula 2>

In the Chemical Formula 1, X represents $NR_{10}$, O, or S.

$Z_1$ and $Z_2$ each independently represent N or CH, while $Z_1 \neq Z_2$.

$R_1$ and $R_2$ each independently represent a hydrogen atom, a halogen atom, an alkyl group, an alkoxy group, an acyl group, an alkoxycarbonyl group, a cyano group, nitro group, or a hydroxy group.

$R_3$ and $R_4$ each independently represent a group represented by the Chemical Formula 2, a hydrogen atom, a halogen atom, an alkyl group, an alkoxy group, an acyl group, an alkoxycarbonyl group, a cyano group, a nitro group, or a hydroxy group.

At this time, either of $R_3$ and $R_4$ is a group represented by the Chemical Formula 2.

$R_{10}$ represents a hydrogen atom, a halogen atom, an alkyl group, an alkoxycarbonyl group, or a hydroxy group.

In the Chemical Formula 2, $R_5$ to $R_9$ each independently represent a hydrogen atom, a halogen atom, an alkyl group, an alkoxy group, an acyl group, an alkoxycarbonyl group, a cyano group, a nitro group, or a hydroxy group.

At this time, at least one of $R_5$ to $R_9$ represents an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms. As such, the compound having an azomethine part of the present invention is such that at least one of the substituents of the benzene ring of the Chemical Formula 2 is an alkyl group, an alkoxy group, an acyl group, or an alkoxycarbonyl group. Since an alkyl group, an alkoxy group, an acyl group, and an alkoxycarbonyl group have thermal mobility, the compound having an azomethine part of the present invention forms a unique crystal structure in which within a periodic structure in which a π-π interaction is predominant, a structure that is isotropically disordered due to such thermal motion co-exists. Therefore, when a cis-trans isomerization reaction proceeds locally, and the π-π interaction of the azomethine part is reduced, an effect of causing isotropic fusion in a chain reaction over the entire system can be provided.

In the present invention, it is preferable that at least one $R_1$ to $R_4$ in the Chemical Formula 1 represents a halogen atom, a cyano group, a nitro group, a hydroxy group, an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms, and/or $R_{10}$ represents a halogen atom, a hydroxy group, an alkyl group having 1 to 18 carbon atoms, or an alkoxycarbonyl group having 2 to 19 carbon atoms. Particularly, it is preferable that at least one of $R_1$ to $R_2$ and $R_{10}$, which are not adjacent to the group represented by the Chemical Formula 2, is any one of the substituents described above. By introducing the above-mentioned substituent of the heterocyclic ring, crystals become liable to collapse, photo-meltability is improved, and fixability is improved. Specifically, relative to Example 1-60, fixability of Examples 1-51 to 1-59 is improved. Among the above-mentioned substituents, an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms is preferred. An alkyl group having 1 to 12 carbon atoms, an alkoxy group having 1 to 12 carbon atoms, an acyl group having 2 to 13 carbon atoms, or an alkoxycarbonyl group having 2 to 13 carbon atoms is more preferred, and an alkyl group having 1 to 8 carbon atoms, an alkoxy group having 1 to 8 carbon atoms, an acyl group having 2 to 9 carbon atoms, or an alkoxycarbonyl group having 2 to 9 carbon atoms is even more preferred. As such, the compound having an azomethine part of the present invention is preferably such that at least one of the substituents of the heterocyclic ring of the Chemical Formula 1 (particularly, at least one of $R_1$ to $R_2$ and $R_{10}$, which are not adjacent to the group represented by the Chemical Formula 2) is a halogen atom, a cyano group, a nitro group, a hydroxy group, an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms (provided that $R_{10}$ is as described above). By adopting such a structure, production of lattice defects, exhibition of free volume, reduction of π-π interaction, and the like that act advantageously on cis-trans isomerization occur. Therefore, it is preferable from the viewpoint that cis-trans isomerization can proceed more easily, and fluidization can be exhibited easily. Furthermore, in the present invention, a case in which among $R_1$ to $R_4$ and $R_{10}$, which are substituents of the heterocyclic ring of the Chemical Formula 1, all other than the group represented by the Chemical Formula 2 are hydrogen atoms is preferable from the viewpoint that fluidization similar to that described above can be exhibited easily (see a compound 1-14 of Table 1-1 as well as Example 1-10 of Table 1-2 and Example 1-60 of Table 1-3 using this compound 1-14). This is because since the benzene ring (group represented by the Chemical Formula 2) has a long-chain substituent introduced therein, even in a case in which all of the substituents of the 5-membered ring (heterocyclic ring of the Chemical Formula 1) are hydrogen atoms, fluidization can be exhibited easily.

In the present invention, the $R_7$ is preferably an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms. An alkyl group having 1 to 12 carbon atoms, an alkoxy group having 1 to 12 carbon atoms, an acyl group having 2 to 13 carbon atoms, or an alkoxycarbonyl group having 2 to 13 carbon atoms is more preferred, and an alkyl group having 4 to 12 carbon atoms, an alkoxy group having 4 to 12 carbon atoms, an acyl group having 5 to 13 carbon atoms, or an alkoxycarbonyl group having 5 to 13 carbon atoms is even more preferred. As such, by introducing a long-chain substituent into the para-position of the benzene ring, crystals become liable to collapse, photo-meltability is improved, and fixability is improved. Specifically, fixability of Example 1-65 is improved compared to Example 1-90.

Furthermore, from the viewpoint that thermal motion is efficiently induced, regarding $R_{10}$ on the heterocyclic ring (5-membered ring) side of the Chemical Formula 1 or at least one of $R_1$ to $R_4$ that are not adjacent to the group represented by Chemical Formula 2 and $R_7$ of the 6-membered ring of the Chemical Formula 2, it is preferable that at least one is an alkyl group having 4 to 12 carbon atoms, an alkoxy group having 4 to 12 carbon atoms, an acyl group having 5 to 13 carbon atoms, or an alkoxycarbonyl group having 5 to 13 carbon atoms.

In the present invention, it is preferable that at least one of the $R_5$, $R_6$, $R_8$, and $R_9$ is an alkyl group having 1 to 4 carbon atoms which may have a branch, an alkoxy group having 1 to 4 carbon atoms which may have a branch, or a halogen atom, in order to induce production of lattice defects, exhibition of free volume, reduction of intermolecular π-π interaction, and the like, that act advantageously on cis-trans isomerization.

In the present invention, with regard to the heteroatom of the X, a sulfur atom (S) or a nitrogen atom (N) is preferred from the viewpoint that fixability is improved. Specifically, compared to Examples 1-94 to 1-96 in which the heteroatom of the X is an oxygen atom (O), fixability of Examples 1-51 to 1-93 and 1-97 to 1-99 in which the heteroatom is S or N is improved.

Examples of the alkyl group having 1 to 18 carbon atoms to be used for $R_1$ to $R_{10}$ are not particularly limited, and examples include linear alkyl groups such as a methyl group, an ethyl group, an n-propyl group, an n-butyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, and an n-hexadecyl group; and branched alkyl groups such as an isopropyl group, a sec-butyl group, an isobutyl group, a t-butyl group, a 1-methylpentyl group, a 4-methyl-2-pentyl group, a 3,3-dimethylbutyl group, a 2-ethylbutyl group, a 1-methylhexyl group, a t-octyl group, a 1-methylheptyl group, a 2-ethylhexyl group, a 2-propylpentyl group, a 2,2-dimethylheptyl group, a 2,6-dimethyl-4-heptyl group, a 3,5,5-trimethylhexyl group, a 1-methyldecyl group, and a 1-hexylheptyl group.

Examples of the alkoxy group having 1 to 18 carbon atoms to be used for $R_1$ to $R_{10}$ include linear alkoxy groups such as a methoxy group, an ethoxy group, an n-propoxy group, an n-butoxy group, an n-hexyloxy group, an n-heptyloxy group, an n-octyloxy group, an n-nonyloxy group, an n-decyloxy group, an n-undecyloxy group, an n-dodecyloxy group, an n-tridecyloxy group, an n-tetradecyloxy group, an n-pentadecyloxy group, and an n-hexadecyloxy group; and branched alkoxy groups such as a 1-methylpentyloxy group, a 4-methyl-2-pentyloxy group, a 3,3-dimethylbutyloxy group, a 2-ethylbutyloxy group, a 1-methylhexyloxy group, a t-octyloxy group, a 1-methylheptyloxy group, a 2-ethylhexyloxy group, a 2-propylpentyloxy group, a 2,2-dimethylheptyloxy group, a 2,6-dimethyl-4-heptyloxy group, a 3,5,5-trimethylhexyloxy group, a 1-methyldecyloxy group, and a 1-hexylheptyloxy group.

Examples of the acyl group having 2 to 19 carbon atoms to be used for $R_1$ to $R_{10}$ include saturated or unsaturated, linear or branched acyl groups, and examples include an acetyl group, a propanoyl group (propionyl group), a butanoyl group (butyryl group), an isobutanoyl group (isobutyryl group), a pentanoyl group (valeryl group), an isopentanoyl group (isovaleryl group), a sec-pentanoyl group (2-methylbutyryl group), a t-pentanoyl group (pivaloyl group), a hexanoyl group, a heptanoyl group, an octanoyl group, a t-octanoyl group (2,2-dimethylhexanoyl group), a 2-ethylhexanoyl group, a nonanoyl group, an isononanoyl group, a decanoyl group, an isodecanoyl group, an undecanoyl group, a lauroyl group, a myristoyl group, a palmitoyl group, a stearoyl group, a behenoyl group, an undecylenoyl group, an oleoyl group, and the like.

Examples of the alkoxycarbonyl group having 2 to 19 carbon atoms to be used for $R_1$ to $R_{10}$ include linear or branched alkoxycarbonyl groups, and examples include linear alkoxycarbonyl groups such as a methoxycarbonyl group, an ethoxycarbonyl group, an n-butoxycarbonyl group, an n-hexyloxycarbonyl group, an n-heptyloxycarbonyl group, an n-octyloxycarbonyl group, an n-nonyloxycarbonyl group, an n-decyloxycarbonyl group, an n-undecyloxycarbonyl group, an n-dodecyloxycarbonyl group, an n-tridecyloxycarbonyl group, an n-tetradecyloxycarbonyl group, an n-pentadecyloxycarbonyl group, and an n-hexadecyloxycarbonyl group; and branched alkoxycarbonyl groups such as a 1-methylpentyloxycarbonyl group, a 4-methyl-2-pentyloxycarbonyl group, a 3,3-dimethylbutyloxycarbonyl group, a 2-ethylbutyloxycarbonyl group, a 1-methylhexyloxycarbonyl group, a t-octyloxycarbonyl group, a 1-methylheptyloxycarbonyl group, a 2-ethylhexyloxycarbonyl group, a 2-propylpentyloxycarbonyl group, a 2,2-dimethylheptyloxycarbonyl group, a 2,6-dimethyl-4-heptyloxycarbonyl group, a 3,5,5-trimethylhexyloxycarbonyl group, a 1-methyldecyloxycarbonyl group, and a 1-hexylheptyloxycarbonyl group.

Regarding the compound having an azomethine part of the present invention, Compounds 1-1 to 1-74 formed as X, $Z_1$, $Z_2$, and $R_1$ to $R_{10}$ represented in the following Table 1-1 (Table 1-1-1, Table 1-1-2, and Table 1-1-3), and the like are selected as appropriate may be mentioned.

TABLE 1-1

| Compound | X | $Z_1$ | $Z_2$ | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|---|---|---|
| 1-1 | S | CH | N | $C_6H_{13}$ | H | H | Group of Formula 2 | H | $CH_3$ | $OC_6H_{13}$ | H | H | — |
| 1-2 | | | | $C_8H_{17}$ | H | H | Group of Formula 2 | H | $CH_3$ | $OC_6H_{13}$ | H | H | — |
| 1-3 | | | | $C_{12}H_{25}$ | H | H | Group of Formula 2 | H | $CH_3$ | $OC_6H_{13}$ | H | H | — |
| 1-4 | | | | $C_3H_7$ | H | H | Group of Formula 2 | H | $CH_3$ | $OC_6H_{13}$ | H | H | — |
| 1-5 | | | | $CH_3$ | H | H | Group of Formula 2 | H | $CH_3$ | $OC_6H_{13}$ | H | H | — |
| 1-6 | | | | $OC_6H_{13}$ | H | H | Group of Formula 2 | H | $CH_3$ | $OC_6H_{13}$ | H | H | — |
| 1-7 | | | | $COC_6H_{13}$ | H | H | Group of Formula 2 | H | $CH_3$ | $OC_6H_{13}$ | H | H | — |
| 1-8 | | | | $COOC_6H_{13}$ | H | H | Group of Formula 2 | H | $CH_3$ | $OC_6H_{13}$ | H | H | — |
| 1-9 | | | | Br | H | H | Group of Formula 2 | H | $CH_3$ | $OC_6H_{13}$ | H | H | — |
| 1-10 | | | | CN | H | H | Group of Formula 2 | H | $CH_3$ | $OC_6H_{13}$ | H | H | — |
| 1-11 | | | | $NO_2$ | H | H | Group of Formula 2 | H | $CH_3$ | $OC_6H_{13}$ | H | H | — |
| 1-12 | | | | $OCH_3$ | H | H | Group of Formula 2 | H | $CH_3$ | $OC_6H_{13}$ | H | H | — |
| 1-13 | | | | OH | H | H | Group of Formula 2 | H | $CH_3$ | $OC_6H_{13}$ | H | H | — |
| 1-14 | | | | H | H | H | Group of Formula 2 | H | $CH_3$ | $OC_6H_{13}$ | H | H | — |
| 1-15 | | | | $C_6H_{13}$ | $CH_3$ | H | Group of Formula 2 | H | $CH_3$ | $OC_6H_{13}$ | H | H | — |
| 1-16 | | | | $C_6H_{13}$ | H | $CH_3$ | Group of Formula 2 | H | $CH_3$ | $OC_6H_{13}$ | H | H | — |
| 1-17 | | | | $C_6H_{13}$ | H | H | Group of Formula 2 | $CH_3$ | H | $OC_6H_{13}$ | H | H | — |
| 1-18 | | | | $C_6H_{13}$ | H | H | Group of Formula 2 | H | $CH_3$ | $OC_6H_{13}$ | $CH_3$ | H | — |
| 1-19 | | | | $C_6H_{13}$ | H | H | Group of Formula 2 | H | H | $OC_6H_{13}$ | H | H | — |
| 1-20 | | | | $CH_3$ | H | H | Group of Formula 2 | H | H | $OC_6H_{13}$ | H | H | — |
| 1-21 | | | | Br | H | H | Group of Formula 2 | H | H | $OC_6H_{13}$ | H | H | — |
| 1-22 | | | | $OCH_3$ | H | H | Group of Formula 2 | H | H | $OC_6H_{13}$ | H | H | — |
| 1-23 | | | | H | H | H | Group of Formula 2 | H | H | $OC_6H_{13}$ | H | H | — |
| 1-24 | | | | $C_6H_{13}$ | H | H | Group of Formula 2 | H | Et | $OC_6H_{13}$ | H | H | — |
| 1-25 | | | | $C_6H_{13}$ | H | H | Group of Formula 2 | H | $OCH_3$ | $OC_6H_{13}$ | H | H | — |

TABLE 1-1-continued

| Compound | X | $Z_1$ | $Z_2$ | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|---|---|---|
| 1-26 | | | | $C_6H_{13}$ | H | H | Group of Formula 2 | H | Br | $OC_6H_{13}$ | H | H | — |
| 1-27 | | | | $C_6H_{13}$ | H | H | Group of Formula 2 | H | $CH_3$ | $OC_6H_{17}$ | H | H | — |
| 1-28 | | | | $C_6H_{13}$ | H | H | Group of Formula 2 | H | $CH_3$ | $COC_6H_{13}$ | H | H | — |
| 1-29 | S | CH | N | $C_6H_{13}$ | H | H | Group of Formula 2 | H | $CH_3$ | $COOC_6H_{13}$ | H | H | — |
| 1-30 | | | | H | $C_6H_{13}$ | H | Group of Formula 2 | H | $CH_3$ | $OC_6H_{13}$ | H | H | — |
| 1-31 | | | | H | $CH_3$ | H | Group of Formula 2 | H | $CH_3$ | $OC_6H_{13}$ | H | H | — |
| 1-32 | | | | H | Br | H | Group of Formula 2 | H | $CH_3$ | $OC_6H_{13}$ | H | H | — |
| 1-33 | | | | H | $C_6H_{13}$ | H | Group of Formula 2 | H | H | $OC_6H_{13}$ | H | H | — |
| 1-34 | | | | H | $CH_3$ | H | Group of Formula 2 | H | H | $OC_6H_{13}$ | H | H | — |
| 1-35 | | | | H | Br | H | Group of Formula 2 | H | H | $OC_6H_{13}$ | H | H | — |
| 1-36 | | | | $C_6H_{13}$ | H | H | Group of Formula 2 | H | $CH_3$ | $C_6H_{13}$ | H | H | — |
| 1-37 | | | | $CH_3$ | H | H | Group of Formula 2 | H | $CH_3$ | $C_6H_{13}$ | H | H | — |
| 1-38 | | | | Br | H | H | Group of Formula 2 | H | $CH_3$ | $C_6H_{13}$ | H | H | — |
| 1-39 | | | | $OCH_3$ | H | H | Group of Formula 2 | H | $CH_3$ | $C_6H_{13}$ | H | H | — |
| 1-40 | | | | $C_6H_{13}$ | H | H | Group of Formula 2 | H | H | $C_6H_{13}$ | H | H | — |
| 1-41 | | | | $CH_3$ | H | H | Group of Formula 2 | H | H | $C_6H_{13}$ | H | H | — |
| 1-42 | | | | Br | H | H | Group of Formula 2 | H | H | $C_6H_{13}$ | H | H | — |
| 1-43 | | | | $OCH_3$ | H | H | Group of Formula 2 | H | H | $C_6H_{13}$ | H | H | — |
| 1-44 | | | | H | $C_6H_{13}$ | H | Group of Formula 2 | H | H | $C_6H_{13}$ | H | H | — |
| 1-45 | | | | H | $CH_3$ | H | Group of Formula 2 | H | H | $C_6H_{13}$ | H | H | — |
| 1-46 | | | | H | Br | H | Group of Formula 2 | H | H | $C_6H_{13}$ | H | H | — |
| 1-47 | | | | H | $OCH_3$ | H | Group of Formula 2 | H | H | $C_6H_{13}$ | H | H | — |
| 1-48 | | | | $CH_3$ | H | H | Group of Formula 2 | H | $OC_6H_{13}$ | H | H | H | — |
| 1-49 | | | | $C_6H_{13}$ | H | Group of Formula 2 | H | H | $CH_3$ | $OC_6H_{13}$ | H | H | — |
| 1-50 | | N | CH | $C_6H_{13}$ | H | H | Group of Formula 2 | H | $CH_3$ | $OC_6H_{13}$ | H | H | — |
| 1-51 | | | | $C_6H_{13}$ | H | H | Group of Formula 2 | H | H | $OC_6H_{13}$ | H | H | — |
| 1-52 | O | CH | N | $C_6H_{13}$ | H | H | Group of Formula 2 | H | $CH_3$ | $OC_6H_{13}$ | H | H | — |
| 1-53 | | | | H | $C_6H_{13}$ | H | Group of Formula 2 | H | $CH_3$ | $OC_6H_{13}$ | H | H | — |
| 1-54 | | | | $C_6H_{13}$ | H | H | Group of Formula 2 | H | H | $OC_6H_{13}$ | H | H | — |
| 1-55 | | | | Br | H | H | Group of Formula 2 | H | $CH_3$ | $OC_6H_{13}$ | H | H | — |
| 1-56 | | | | H | Br | H | Group of Formula 2 | H | $CH_3$ | $OC_6H_{13}$ | H | H | — |
| 1-57 | | | | Br | H | H | Group of Formula 2 | H | H | $OC_6H_{13}$ | H | H | — |
| 1-58 | | | | $C_6H_{13}$ | H | Group of Formula 2 | H | H | $CH_3$ | $OC_6H_{13}$ | H | H | — |
| 1-59 | $NR_{10}$ | CH | N | H | H | Group of Formula 2 | H | H | $CH_3$ | $OC_6H_{13}$ | H | H | H |
| 1-60 | | | | H | H | Group of Formula 2 | H | H | $CH_3$ | $OC_6H_{13}$ | H | H | $CH_3$ |
| 1-61 | | | | H | H | Group of Formula 2 | H | H | $CH_3$ | $OC_6H_{13}$ | H | H | $C_2H_5$ |
| 1-62 | | | | H | H | Group of Formula 2 | H | H | $CH_3$ | $OC_6H_{13}$ | H | H | $C_8H_{17}$ |
| 1-63 | | | | $C_6H_{13}$ | H | Group of Formula 2 | H | H | $CH_3$ | $OC_6H_{13}$ | H | H | $CH_3$ |
| 1-64 | | | | $OC_6H_{13}$ | H | Group of Formula 2 | H | H | $CH_3$ | $OC_6H_{13}$ | H | H | $CH_3$ |

TABLE 1-1-continued

| Compound X | $Z_1$ | $Z_2$ | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|---|---|
| 1-65 | | | Br | H | Group of Formula 2 | H | H | $CH_3$ | $OC_6H_{13}$ | H | H | $CH_3$ |
| 1-66 | | | Br | H | Group of Formula 2 | H | H | $CH_3$ | $OC_6H_{13}$ | H | H | H |
| 1-67 | | | $C_6H_{13}$ | H | Group of Formula 2 | H | H | H | $OC_6H_{13}$ | H | H | $CH_3$ |
| 1-68 | | | Br | H | Group of Formula 2 | H | H | H | $OC_6H_{13}$ | H | H | $CH_3$ |
| 1-69 | | | H | $C_6H_{13}$ | Group of Formula 2 | H | H | $CH_3$ | $OC_6H_{13}$ | H | H | $CH_3$ |
| 1-70 | | | H | H | H | Group of Formula 2 | H | $CH_3$ | $OC_6H_{13}$ | H | H | H |
| 1-71 | | | H | H | H | Group of Formula 2 | H | $CH_3$ | $OC_6H_{13}$ | H | H | $C_6H_{13}$ |
| 1-72 | | | $C_6H_{13}$ | H | H | Group of Formula 2 | H | $CH_3$ | $OC_6H_{13}$ | H | H | $CH_3$ |
| 1-73 | | | H | $C_6H_{13}$ | H | Group of Formula 2 | H | $CH_3$ | $OC_6H_{13}$ | H | H | $CH_3$ |
| 1-74 | | | $C_6H_{13}$ | H | H | Group of Formula 2 | H | H | $OC_6H_{13}$ | H | H | $CH_3$ |

The "group of Formula 2" in $R_3$ and $R_4$ of Table 1-1 (Table 1-1-1 to Table 1-1-3) refers to a "group represented by the Chemical Formula 2".

The alkyl group having 1 to 18 carbon atoms, the alkoxy group having 1 to 18 carbon atoms, the acyl group having 2 to 19 carbon atoms, or the alkoxycarbonyl group having 2 to 19 carbon atoms, which are used for $R_1$ to $R_{10}$ as described above, may be linear or may be branched.

Meanwhile, the molecular weight of the compound represented by the Chemical Formula 1 of the present invention is not particularly limited; however, the molecular weight is preferably 100 or more and less than 1,000, and more preferably 100 or more and 800 or less. Meanwhile, it should be noted that the compound represented by the Chemical Formula 1 of the present invention does not include a polymer. According to a preferred embodiment, the compound represented by the Chemical Formula 1 is configured not to include a repeating unit. According to a preferred embodiment, the compound represented by the Chemical Formula 1 is not a compound obtainable by polymerizing a monomer containing a polymerizable group.

The wavelength of the irradiated light at the time when the compound having an azomethine part is fluidized by being irradiated with light is preferably in the range of 280 nm or more and 480 nm or less, more preferably in the range of 300 nm or more and 420 nm or less, and even more preferably in the range of 330 nm or more and 420 nm or less. With this range, since light is effectively absorbed, photo-meltability is improved, and fixability is improved. Furthermore, by irradiating with irradiation light having the above-described wavelength, the compound can be fluidized even without applying heat or pressure. However, when the compound is fluidized, fluidization may be accelerated by applying heat or pressure in addition to light irradiation. By applying heat or pressure, the compound can be fluidized with a smaller amount of light irradiation. Therefore, when the compound having an azomethine part is introduced into toner, a toner that can be fixed at the above-mentioned wavelength and has high color reproducibility can be obtained. Meanwhile, the above-mentioned wavelength range is the region of ultraviolet radiation; however, the region of visible light close to ultraviolet radiation is also included. It is because even with irradiation light in the region of visible light close to ultraviolet radiation, the compound having an azomethine part can be fluidized by the irradiation conditions described below.

Regarding the irradiation conditions for the irradiation light at the time when the compound having an azomethine part is fluidized, the amount of irradiation is preferably within the range of 0.1 J/cm² or more and 200 J/cm² or less, more preferably within the range of 0.1 J/cm² or more and 100 J/cm² or less, and even more preferably within the range of 0.1 J/cm² or more and 50 J/cm² or less.

On the other hand, regarding the conditions in which the compound having an azomethine part is non-fluidized (re-solidified), it is preferable to leave the compound to stand at room temperature (in the range of 25±15° C.), that is, to leave the compound in a natural environment. At this time, it is desirable to leave the compound in the dark; however, the compound may receive visible light such as natural light or fluorescent light. Furthermore, in the course of non-fluidizing, it is more preferable to apply heat. Furthermore, it is also acceptable to apply light.

The method for synthesizing the compound having an azomethine part of the present invention is not particularly limited, and any conventionally known synthesis method can be applied. For example, to take an example of a compound 1-21 of Table 1-1, in which the heterocyclic ring of the Chemical Formula 1 is a thiophene ring, the compound can be synthesized by the following Schemes 1 to 3. The thiophene compounds of compounds 1-1 to 1-20 and 1-22 to 1-49 of Table 1-1 can also be synthesized by a method similar to the synthesis of the compound 1-21 of Table 1-1 shown below.

When 4-nitrophenol and 1-iodohexane ($C_6H_{13}I$) as raw materials are caused to react in dimethylformamide (DMF) using potassium carbonate ($K_2CO_3$) by heating to reflux, and the reaction liquid is washed with water, subsequently concentrated, and purified, 4-hexyloxynitrobenzene can be obtained (see the following Scheme 1).

In a mixed solvent of ethanol (EtOH) and tetrahydrofuran (THF), hydrogen gas ($H_2$) is stirred, while being enclosed, to react with the 4-hexyloxynitrobenzene obtained in Scheme 1 on palladium-carbon (Pd/C catalyst), the catalyst is removed from the reaction liquid, and the solution is concentrated and then is subjected to recrystallization from ethanol. Thereby, 4-(hexyloxy)aniline can be obtained (see the following Scheme 2).

When 4-(hexyloxy)aniline obtained in Scheme 2 and 5-bromothiophene-2-carboxyaldehyde are heated and stirred to react in ethanol (EtOH), the reaction liquid is filtered, and a powder thus obtained is washed with cold ethanol and recrystallized from methanol/ethanol, the compound 1-21 of Table 1-1, which is a target substance, can be obtained (see the following Scheme 3). The temperature at the time of heating and stirring in Scheme 3 is preferably within the range of 0° C. or higher and 100° C. or lower, more preferably within the range of 30° C. or higher and 70° C. or lower, and even more preferably within the range of 40° C. or higher and 60° C. or lower.

is filtered, and a powder thus obtained is washed with cold ethanol and recrystallized from methanol/ethanol, the compound 1-50 as a target substance can be obtained (see the following Scheme 5). The temperature at the time of heating and stirring in Scheme 5 is preferably within the range of 0° C. or higher and 100° C. or lower, more preferably within the range of 30° C. or higher and 70° C. or lower, and even more preferably within the range of 40° C. or higher and 60° C. or lower.

Scheme 1

[Chemical Formula 6]

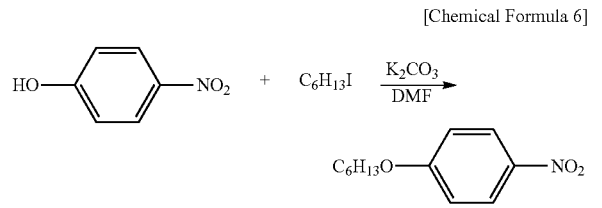

Scheme 2

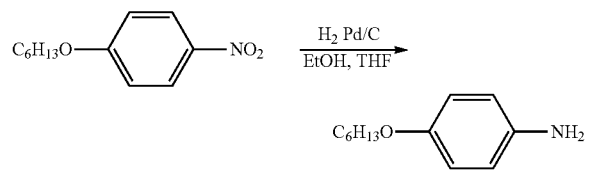

Scheme 3

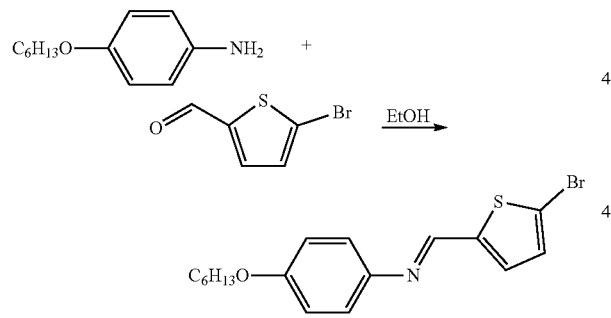

Scheme 4

[Chemical Formula 7]

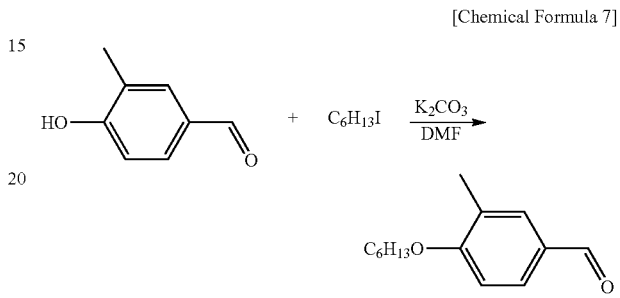

Scheme 5

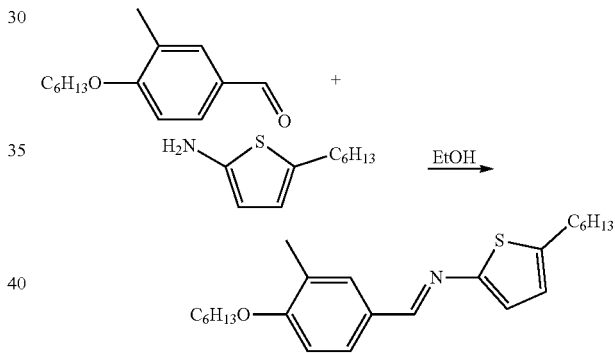

Furthermore, for example, to take an example of a compound 1-50 of Table 1-1, in which the heterocyclic ring of the Chemical Formula 1 is a thiophene ring, the compound can be synthesized by the following Schemes 4 to 5. The thiophene compound of a compound 1-51 of Table 1-1 can also be synthesized by a method similar to the synthesis of the compound 1-50 of Table 1-1 shown below.

When 4-hydroxy-3-methylbenzaldehyde and 1-iodohexane ($C_6H_{13}I$) as raw materials are caused to react in dimethylformamide (DMF) using potassium carbonate ($K_2CO_3$) by heating to reflux, and the reaction liquid is washed with water, subsequently concentrated, and purified, 4-hexyloxy-3-methylbenzaldehyde can be obtained (see the following Scheme 4).

When the 4-hexyloxy-3-methylbenzaldehyde obtained in Scheme 4 and 5-hexylthiophene-2-amine are caused to react by heating and stirring in ethanol (EtOH), the reaction liquid Furthermore, for example, to take an example of a compound 1-55 of Table 1-1, in which the heterocyclic ring of the Chemical Formula 1 is a furan ring, the compound can be synthesized by the following Schemes 6 to 8. The furan compounds of compounds 1-52 to 1-54 and 1-56 to 1-58 of Table 1-1 can also be synthesized by a method similar to the synthesis of the compound 1-55 of Table 1-1 shown below. Furthermore, for example, regarding furan rings obtained by substituting $Z_1$ and $Z_2$ of the compounds 1-52 to 1-58 of Table 1-1, although no example is illustrated in Table 1-1, synthesis can be achieved by referring to the above-described Schemes 4 and 5 and the following Schemes 6 to 8.

When 2-methyl-4-nitrophenol and 1-iodohexane ($C_6H_{13}I$) as raw materials are caused to react in dimethylformamide (DMF) using potassium carbonate ($K_2CO_3$) by heating to reflux, and the reaction liquid is washed with water, subsequently concentrated, and purified, 3-methyl-4-hexyloxynitrobenzene can be obtained (see the following Scheme 6).

In a mixed solvent of ethanol (EtOH) and tetrahydrofuran (THF), hydrogen gas ($H_2$) is stirred, while being enclosed, to react with the 3-methyl-4-(hexyloxy)nitrobenzene obtained in Scheme 6 on palladium-carbon (Pd/C catalyst), the catalyst is removed from the reaction liquid, and the solution is concentrated and then is subjected to recrystallization from ethanol. Thereby, 3-methyl-4-(hexyloxy)aniline can be obtained (see the following Scheme 7).

When the 3-methyl-4-(hexyloxy)aniline obtained in Scheme 7 and 5-bromo-2-furaldehyde are heated and stirred to react in ethanol (EtOH), the reaction liquid is filtered, and a powder thus obtained is washed with cold ethanol and recrystallized from methanol/ethanol, the compound 1-55 as a target substance can be obtained (see the following Scheme 8). The temperature at the time of heating and stirring in Scheme 8 is preferably within the range of 0° C. or higher and 100° C. or lower, more preferably within the range of 30° C. or higher and 70° C. or lower, and even more preferably within the range of 40° C. or higher and 60° C. or lower.

Scheme 6

[Chemical Formula 8]

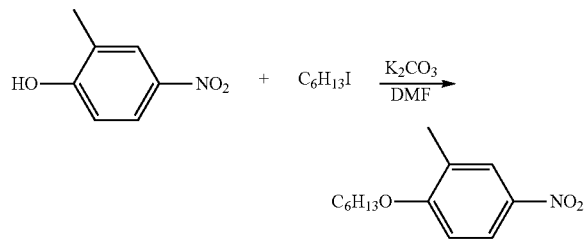

Scheme 7

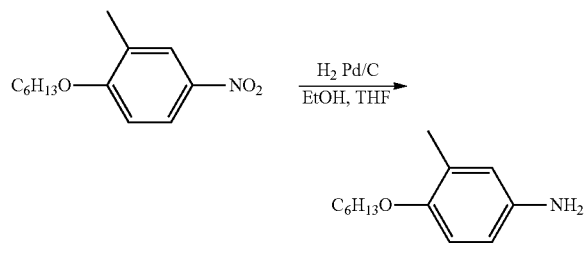

Scheme 8

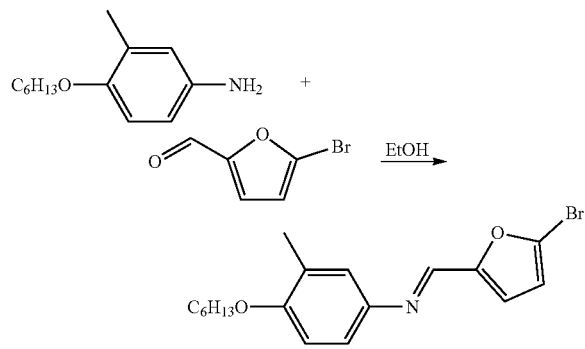

Furthermore, for example, to take an example of a compound 1-70 of Table 1-1, in which the heterocyclic ring of the Chemical Formula 1 is a pyrrole ring, the compound can be synthesized by the following Schemes 9 to 11. The pyrrole compounds of compounds 1-59 to 1-69 and 1-71 to 1-74 of Table 1-1 can also be synthesized by a method similar to the synthesis of the compound 1-70 of Table 1-1 shown below. Furthermore, for example, regarding pyrrole rings obtained by substituting $Z_1$ and $Z_2$ of the compounds 1-59 to 1-74 of Table 1-1, although no example is illustrated in Table 1-1, synthesis can be achieved by referring to the above-described Schemes 4 and 5 and the following Schemes 9 to 11.

When 2-methyl-4-nitrophenol and 1-iodohexane ($C_6H_{13}I$) of raw materials are caused to react in dimethylformamide (DMF) using potassium carbonate ($K_2CO_3$) by heating to reflux, and the reaction liquid is washed with water, subsequently concentrated, and purified, 4-hexyloxy-3-methylnitrobenzene can be obtained (see the following Scheme 9).

In a mixed solvent of ethanol (EtOH) and tetrahydrofuran (THF), hydrogen gas ($H_2$) is stirred, while being enclosed, to react with the 4-hexyloxy-3-methylnitrobenzene obtained in Scheme 9 on palladium-carbon (Pd/C catalyst), the catalyst is removed from the reaction liquid, and the solution is concentrated and then is subjected to recrystallization from ethanol. Thereby, 3-methyl-4-(hexyloxy)aniline can be obtained (see the following Scheme 10).

When the 3-methyl-4-(hexyloxy)aniline obtained in Scheme 10 and pyrrole-2-carboxyaldehyde are heated and stirred to react in ethanol (EtOH), the reaction liquid is filtered, and a powder thus obtained is washed with cold ethanol and recrystallized from methanol/ethanol, the compound 1-70 as a target substance can be obtained (see the following Scheme 11). The temperature at the time of heating and stirring in Scheme 11 is preferably within the range of 0° C. or higher and 100° C. or lower, more preferably within the range of 30° C. or higher and 70° C. or lower, and even more preferably within the range of 40° C. or higher and 60° C. or lower.

Scheme 9

[Chemical Formula 9]

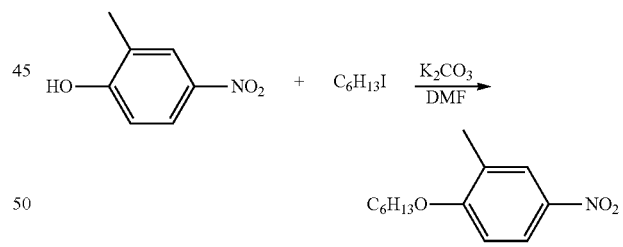

Scheme 10

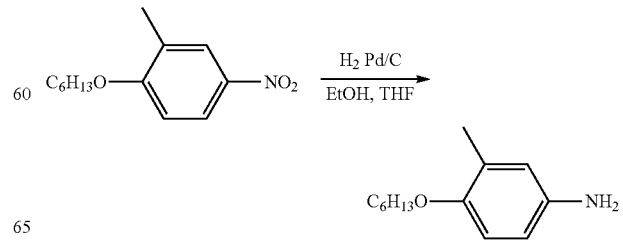

Scheme 11

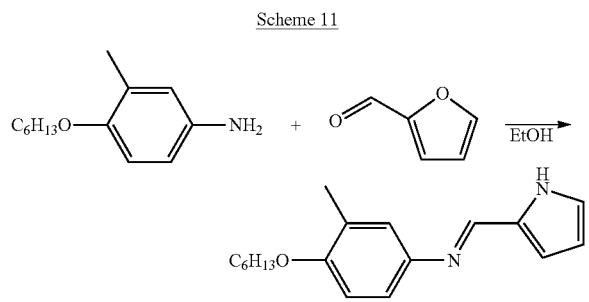

The compounds having an azomethine part of the present invention can be used singly or in combination of two or more kinds thereof.

Second Embodiment

A second embodiment of the present invention is a photoresponsive compound represented by a following General Formula (1), the photoresponsive compound being fluidized by being irradiated with light and reversibly non-fluidized:

[Chemical Formula 10]

General Formula (1)

wherein in the General Formula (1), $Z_1$ and $Z_2$ each independently represent N or CH, while $Z_1 \neq Z_2$;

A and B each independently represent a substituted or unsubstituted aromatic hydrocarbon group or a substituted or unsubstituted aromatic heterocyclic group; and an activation energy Ea represented by a following Formula (1) is 60 kJ/mol or greater:

Ea(kJ/mol)=(Total energy of TS(kJ/mol))−(Total energy of cis-form(kJ/mol))  Formula (1):

wherein in the Formula (1), TS represents a transition state represented by General Formula (2); and the cis-form represents an isomer represented by General Formula (3):

[Chemical Formula 11]

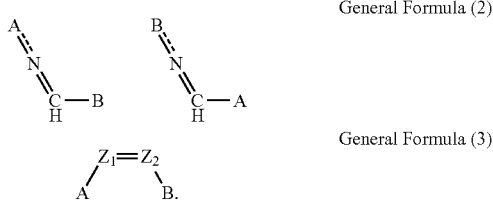

General Formula (2)

General Formula (3)

According to the second embodiment of the present invention, a compound that is fluidized by being irradiated with light and is reversibly non-fluidized, and that does not undergo noticeable coloration, can be provided.

By using a compound (compound having an azomethine part) represented by the General Formula (1) and having predetermined activation energy, a photoresponsive compound that is fluidized by being irradiated with light and is reversibly non-fluidized, and that does not undergo coloration to the extent that does not affect the reproduction of a desired color when applied to a toner or an adhesive, can be realized.

The details about why the above-described effect is obtained by the compound of the present invention are not clearly understood; however, the following mechanism may be considered. Meanwhile, the following mechanism is based on speculation, and the present invention is not limited to the following mechanism. In the following description, the compound represented by the General Formula (1) is also referred to as "compound having an azomethine part" or "azomethine derivative".

An azobenzene compound is known to be a material that absorbs light and is softened from a solid state (photo-induced phase transition), that is, a material that is fluidized by being irradiated with light, and the photo-induced phase transition is considered to occur as the crystal structure is destroyed by cis-trans isomerization. In the azobenzene compounds described in Japanese Patent Application Laid-Open No. 2011-256155 (corresponding to US 2013/066068A1) or Japanese Patent Application Laid-Open No. 2011-256291, phase change occurs concomitantly with an isomerization reaction caused by light irradiation; however, these compounds exhibit strong absorption originating from n-π* transition in the long wavelength region and are colored in orange. Therefore, there has been a problem that a desired color cannot be reproduced when the compounds are applied to industrial products.

In the present invention, providing a compound that is fluidized by being irradiated with light and is reversibly non-fluidized and that does not undergo noticeable coloration was realized by using a compound having an azomethine part. By introducing an azomethine part instead of an azobenzene compound, strong n-π* absorption in the azobenzene compound can be weakened, and therefore, a compound that does not undergo noticeable coloration can be realized.

Furthermore, with regard to a compound that is fluidized and non-fluidized concomitantly with photo-isomerization, it is considered that when a non-fluid trans-form (E) is irradiated with light and is isomerized into a cis-form (Z), as many trans-forms keep changing into cis-forms, a regular structure is destroyed, and a phase transition change, that is, a fluidization phenomenon, can be induced. Furthermore, it is speculated that when a cis-form turns back and forth to a trans-form, a regular structure is formed again, and a non-fluidization phenomenon can be induced. Therefore, it is speculated that in order to induce a fluidization phenomenon, many trans-forms (E) need to be isomerized into cis-forms (Z). However, generally, it is known for an azomethine compound that the rate of isomerization from the Z-form to the E-form is fast compared to an azobenzene compound, and in an azomethine compound having an unsubstituted benzene introduced into both terminals, it was anticipated that it would be disadvantageous to induce fluidization and reversible non-fluidization.

When it is said that the rate of isomerization from the Z-form to the E-form is fast, it is thought that since the energy barrier in the isomerization reaction from the Z-form to the E-form is low, the compound returns rapidly to the trans-form (E). The present inventors thought that by controlling the energy barrier (activation energy Ea) in the isomerization reaction from the Z-form to the E-form, the rate of isomerization from the Z-form to the E-form can be controlled. Then, the inventors found that by adjusting the energy barrier (activation energy Ea) in the isomerization reaction from the Z-form to the E-form to 60 kJ/mol or greater, the reaction rate of the isomerization reaction from the Z-form to the E-form can be controlled, and the compound can be fluidized by being irradiated with light and be reversibly non-fluidized.

Meanwhile, in the present specification, when a compound is fluidized by being irradiated with light and is reversibly non-fluidized, it implies that the compound changes from a non-fluid state to a fluid state by light irradiation, and further returns to a non-fluid state.

From the above-described reasons, it is thought that the compound having an azomethine part of the present invention is colorless and is capable of inducing a fluidization and non-fluidization phenomenon concomitantly with isomerization. Therefore, by introducing the compound having an azomethine part of the present invention into a toner, a toner that can be fixed by light irradiation as a fixing means other than thermal fixing and has high color reproducibility can be obtained.

Meanwhile, fluid state according to the present invention refers to a state that is transformed without any external force or by a small external force.

Hereinafter, preferred embodiments of the present invention will be described. Meanwhile, according to the present specification, the expression "X to Y" representing a range means "X or more and Y or less". Furthermore, according to the present specification, unless particularly stated otherwise, operations and measurement of physical properties and the like are carried out under the conditions of room temperature (20° C. to 25° C.)/relative humidity of 40% to 50% RH.

<Compound Having Azomethine Part>

The compound having an azomethine part of the present invention is a photoresponsive compound represented by the following General Formula (1), which is fluidized by being irradiated with light and is reversibly non-fluidized.

[Chemical Formula 12]

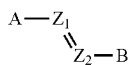

General Formula (1)

In the General Formula (1), $Z_1$ and $Z_2$ each independently represent N or CH, while $Z_1 \neq Z_2$; and A and B each independently represent a substituted or unsubstituted aromatic hydrocarbon group or a substituted or unsubstituted aromatic heterocyclic group.

The compound of the present invention is such that the activation energy Ea represented by the following Formula (1) is 60 kJ/mol or greater.

$Ea$(kJ/mol)=(Total energy of $TS$(kJ/mol))−(Total energy of cis-form(kJ/mol))    Formula (1):

In the Formula (1), TS represents a transition state represented by the General Formula (2); and the cis-form refers to an isomer represented by the General Formula (3).

[Chemical Formula 13]

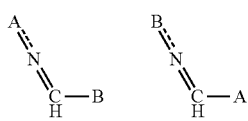

General Formula (2)

-continued

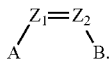

General Formula (3)

When the activation energy Ea represented by Formula (1) is below 60 kJ/mol, since the barrier of the isomerization reaction from the cis-form to the trans-form is low, even if the compound is isomerized to a fluid cis-form by light irradiation, the compound returns rapidly to the non-fluid trans-form. Therefore, fluidization by light irradiation and subsequent reversible non-fluidization cannot be realized.

Preferably, the activation energy Ea is 63 kJ/mol or greater, more preferably 64 kJ/mol or greater, and even more preferably 65 kJ/mol or greater. Furthermore, from the viewpoint of the ease of returning to the trans-form, the activation energy Ea is preferably 100 kJ/mol or lower, more preferably 95 kJ/mol or lower, even more preferably 90 kJ/mol or lower, and still more preferably 80 kJ/mol or lower. In this way, the effects of the present invention can be obtained more easily.

Here, the calculation of the molecular structure and the total energy of the cis-form of the compound of the present invention, and the molecular structure and the total energy of the transition state can be carried out using Gaussian 16 (Revision B.01, M. J. Frisch, G. W. Trucks, H. B. Schlegel, G. E. Scuseria, M. A. Robb, J. R. Cheeseman, G. Scalmani, V. Barone, G. A. Petersson, H. Nakatsuji, X. Li, M. Caricato, A. V. Marenich, J. Bloino, B. G. Janesko, R. Gomperts, B. Mennucci, H. P. Hratchian, J. V. Ortiz, A. F. Izmaylov, J. L. Sonnenberg, D. Williams-Young, F. Ding, F. Lipparini, F. Egidi, J. Goings, B. Peng, A. Petrone, T. Henderson, D. Ranasinghe, V. G. Zakrzewski, J. Gao, N. Rega, G. Zheng, W. Liang, M. Hada, M. Ehara, K. Toyota, R. Fukuda, J. Hasegawa, M. Ishida, T. Nakajima, Y. Honda, O. Kitao, H. Nakai, T. Vreven, K. Throssell, J. A. Montgomery, Jr., J. E. Peralta, F. Ogliaro, M. J. Bearpark, J. J. Heyd, E. N. Brothers, K. N. Kudin, V. N. Staroverov, T. A. Keith, R. Kobayashi, J. Normand, K. Raghavachari, A. P. Rendell, J. C. Burant, S. S. Iyengar, J. Tomasi, M. Cossi, J. M. Millam, M. Klene, C. Adamo, R. Cammi, J. W. Ochterski, R. L. Martin, K. Morokuma, O. Farkas, J. B. Foresman, and D. J. Fox, Gaussian, Inc., Wallingford Conn., 2016) software manufactured by Gaussian, Inc. in the USA, and as the calculation technique, a density functional method (B3LYP/6-31G(d)) can be used. Regarding the molecular structure of the cis-form, the most stable molecular structure, that is, the molecular structure having the lowest total energy, of an isomer represented by the General Formula (3) is calculated, and this total energy is designated as the total energy of the cis-form. Regarding the molecular structure of the transition state (TS), for the transition state represented by the General Formula (2), the saddle point of the corresponding molecular structure is calculated, and the total energy obtained at this time is designated as the total energy of the transition state. Meanwhile, there are no particular limitations in the software or the calculation technique, and the same value can be obtained by using any of them. From the calculation value obtained as such, the value of the activation energy Ea can be determined according to the Formula (1).

With regard to the compound having an azomethine part of the present invention, the structures of A and B of the General Formula (1) are selected as appropriate, the activation energy Ea represented by the Formula (1) can be controlled to be 60 kJ/mol or greater.

Specifically, by introducing an electron-donating structure into a compound having an azomethine part, the electron density of the azomethine part is increased, and the activation energy Ea can be increased. For example, the activation energy Ea can be increased by adopting an aromatic heterocyclic group having high electron-donating properties for at least one of A and B. Furthermore, the activation energy Ea can be increased by introducing a substituent having high electron-donating properties for the aromatic hydrocarbon group or the aromatic heterocyclic group as A and B.

Here, the aromatic hydrocarbon group is not particularly limited; however, an aryl group having 6 to 30 carbon atoms is preferred, and examples include a phenyl group, a naphthyl group, an anthracenyl group, a phenanthrenyl group, a pyrenyl group, and the like. Among them, from the viewpoint that fluidization and non-fluidization occur effectively, a phenyl group is preferred.

The aromatic heterocyclic group is not particularly limited; however, an aromatic heterocyclic group having 2 to 30 carbon atoms is preferred. Furthermore, a group having high electron-donating properties is preferred, and examples include a thienyl group, a pyrrolyl group, a pyrazolyl group, an imidazolyl group, a pyridyl group, a pyrimidinyl group, a pyrazinyl group, a triazinyl group, a benzothienyl group, a benzimidazolyl group, an indolyl group, an isoindolyl group, a quinolinyl group, an isoquinolinyl group, a quinazolinyl group, quinoxalinyl group, a naphthyridinyl group, an acrydinyl group, a carbazolyl group, a dibenzothienyl group, and the like; however, examples are not limited to these. Among them, from the viewpoint that the activation energy increases, and fluidization and non-fluidization occur effectively, a thienyl group, a pyrrolyl group, a pyrazolyl group, an imidazolyl group, an indolyl group, and a carbazolyl group are preferred.

The aromatic hydrocarbon group or aromatic heterocyclic group described above may each have a substituent. The substituent is not particularly limited; however, examples include a halogen atom, a cyano group, a nitro group, an amino group, an alkyl group having 1 to 18 carbon atoms, an alkoxy group having 1 to 18 carbon atoms, an alkylamino group having 1 to 10 carbon atoms, a dialkylamino group having 2 to 10 carbon atoms, an acyl group having 2 to 19 carbon atoms, an alkoxycarbonyl group having 2 to 19 carbon atoms, and the like. Preferred examples include a halogen atom, a cyano group, a nitro group, an alkyl group having 1 to 18 carbon atoms, an alkoxy group having 1 to 18 carbon atoms, a dialkylamino group having 2 to 10 carbon atoms, an acyl group having 2 to 19 carbon atoms, and an alkoxycarbonyl group having 2 to 19 carbon atoms.

As described above, it is thought that the photo-induced phase transition of an azomethine compound occurs, similarly to an azobenzene compound, as the crystal structure is destroyed by cis-trans isomerization. Generally, since the intermolecular π-π interaction is strong, the photo-induced phase transition occurs only at the outermost surface of the crystal structure. Here, when the aromatic hydrocarbon group or aromatic heterocyclic group represented by A or B of General Formula (1) has a substituent, the compound having an azomethine part of the present invention forms a unique crystal structure in which within a periodic structure in which the π-π interaction is predominant, a structure that is isotropically disordered by thermal motion of these substituents co-exist. Therefore, when the cis-trans isomerization reaction proceeds locally and the π-π interaction of the azomethine part is reduced, isotropic fusion occurs in a chain reaction over the entire system. Therefore, it is considered that the cis-trans isomerization can proceed more easily, and fluidization can be exhibited easily.

At this time, it is preferable that at least one of the above-described substituents is a halogen atom, a cyano group, a nitro group, an alkyl group having 1 to 18 carbon atoms, an alkoxy group having 1 to 18 carbon atoms, a dialkylamino group having 2 to 10 carbon atoms, an acyl group having 2 to 18 carbon atoms, or an alkoxycarbonyl group having 2 to 18 carbon atoms. It is considered that by adopting such a structure, cis-trans isomerization can proceed more easily, and fluidization can be exhibited easily. Among these, from the viewpoint of having high thermal mobility, it is more preferable that the substituent is an alkyl group having 1 to 18 carbon atoms, an alkoxy group having 1 to 18 carbon atoms, or a dialkylamino group having 2 to 10 carbon atoms.

Regarding the number of carbon atoms of the substituent, more preferably, the alkyl group is an alkyl group having 1 to 12 carbon atoms, and even more preferably an alkyl group having 4 to 12 carbon atoms. Furthermore, more preferably, the alkoxy group is an alkoxy group having 1 to 12 carbon atoms, and even more preferably an alkoxy group having 4 to 12 carbon atoms. Furthermore, more preferably, the dialkylamino group is a dialkylamino group having 2 to 8 carbon atoms, and even more preferably a dialkylamino group having 4 to 6 carbon atoms. More preferably, the acyl group is an acyl group having 2 to 13 carbon atoms, and even more preferably an acyl group having 5 to 13 carbon atoms. Furthermore, more preferably, the alkoxycarbonyl group is an alkoxycarbonyl group having 2 to 13 carbon atoms, and even more preferably, an alkoxycarbonyl group having 5 13 carbon atoms is even more preferred. As such, by introducing a long-chain substituent, crystals become liable to be destroyed, photo-meltability is improved, and fixability is improved when the compound is used in a toner.

Examples of the alkyl group having 1 to 18 carbon atoms are not particularly limited, and examples include linear alkyl groups such as a methyl group, an ethyl group, an n-propyl group, an n-butyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, and an n-hexadecyl group; and branched alkyl groups such as an isopropyl group, a sec-butyl group, an isobutyl group, a t-butyl group, a 1-methylpentyl group, a 4-methyl-2-pentyl group, a 3,3-dimethylbutyl group, a 2-ethylbutyl group, a 1-methylhexyl group, a t-octyl group, a 1-methylheptyl group, a 2-ethylhexyl group, a 2-propylpentyl group, a 2,2-dimethylheptyl group, a 2,6-dimethyl-4-heptyl group, a 3,5,5-trimethylhexyl group, a 1-methyldecyl group, and a 1-hexylheptyl group.

Examples of the alkoxy group having 1 to 18 carbon atoms include linear alkoxy groups such as a methoxy group, an ethoxy group, an n-propoxy group, an n-butoxy group, an n-hexyloxy group, an n-heptyloxy group, an n-octyloxy group, an n-nonyloxy group, an n-decyloxy group, an n-undecyloxy group, an n-dodecyloxy group, an n-tridecyloxy group, an n-tetradecyloxy group, an n-pentadecyl group, and an n-hexadecyloxy group; and branched alkoxy groups such as a 1-methylpentyloxy group, a 4-methyl-2-pentyloxy group, a 3,3-dimethylbutyloxy group, a 2-ethylbutyloxy group, a 1-methylhexyloxy group, a t-octyloxy group, a 1-methylheptyloxy group, a 2-ethylhexyloxy group, a 2-propylpentyloxy group, a 2,2-dimethylheptyloxy group, a 2,6-dimethyl-4-heptyloxy group, a 3,5,5-trimethylhexyloxy group, a 1-methyldecyloxy group, and a 1-hexylheptyloxy group.

Examples of the alkylamino group having 1 to 10 carbon atoms include, for example, a methylamino group, an ethylamino group, an n-propylamino group, an n-butylamino group, an isobutylamino group, an n-hexylamino group, an n-heptylamino group, an n-octylamino group, an n-nonylamino group, an n-decylamino group, and the like.

Examples of the dialkylamino group having 2 to 10 carbon atoms include, for example, a dimethylamino group, a diethylamino group, a di-n-propylamino group, a di-n-butylamino group, a diisobutylamino group, a methylethylamino group, and the like.

Examples of the acyl group having 2 to 19 carbon atoms include saturated or unsaturated, linear or branched acyl groups, and examples include an acetyl group, a propanoyl group (propionyl group), a butanoyl group (butyryl group), an isobutanoyl group (isobutyryl group), a pentanoyl group (valeryl group), an isopentanoyl group (isovaleryl group), a sec-pentanoyl group (2-methylbutyryl group), a t-pentanoyl group (pivaloyl group), a hexanoyl group, a heptanoyl group, an octanoyl group, a t-octanoyl group (2,2-dimethylhexanoyl group), a 2-ethylhexanoyl group, a nonanoyl group, an isononanoyl group, a decanoyl group, an isodecanoyl group, an undecanoyl group, a lauroyl group, a myristoyl group, a palmitoyl group, a stearoyl group, a behenoyl group, an undecylenoyl group, an oleoyl group, and the like.

Examples of the alkoxycarbonyl group having 2 to 19 carbon atoms include linear or branched alkoxycarbonyl groups, and examples include linear alkoxycarbonyl groups such as a methoxycarbonyl group, an ethoxycarbonyl group, an n-butoxycarbonyl group, an n-hexyloxycarbonyl group, an n-heptyloxycarbonyl group, an n-octyloxycarbonyl group, an n-nonyloxycarbonyl group, an n-decyloxycarbonyl group, an n-undecyloxycarbonyl group, an n-dodecyloxycarbonyl group, an n-tridecyloxycarbonyl group, an n-tetradecyloxycarbonyl group, an n-pentadecyloxycarbonyl group, and an n-hexadecyloxycarbonyl group; and branched alkoxycarbonyl groups such as a 1-methylpentyloxycarbonyl group, a 4-methyl-2-pentyloxycarbonyl group, a 3,3-dimethylbutyloxycarbonyl group, a 2-ethylbutyloxycarbonyl group, a 1-methylhexyloxycalbonyl group, a t-octyloxycarbonyl group, a 1-methylheptyloxycarbonyl group, a 2-ethylhexyloxycarbonyl group, a 2-propylpentyloxycarbonyl group, a 2,2-dimethylheptyloxycarbonyl group, a 2,6-dimethyl-4-heptyloxycarbonyl group, a 3,5,5-trimethylhexyloxycarbonyl group, a 1-methyldecyloxycarbonyl group, and a 1-hexylheptyloxycarbonyl group.

Preferably, in the General Formula (1), A and B each independently represent a substituted or unsubstituted phenyl group or a substituted or unsubstituted aromatic heterocyclic group. By adopting such a configuration, fluidization and non-fluidization can occur more effectively.

Furthermore, a preferred embodiment of the present invention is a compound in which with regard to the General Formula (1), A and B each independently represent a substituted or unsubstituted phenyl group, and at least one of A and B has at least one substituent selected among an alkyl group having 1 to 18 carbon atoms, an alkoxy group having 1 to 18 carbon atoms, and a dialkylamino group having 2 to 10 carbon atoms. Here, the specific forms of the respective substituents are as described above.

In an azomethine compound having a benzene ring introduced into both terminals, the electron density of the azomethine part is lowered, and the activation energy is liable to be lowered, compared to a case in which either one is an electron-donating aromatic heterocyclic group. However, by introducing the above-described substituent, the electron density of the azomethine part can be increased, the activation energy can be controlled to a predetermined range, and a fluidization and reversible non-fluidization phenomenon can be effectively induced. Furthermore, production of lattice defects, exhibition of free volume, reduction of the $\pi$-$\pi$ interaction, and the like that act advantageously on cis-trans isomerization occur. Therefore, it is considered that cis-trans isomerization can proceed more easily, and fluidization can be exhibited easily.

That is, with regard to the compound having an azomethine part of the present invention, when a compound having a benzene ring at both terminals of the C=N bond has one or more electron-donating substituents (an alkoxy group, a dialkylamino group, and the like) on at least one of the benzene rings, the electron density of the azomethine part increases compared to a case in which both the benzene rings do not have any substituent, or a case in which both the benzene rings have only electron-withdrawing substituents. Therefore, the activation energy is likely to be increased, and a fluidization and reversible non-fluidization phenomenon can be effectively induced, which is therefore preferable.

At this time, it is preferable that at least one of A and B (that is, at least one of the phenyl groups of A and B) has the above-mentioned substituent at the para-position with respect to the $Z_1$ or $Z_2$. As such, by introducing the substituent at the para-position of the benzene ring, crystals become liable to be destroyed, photo-meltability is improved, and fixability is improved. Furthermore, regarding the substituent, since it is thought that the effects described above can be obtained more noticeably by having a carbon chain having a certain length or longer, the substituent is more preferably an alkyl group having 4 to 12 carbon atoms, an alkoxy group having 4 to 12 carbon atoms, or a dialkylamino group having 4 to 10 carbon atoms. In a case in which the A and B are both a phenyl group, it is more preferable that the A and B have the substituent at the para-position with respect to $Z_1$ or $Z_2$ of both the phenyl groups. When the A and B are both a phenyl group and have the substituent at the para-position with respect to $Z_1$ or $Z_2$ of both the phenyl groups, an effect that photo-meltability is improved and fixability is improved can be obtained even more noticeably.

Furthermore, it is more preferable that the A and B are both a phenyl group, and both A and B have the substituent. In this way, an effect that crystals become liable to be destroyed, photo-meltability is improved, and fixability is improved can be obtained even more noticeably.

According to an embodiment of the present invention, it is preferable that the A and B are both a phenyl group, and at least one of A and B is a phenyl group unsubstituted at two ortho-positions and two meta-positions with respect to the $Z_1$ or $Z_2$, or substituted with a group selected among an alkyl group having 1 to 4 carbon atoms, an alkoxy group having 1 to 4 carbon atoms, and a halogen atom. That is, four carbon atoms in total of the two ortho-positions and the two meta-positions may all be unsubstituted, the four carbon atoms in total may be respectively substituted with a group selected among a halogen atom, an alkyl group having 1 to 4 carbon atoms, and an alkoxy group having 1 to 4 carbon atoms, or a portion of the four carbon atoms in total may be unsubstituted, while the others may be substituted with a group selected from a halogen atom, an alkyl group having 1 to 4 carbon atoms, and an alkoxy group having 1 to 4 carbon atoms. Furthermore, in the case of being substituted, the carbon atoms may be respectively substituted with the same group or may be substituted with different groups, as long as the group is selected from a halogen atom, an alkyl group having 1 to 4 carbon atoms, and an alkoxy group having 1 to 4 carbon atoms. Meanwhile, the alkyl group and the alkoxy group may be linear or branched. When such a configuration is adopted, the steric hindrance near the C=N bond can be controlled, and fluidization and non-fluidization can be effectively exhibited. Furthermore, it is preferable because the melting point of the compound can be controlled to a suitable range.

Another preferred embodiment of the present invention is a compound in which at least one of A and B in the General Formula (1) is a phenyl group substituted with at least one substituent selected among an alkyl group having 1 to 18 carbon atoms, an alkoxy group having 1 to 18 carbon atoms, and a dialkylamino group having 2 to 10 carbon atoms, and the other one is a substituted or unsubstituted aromatic heterocyclic group. By the configuration described above, the electron density of the azomethine part can be increased, the activation energy can be controlled to a predetermined range, and a fluidization and reversible non-fluidization phenomenon can be effectively induced. Furthermore, production of lattice defects, exhibition of free volume, reduction of the $\pi$-$\pi$ interaction, and the like that act advantageously on cis-trans isomerization occur. Therefore, it is considered that the cis-trans isomerization can proceed more easily, and fluidization can be exhibited easily. Here, specific forms of the aromatic heterocyclic group and the respective substituents are as described above.

At this time, it is preferable that the phenyl group has the substituent at the para-position with respect to the $Z_1$ or $Z_2$. By introducing a long-chain substituent into the para-position with respect to the $Z_1$ or $Z_2$, crystals become liable to be destroyed, photo-meltability is improved, and fixability is improved when the compound is used in a toner.

Furthermore, it is preferable that the aromatic heterocyclic group is unsubstituted, or the aromatic heterocyclic group is substituted with a halogen atom, a cyano group, a nitro group, an alkyl group having 1 to 18 carbon atoms, an alkoxy group having 1 to 18 carbon atoms, a dialkylamino group having 2 to 10 carbon atoms, an acyl group having 2 to 19 carbon atoms, or an alkoxycarbonyl group having 2 to 19 carbon atoms. By the configuration described above, the activation energy can be easily controlled to a predetermined range, and a fluidization and reversible non-fluidization phenomenon can be effectively induced. Furthermore, production of lattice defects, exhibition of free volume, reduction of the $\pi$-$\pi$ interaction, and the like that act advantageously on cis-trans isomerization occur. Therefore, it is considered that the cis-trans isomerization can proceed more easily, and fluidization can be exhibited easily.

Still another preferred embodiment of the present invention is a compound in which at least one of A and B in the General Formula (1) is a substituted or unsubstituted phenyl group, and the other one is an aromatic heterocyclic group substituted with at least one substituent selected among an alkyl group having 1 to 18 carbon atoms, an alkoxy group having 1 to 18 carbon atoms, and a dialkylamino group having 2 to 10 carbon atoms. By the configuration described above, the electron density of the azomethine part can be increased, the activation energy can be controlled to a predetermined range, and a fluidization and reversible non-fluidization phenomenon can be effectively induced. Furthermore, production of lattice defects, exhibition of free volume, reduction of the $\pi$-$\pi$ interaction, and the like that act advantageous on cis-trans isomerization occur. Therefore, it is considered that the cis-trans isomerization can proceed more easily, and fluidization can be exhibited easily. From the viewpoint of further enhancing photo-meltability, it is more preferable that the aromatic heterocyclic group is an aromatic heterocyclic group substituted with an alkyl group having 4 to 12 carbon atoms, an alkoxy group having 4 to 12 carbon atoms, or a dialkylamino group having 4 to 10 carbon atoms. Here, specific forms of the aromatic heterocyclic group and the respective substituents are as described above.

At this time, the phenyl group is preferably a phenyl group substituted with a halogen atom, a cyano group, a nitro group, an alkyl group having 1 to 18 carbon atoms, an alkoxy group having 1 to 18 carbon atoms, or a dialkylamino group having 2 to 10 carbon atoms. Thereby, production of lattice defects, exhibition of free volume, reduction of the $\pi$-$\pi$ interaction, and the like that act advantageously on cis-trans isomerization occur. Therefore, it is considered that the cis-trans isomerization can proceed more easily, and fluidization can be exhibited easily.

Still another preferred embodiment of the present invention is a compound in which A and B in the General Formula (1) each independently represent a substituted or unsubstituted aromatic heterocyclic group, and at least one of A and B has at least one substituent selected among an alkyl group having 1 to 18 carbon atoms, an alkoxy group having 1 to 18 carbon atoms, and a dialkylamino group having 2 to 10 carbon atoms. By the configuration described above, the electron density of the azomethine part can be increased, the activation energy can be controlled to a predetermined range, and a fluidization and reversible non-fluidization phenomenon can be effectively induced. Furthermore, production of lattice defects, exhibition of free volume, reduction of the $\pi$-$\pi$ interaction, and the like that act advantageously on cis-trans isomerization occur. Therefore, it is considered that the cis-trans isomerization can proceed more easily, and fluidization can be exhibited more easily. Here, the aromatic heterocyclic groups constituting A and B may be identical or different. Here, specific forms of the aromatic heterocyclic groups and the respective substituents are as described above. Meanwhile, from the viewpoint of further enhancing photo-meltability, it is more preferable that at least one of A and B is an aromatic heterocyclic group substituted with an alkyl group having 4 to 12 carbon atoms, an alkoxy group having 4 to 12 carbon atoms, or a dialkylamino group having 4 to 10 carbon atoms.

Furthermore, preferably, one of A and B is an aromatic heterocyclic group having at least one substituent selected among an alkyl group having 1 to 18 carbon atoms, an alkoxy group having 1 to 18 carbon atoms, and a dialkylamino group having 2 to 10 carbon atoms, and the other one is an unsubstituted aromatic heterocyclic group or an aromatic heterocyclic group substituted with a halogen atom, a cyano group, a nitro group, an alkyl group having 1 to 18 carbon atoms, an alkoxy group having 1 to 18 carbon atoms, a dialkylamino group having 2 to 10 carbon atoms, an acyl group having 2 to 19 carbon atoms, or an alkoxycarbonyl group having 2 to 19 carbon atoms. By adopting such a configuration, fluidization and non-fluidization can be exhibited effectively. Furthermore, it is preferable because the melting point of the compound can be controlled to a suitable range.

As described above, the alkyl group having 1 to 18 carbon atoms, the alkoxy group having 1 to 18 carbon atoms, the alkylamino group having 1 to 10 carbon atoms, the dialkylamino group having 2 to 10 carbon atoms, the acyl group having 2 to 19 carbon atoms, or the alkoxycarbonyl group having 2 to 19 carbon atoms may be linear or may be branched.

As described above, it is thought that the compound of the present invention can achieve fluidization and reversible non-fluidization by adjusting the activation energy for photo-isomerization to a predetermined range. Furthermore, as will be described in the Examples of the second embodiment that will be described below, by appropriately selecting A, $Z_1$, $Z_2$, and B in the General Formula (1), the magnitude of the intermolecular interaction can be controlled, and photo-meltability can be controlled.

For example, in the General Formula (1), a compound in which one of A and B is a substituted or unsubstituted phenyl group, and the other one is a substituted or unsubstituted thienyl group, a pyrrolyl group, a pyrazolyl group, an imidazolyl group, or an indolyl group, tends to have a smaller molar absorption coefficient in a solution, compared to a case in which A and B are both a substituted or unsubstituted phenyl group. Therefore, it is speculated that when the compound is irradiated with light, light can reach in a deeper direction, and lower layers as well as upper layers can be photo-melted. Therefore, as the above-described configuration is adopted in addition to the activation energy for photo-isomerization being in a predetermined range, a compound having superior photo-meltability can be obtained. Therefore, in a case in which the compound is used in a toner, fixing can be achieved by light irradiation with a lower irradiation light intensity. Particularly, with a compound in which in the General Formula (1), A represents a substituted or unsubstituted phenyl group; B represents a substituted or unsubstituted thienyl group, a pyrrolyl group, a pyrazolyl group, an imidazolyl group, or an indolyl group; $Z_1$ represents N; and $Z_2$ represents CH, the above-described effects can be obtained more noticeably.

Specific examples of the compound of the present invention include compounds 2-1 to 2-59 of Examples of the second embodiment that will be described below.

Meanwhile, the molecular weight of the compound represented by the General Formula (1) of the present invention is not particularly limited; however, the molecular weight is preferably 100 or more and less than 1,000, and more preferably 100 or more and 800 or less. Meanwhile, the compound represented by the General Formula (1) of the present invention does not include a polymer. According to a preferred embodiment, the compound represented by the General Formula (1) is configured not to include a repeating unit. According to a preferred embodiment, the compound represented by the General Formula (1) is not a compound obtainable by polymerizing a monomer containing a polymerizable group.

The wavelength of the irradiation light at the time when the compound having an azomethine part is fluidized by being irradiated with light is preferably in the range of 280 nm or more and 480 nm or less, more preferably within the range of 300 nm or more and 420 nm or less, and even more preferably within the range of 330 nm or more and 420 nm or less. When the wavelength is in this range, since light is effectively absorbed, photo-meltability is improved, and fixability is improved. Furthermore, when the compound is fluidized, fluidization may be promoted by applying heat or pressure in addition to light irradiation. By applying heat or pressure, the compound can be fluidized with a smaller amount of light irradiation. Therefore, by introducing this compound having an azomethine part into a toner, a toner that can be fixed at the above-mentioned wavelength and has high color reproducibility can be obtained. Meanwhile, the wavelength range described above is the region of ultraviolet radiation; however, the region of visible light close to ultraviolet radiation is also included. It is because the compound having an azomethine part can be fluidized by the following irradiation conditions even with irradiation light in the region of visible light close to ultraviolet radiation.

Regarding the irradiation conditions for irradiation light at the time when the compound having an azomethine part is fluidized, the amount of irradiation is preferably within the range of 0.1 $J/cm^2$ or more and 200 $J/cm^2$ or less, more preferably within the range of 0.1 $J/cm^2$ or more and 100 $J/cm^2$ or less, and even more preferably within the range of 0.1 $J/cm^2$ or more and 50 $J/cm^2$ or less.

On the other hand, it is preferable that the conditions in which the compound having an azomethine part is non-fluidized are arranged such that the compound is left to stand at room temperature (in the range of 25° C.±15° C.), that is, in a natural environment. At this time, it is desirable to leave the compound in the dark; however, the compound may receive visible light such as natural light or fluorescent light. Furthermore, it is more preferable when heat is applied in the course of non-fluidizing the compound. Furthermore, it is also acceptable to apply light.

The method for synthesizing the compound having an azomethine part of the present invention is not particularly limited, and any conventionally known synthesis method can be applied. For example, a compound in which in the General Formula (1), $Z_1$ represents N; $Z_2$ represents CH; A represents a 4-hexyloxyphenyl group and B represents a 5-methyl-2-thienyl group, can be synthesized by, for example, the following Scheme 1.

When 4-(hexyloxy)aniline and 5-methylthiophene-2-carboxyaldehyde are heated and stirred to react in ethanol (EtOH), the reaction liquid is filtered, and a powder thus obtained is washed with cold ethanol and is recrystallized from methanol/ethanol, a compound having an azomethine part as a target substance can be obtained (see the following Scheme 1). The temperature at the time heating and stirring is preferably within the range of 0° C. or higher and 100° C. or lower, more preferably within the range of 30° C. or higher and 70° C. or lower, and even more preferably within the range of 40° C. or higher and 60° C. or lower.

Scheme 1

[Chemical Formula 14]

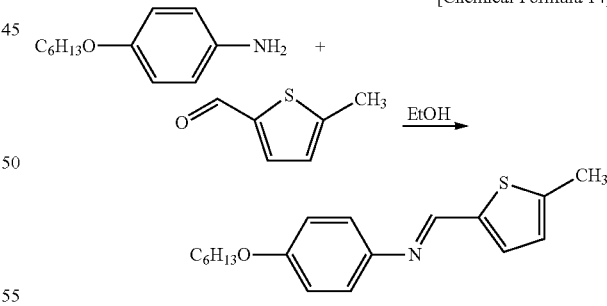

Furthermore, for example, a compound in which in the General Formula (1), $Z_1$ represents CH; $Z_2$ represents N; A represents a 4-N,N'-dipropylaminophenyl group; and B represents an N-methyl-2-pyrrolyl group, can be synthesized by, for example, the following Scheme 2.

When 4-N,N'-dipropylaminobenzaldehyde and N-methyl-pyrrole-2-amine are heated and stirred to react in ethanol (EtOH), the reaction liquid is filtered, and a powder thus obtained is washed with cold ethanol and is recrystallized from methanol/ethanol, a compound having an azomethine part as a target substance can be obtained (see the following Scheme 2). The temperature at the time of heating and stirring is preferably within the range of 0° C. or higher and 100° C. or lower, more preferably within the range of 30° C. or higher and 70° C. or lower, and even more preferably within the range of 40° C. or higher and 60° C. or lower.

Scheme 2

[Chemical Formula 15]

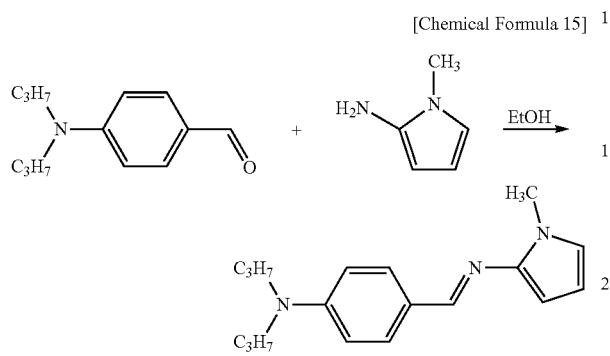

Furthermore, for example, a compound in which in the General Formula (1), $Z_1$ represents N; $Z_2$ represents CH; A represents a 4-hexyloxyphenyl group; and B represents an N-methyl-2-pyrrolyl group, can be synthesized by, for example, the following Scheme 3. Furthermore, for example, even compounds obtained by substituting $Z_1$ and $Z_2$ of this compound can also be synthesized as appropriate by referring to the above-described Scheme 2 and the following Scheme 3.

When 4-(hexyloxy)aniline and N-methyl-pyrrole-2-carboxyaldehyde are heated and stirred to react in ethanol (EtOH), the reaction liquid is filtered, and a powder thus obtained is washed with cold ethanol and is recrystallized from methanol/ethanol, a compound having an azomethine part as a target substance can be obtained (see the following Scheme 3). The temperature at the time of heating and stirring is preferably within the range of 0° C. or higher and 100° C. or lower, more preferably within the range of 30° C. or higher and 70° C. or lower, and even more preferably within the range of 40° C. or higher and 60° C. or lower.

Scheme 3

[Chemical Formula 16]

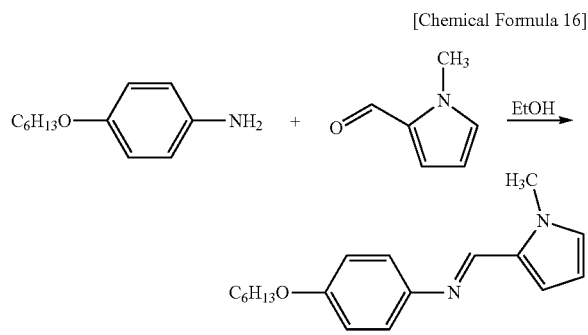

Compounds having an azomethine part, which are other than those described above, can also be synthesized by a similar method by changing the raw materials as appropriate by referring to Schemes 1 to 3.

The compounds having an azomethine part of the present invention can be used singly or in combination of two or more kinds thereof.

[Configuration of Toner]

The present invention also provides a toner containing the compound of the present invention. An embodiment of the present invention is a toner containing the compound according to the above-described first embodiment of the present invention or the compound according to the above-described second embodiment of the present invention.

The toner of the present invention contains the compound having an azomethine part, which is reversibly fluidized and non-fluidized by being irradiated with light as described above. By introducing the compound having an azomethine part into the toner, a toner that can be fixed by light irradiation and has high color reproducibility can be obtained.

Meanwhile, a toner refers to toner base particles or aggregates of toner particles. Toner particles are preferably particles obtained by adding an external additive to toner base particles; however, toner base particles can also be used directly as toner particles. Meanwhile, according to the present invention, in a case in which it is not particularly necessary to distinguish between the toner base particles, the toner particles, and the toner, simply the term "toner" is used.

The content of the compound having an azomethine part is not particularly limited. According to the first embodiment, the content of the compound having an azomethine part depends on the compound species or the resin species; however, from the viewpoints of fixability and color reproducibility, preferably, the content may be in the range of the compound having an azomethine part:binder resin=5:95 to 95:5 (mass ratio). However, a range of 10:90 to 90:10 (mass ratio) is more preferable, a range of 10:90 to 80:20 (mass ratio) is even more preferable, a range of 10:90 to 70:30 (mass ratio) is preferable above all, and a range of 10:90 to 60:40 (mass ratio) is particularly preferable.

<Binder Resin>

It is preferable that the toner of the present invention further contains a binder resin in addition to the compound having an azomethine part. It is generally known that toner particles having approximately uniform particle size and shape can be produced by utilizing the emulsion aggregation method that will be described below, as a method for producing a toner. It is possible to produce a toner only by using the compound having an azomethine part alone or by adding a colorant and a release agent thereto as other additives, without using a binder resin. By using the compound having an azomethine part and a binder resin in combination, production of toner particles having approximately uniform particle size and shape can be carried out using salting-out in an emulsion aggregation method. Therefore, a toner containing the compound having an azomethine part and a binder resin can be applied more easily to a toner for electrophotography.

Regarding such a binder resin, any resin which is generally used as a binder resin that constitutes a toner, can be used without limitations. Specifically, examples include a styrene resin, an acrylic resin, a styrene-acrylic resin, a polyester resin, a silicone resin, an olefin resin, an amide resin, an epoxy resin, and the like. These binder resins can be used singly or in combination of two or more kinds thereof.

Among these, from the viewpoint of having low viscosity when melted, and having high sharp-meltability, it is preferable that the binder resin includes at least one selected from the group consisting of a styrene resin, an acrylic resin, a styrene-acrylic resin, and a polyester resin; and it is more preferable that the binder resin includes at least one selected from the group consisting of a styrene-acrylic resin and a polyester resin.

In the following description, a styrene-acrylic resin and a polyester resin, which are preferred binder resins, will be described.

(Styrene-Acrylic Resin)

A styrene-acrylic resin as used in the present invention is formed by performing polymerization using at least a styrene monomer and a (meth)acrylic acid ester monomer. Here, the styrene monomer includes styrene represented by the structural formula of $CH_2=CH-C_6H_5$, as well as a monomer having a structure having a known side chain or functional group in the styrene structure.

Furthermore, a (meth)acrylic acid ester monomer is a monomer having a functional group having an ester bond in a side chain. Specifically, a vinyl-based ester compound such as an acrylic acid ester monomer represented by $CH_2=CHCOOR$ (wherein R represents an alkyl group), as well as a methacrylic acid ester monomer represented by $CH_2=C(CH_3)COOR$ (wherein R represents an alkyl group) are included.

Specific examples of the styrene monomer and the (meth)acrylic acid ester monomer, which are capable of forming a styrene-acrylic resin, will be shown below; however, the examples are not limited to those shown below.

Examples of the styrene monomer include styrene, o-methylstyrene, m-methylstyrene, p-methylstyrene, x-methylstyrene, p-phenylstyrene, p-ethylstyrene, 2,4-dimethylstyrene, p-t-butylstyrene, p-n-hexylstyrene, p-n-octylstyrene, p-n-nonylstyrene, p-n-decylstyrene, p-n-dodecylstyrene, and the like.

Furthermore, representative examples of the (meth)acrylic acid ester monomer are the acrylic acid ester monomer and methacrylic acid ester monomer shown below, and examples of the acrylic acid ester monomer include methyl acrylate, ethyl acrylate, n-propyl acrylate, isopropyl acrylate, n-butyl acrylate, isobutyl acrylate, t-butyl acrylate, n-octyl acrylate, 2-ethylhexyl acrylate, stearyl acrylate, lauryl acrylate, phenyl acrylate phenyl, and the like. Examples of the methacrylic acid ester monomer include methyl methacrylate, ethyl methacrylate, n-propyl methacrylate, isopropyl methacrylate, n-butyl methacrylate, isobutyl methacrylate, t-butyl methacrylate, n-octyl methacrylate, 2-ethylhexyl methacrylate, stearyl methacrylate, lauryl methacrylate, phenyl methacrylate, diethylaminoethyl methacrylate, dimethylaminoethyl methacrylate, and the like.

These styrene monomers, acrylic acid ester monomers, or methacrylic acid ester monomers can be used singly or in combination of two or more kinds thereof.

Furthermore, regarding the styrene-acrylic copolymer, in addition to the above-described copolymer formed from a styrene monomer and a (meth)acrylic acid ester monomer only, there is also a copolymer formed by using a general vinyl monomer in combination with these styrene monomer and the (meth)acrylic acid ester monomer. Examples of the vinyl monomer that can be used in combination when the styrene-acrylic copolymer as used in the present invention is formed will be given below; however, the vinyl monomers that can be used in combination are not limited to those shown below.

(1) Olefins

Ethylene, propylene, isobutylene, and the like.

(2) Vinyl esters

Vinyl propionate, vinyl acetate, vinyl benzoate, and the like.

(3) Vinyl ethers

Vinyl methyl ether, vinyl ethyl ether, and the like.

(4) Vinyl ketones

Vinyl methyl ketone, vinyl ethyl ketone, vinyl hexyl ketone, and the like.

(5) N-vinyl compounds

N-vinylcarbazole, N-vinylindole, N-vinylpyrrolidone, and the like.

(6) Others

Vinyl compounds such as vinylnaphthalene and vinylpyridine; acrylic acid or methacrylic acid derivatives such as acrylonitrile, methacrylonitrile, and acrylamide; and the like.

Furthermore, it is possible to produce a resin having a crosslinked structure using a polyfunctional vinyl monomer. In addition, it is also possible to use a vinyl monomer having an ionically dissociative group in a side chain. Specific examples of the ionically dissociative group include, for example, a carboxyl group, a sulfonic acid group, a phosphoric acid group, and the like. Specific examples of these vinyl monomers having ionically dissociative groups will be shown below.

Specific examples of a vinyl monomer having a carboxyl group include, for example, acrylic acid, methacrylic acid, maleic acid, itaconic acid, cinnamic acid, fumaric acid, a maleic acid monoalkyl ester, an itaconic acid monoalkyl ester, and the like.

The method for forming a styrene-acrylic resin is not particularly limited, and a method of polymerizing monomers using a known oil-soluble or water-soluble polymerization initiator may be mentioned. If necessary, for example, a known chain transfer agent such as n-octylmercaptan may also be used.

In the case of forming a styrene-acrylic resin to be used for the present invention, the contents of the styrene monomer and the (meth)acrylic acid ester monomer are not particularly limited, and it is possible to adjust the contents as appropriate from the viewpoint of controlling the softening temperature or glass transition temperature of the binder resin. Specifically, the content of the styrene monomer is preferably 40% to 95% by mass, and more preferably 50% to 90% by mass, with respect to the entire monomers which constitute the styrene-acrylic resin. Furthermore, the content of the (meth)acrylic acid ester monomer is preferably 5% to 60% by mass, and more preferably 10% to 50% by mass, with respect to the entire monomers which constitute the styrene-acrylic resin.

The method for forming a styrene-acrylic resin is not particularly limited, and a method of polymerizing monomers using a known oil-soluble or water-soluble polymerization initiator may be mentioned. Examples of an oil-soluble polymerization initiator include, specifically, an azo-based or diazo-based polymerization initiator, and a peroxide-based polymerization initiator shown below.

Examples of the azo-based or diazo-based polymerization initiator include 2,2'-azobis-(2,4-dimethylvaleronitrile), 2,2'-azobisisobutyronitrile, 1,1'-azobis(cyclohexane-1-carbonitrile), 2,2'-azobis-4-methoxy-2,4-dimethylvaleronitrile, azobisisobutyronitrile, and the like.

Examples of the peroxide-based polymerization initiator include benzoyl peroxide, methyl ethyl ketone peroxide, diisopropyl peroxycarbonate, cumene hydroperoxide, t-butyl hydroperoxide, di-t-butyl peroxide, dicumyl peroxide, 2,4-dichlorobenzoyl peroxide, lauroyl peroxide, 2,2-bis-(4,4-t-butylperoxycyclohexyl)propane, tris(t-butylperoxy)triazine, and the like.

Furthermore, in the case of forming styrene-acrylic resin particles by an emulsion polymerization method, a water-soluble radical polymerization initiator can be used. Examples of the water-soluble radical polymerization initiator include persulfuric acid salts such as potassium persulfate and ammonium persulfate; azobisaminodipropane acetate, azobiscyanovaleric acid and salts thereof, hydrogen peroxide, and the like.

The polymerization temperature may vary depending on the type of the monomers or polymerization initiators to be used; however, the polymerization temperature is preferably 50° C. to 100° C., and more preferably 55° C. to 90° C. Furthermore, the polymerization time may vary depending on the type of the monomers or polymerization initiator to be used; however, for example, the polymerization time is preferably 2 to 12 hours.

The styrene-acrylic resin particles to be formed by an emulsion polymerization method can be configured to have two or more layers formed from resins of different compositions. Regarding the production method in this case, a multi-stage polymerization method of adding a polymerization initiator and polymerizable monomers to a dispersion of resin particles prepared by an emulsion polymerization treatment (first stage polymerization) according to a conventional method, and subjecting this system to a polymerization treatment (second stage polymerization) can be employed.

(Polyester Resin)

A polyester resin is a known polyester resin obtainable by a polycondensation reaction between a divalent or higher-valent carboxylic acid (polyvalent carboxylic acid component) and a dihydric or higher-hydric alcohol (polyhydric alcohol component). Meanwhile, the polyester resin may be amorphous or may be crystalline.

The valences of the polyvalent carboxylic acid component and the polyhydric alcohol component are preferably respectively 2 or 3, and particularly preferably respectively 2. Therefore, a case in which the valences are respectively 2 (that is, a dicarboxylic acid component and a diol component) will be described as a particularly preferred embodiment.

Examples of the dicarboxylic acid component include saturated aliphatic dicarboxylic acids such as oxalic acid, malonic acid, succinic acid, glutaric acid, adipic acid, pimelic acid, suberic acid, azelaic acid, sebacic acid, 1,9-nonanedicarboxylic acid, 1,10-decanedicarboxylic acid (dodecanoic acid), 1,11-undecanedicarboxylic acid, 1,12-dodecanedicarboxylic acid, 1,13-tridecanedicarboxylic acid, 1,14-tetradecanedicathoxylic acid, 1,16-hexadecanedicarboxylic acid, and 1,18-octadecanedicarboxylic acid; unsaturated aliphatic dicarboxylic acids such as methylenesuccinic acid, fumaric acid, maleic acid, 3-hexenedioic acid, 3-octenedioic acid, and dodecenylsuccinic acid; unsaturated aromatic dicarboxylic acids such as phthalic acid, terephthalic acid, isophthalic acid, t-butylisophthalic acid, tetrachlorophthalic acid, chlorophthalic acid, nitrophthalic acid, p-phenylene-2-acetic acid, 2,6-naphthalenedicarboxylic acid, 4,4'-biphenyldicarboxylic acid, and anthracenedicarboxylic acid; and the like. Furthermore, lower alkyl esters and acid anhydrides of these can also be used. The dicarboxylic acid components may be used singly or as mixtures of two or more kinds thereof.

In addition to those, polyvalent carboxylic acids having a valence of 3 or higher, such as trimellitic acid and pyromellitic acid; anhydrides or alkyl esters having 1 to 3 carbon atoms of the carboxylic acid compounds described above, and the like can also be used.

Examples of the diol component include saturated aliphatic diols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol, 1,14-tetradecanediol, 1,18-octadecanediol, 1,20-eicosanediol, and neopentyl glycol; unsaturated aliphatic diols such as 2-butene-1,4-diol, 3-butene-1,4-diol, 2-butyne-1,4-diol, 3-butyne-1,4-diol, and 9-octadecene-7, 12-diol; and aromatic diols, such as bisphenols such as bisphenol A and bisphenol F, and alkylene oxide adducts of bisphenols, such as ethylene oxide adducts and propylene oxide adducts of these bisphenols. Furthermore, derivatives thereof can also be used. The diol components may be used singly or as mixtures of two or more kinds thereof.

The method for producing a polyester resin is not particularly limited, and the polyester resin can be produced by polycondensing (esterifying) the above-described polyvalent carboxylic acid component and polyhydric alcohol component by utilizing a known esterification catalyst.

Examples of a catalyst that can be used at the time of producing a polyester resin include alkali metal compounds of sodium, lithium, and the like; compounds containing Group 2 elements such as magnesium and calcium; compounds of metals such as aluminum, zinc, manganese, antimony, titanium, tin, zirconium, and germanium; phosphorous acid compounds; phosphoric acid compounds; amine compounds; and the like. Specifically, examples of tin compounds include dibutyltin oxide, tin octoate, tin dioctoate, salts thereof, and the like. Examples of titanium compounds include titanium alkoxides such as tetra-normal-butyl titanate (Ti(O-n-Bu)$_4$), tetraisopropyl titanate, tetramethyl titanate, and tetrastearyl titanate; titanium acylates such as polyhydroxytitanium stearate; titanium chelates such as titanium tetraacetylacetonate, titanium lactate, and titanium triethanolaminate; and the like. Examples of germanium compounds include germanium dioxide and the like. Furthermore, examples of aluminum compounds include polyaluminum hydroxide, aluminum alkoxide, tributyl aluminate, and the like. These may be used singly or in combination of two or more kinds thereof.

The polymerization temperature is not particularly limited; however, the polymerization temperature is preferably 70° C. to 250° C. Furthermore, the polymerization time is also not particularly limited; however, the polymerization time is preferably 0.5 to 10 hours. During polymerization, the pressure inside the reaction system may be reduced as necessary.

The content proportion in a case in which the toner of the present invention contains a binder resin is not particularly limited.

For example, in the first embodiment, the content proportion in a case in which the toner of the present invention contains a binder resin may be in the range of the compound having an azomethine part:binder resin=5:95 to 95:5 (mass ratio); however, a range of 10:90 to 90:10 (mass ratio) is preferable, a range of 10:90 to 80:20 (mass ratio) is more preferable, a range of 10:90 to 70:30 (mass ratio) is even more preferable, and a range of 10:90 to 60:40 (mass ratio) is particularly preferable. When the content proportion is in this range, photo-induced phase transition of the compound having an azomethine part is likely to occur, and the softening rate based on the irradiation of the toner with light becomes sufficient.

For example, in the second embodiment, in a case in which the toner of the present invention contains a binder resin, the content of the compound having an azomethine part may vary depending on the compound species or the resin species; however, from the viewpoints of fixability and color reproducibility, the content is preferably in the range of the compound having an azomethine part:binder resin=5: 95 to 95:5 (mass ratio). A range of 10:90 to 90:10 (mass ratio) is more preferable, a range of 10:90 to 80:20 (mass ratio) is even more preferable, and a range of 10:90 to 70:30 (mass ratio) is still more preferable. When the content is in this range, photo-induced phase transition of the compound having an azomethine part is likely to occur, and the softening rate based on the irradiation of the toner with light becomes sufficient. Meanwhile, in the case of using two or more kinds of compounds having an azomethine part, it is preferable that the total amount is in the above-described range. In the case of using two or more kinds of binder resins, it is preferable that the total amount is in the above-described range.

Meanwhile, the toner containing the compound having an azomethine part and a binder resin may have a single-layer structure or may have a core-shell structure. The types of the binder resins used in the core particles and the shell portion of the core-shell structure are not particularly limited.

<Colorant>

It is preferable that the toner of the present invention further contains a colorant. It is thought that the compound having an azomethine part according to the first embodiment is colorless and can induce a reversible fluidization and non-fluidization phenomenon concomitantly with isomerization. It is thought that the predetermined compound having an azomethine part according to the second embodiment does not undergo noticeable coloration and can induce a fluidization and reversible non-fluidization phenomenon concomitantly with isomerization. Therefore, by introducing a desired colorant together with these compounds having an azomethine part into a toner, a toner that can be fixed by being irradiated with light and has high color reproducibility of the added colorant can be obtained. Regarding the colorant, generally known dyes and pigments can be used.

Examples of a colorant for obtaining a black toner include carbon black, a magnetic body, iron-titanium composite oxide black, and the like, and examples of the carbon black include channel black, furnace black, acetylene black, thermal black, lamp black, and the like. Furthermore, examples of the magnetic body include ferrite, magnetite, and the like.

Examples of a colorant for obtaining a yellow toner include dyes such as C.I. Solvent Yellow 19, C.I. Solvent Yellow 44, C.I. Solvent Yellow 77, C.I. Solvent Yellow 79, C.I. Solvent Yellow 81, C.I. Solvent Yellow 82, C.I. Solvent Yellow 93, C.I. Solvent Yellow 98, C.I. Solvent Yellow 103, C.I. Solvent Yellow 104, C.I. Solvent Yellow 112, and C.I. Solvent Yellow 162; and pigments such as C.I. Pigment Yellow 14, C.I. Pigment Yellow 17, C.I. Pigment Yellow 74, C.I. Pigment Yellow 93, C.I. Pigment Yellow 94, C.I. Pigment Yellow 138, C.I. Pigment Yellow 155, C.I. Pigment Yellow 180, and C.I. Pigment Yellow 185.

Examples of a colorant for obtaining a magenta toner include dyes such as C.I. Solvent Red 1, C.I. Solvent Red 49, C.I. Solvent Red 52, C.I. Solvent Red 58, C.I. Solvent Red 63, C.I. Solvent Red 111, and C.I. Solvent Red 122; and pigments such as C.I. Pigment Red 5, C.I. Pigment Red 48:1, C.I. Pigment Red 53:1, C.I. Pigment Red 57:1, C.I. Pigment Red 122, C.I. Pigment Red 139, C.I. Pigment Red 144, C.I. Pigment Red 149, C.I. Pigment Red 166, C.I. Pigment Red 177, C.I. Pigment Red 178, and C.I. Pigment Red 222.

Examples of a colorant for obtaining a cyan toner include dyes such as C.I. Solvent Blue 25, C.I. Solvent Blue 36, C.I. Solvent Blue 60, C.I. Solvent Blue 70, C.I. Solvent Blue 93, and C.I. Solvent Blue 95; and pigments such as C.I. Pigment Blue 1, C.I. Pigment Blue 7, C.I. Pigment Blue 15, C.I. Pigment Blue 15:3, C.I. Pigment Blue 60, C.I. Pigment Blue 62, C.I. Pigment Blue 66, and C.I. Pigment Blue 76.

The colorants for obtaining the various color toners can be used singly or in combination of two or more kinds thereof for the respective colors.

The content proportion of the colorant is not particularly limited.

In the first embodiment, the content proportion of the colorant is preferably 0.5% to 20% by mass, and more preferably 2% to 10% by mass, in the toner.

In the second embodiment, the content proportion of the colorant is preferably 0.5% to 20% by mass, and more preferably 2% to 10% by mass, in the toner base particles.

<Release Agent>

It is preferable that the toner according to the present invention further contains a release agent. By introducing a release agent together with the compound having an azomethine part into a toner, a toner having superior fixability can be obtained.

The release agent to be used is not particularly limited, and various known waxes can be used. Examples of the waxes include polyolefins such as low-molecular weight polypropylene and polyethylene, or oxidized low-molecular weight polypropylene and polyethylene; paraffin, synthetic ester waxes; and the like. Particularly from the viewpoint of having low melting point and low viscosity, it is preferable to use a synthetic ester wax, and as a synthetic ester wax, it is particularly preferable to use behenyl behenate, glycerin tribehenate, pentaerythritol tetrabehenate, and the like.

The content proportion of the colorant is not particularly limited.

In the first embodiment, the content proportion of the release agent is preferably within the range of 1% to 30% by mass, and more preferably within the range of 3% to 15% by mass, in the toner.

In the second embodiment, the content proportion of the release agent is preferably within the range of 1% to 30% by mass, and more preferably within the range of 3% to 15% by mass, in the toner base particles.

<Charge Control Agent>

The toner according to the present invention may further contain a charge control agent. The charge control agent to be used is not particularly limited as long as it is a substance that can give positive or negative charge as a result of frictional charging and is colorless, and various known positive charge type charge control agents and negative charge type charge control agents can be used.

The content proportion of the charge control agent is not particularly limited.

In the first embodiment, the content proportion of the charge control agent is preferably within the range of 0.01% to 30% by mass, and more preferably within the range of 0.1% to 10% by mass, in the toner.

In the second embodiment, the content proportion of the charge control agent is preferably within the range of 0.01% to 30% by mass, and more preferably within the range of 0.1% to 10% by mass, in the toner base particles.

<External Additives>

In order to improve the fluidity, chargeability, cleanability, and the like of the toner, the toner of the present invention may be configured by adding external additives such as a fluidizing agent and a cleaning aid, which are so-called post-treatment agents, into the toner base particles.

Examples of the external additives include inorganic particles, such as inorganic oxide particles such as silica particles, alumina particles, and titanium oxide particles; inorganic stearic acid compound particles such as aluminum stearate particles and zinc stearate particles; and inorganic titanic acid compound particles such as strontium titanate particles and zinc titanate particles. If necessary, these inorganic particles may be subjected to hydrophobization treatment. These can be used singly or in combination of two or more kinds thereof.

These inorganic particles may be surface-treated using a silane coupling agent, a titanium coupling agent, a higher fatty acid, a silicone oil, or the like, in order to enhance heat-resistant storability an environmental stability.

Among these, regarding the external additives, for example, sol-gel silica particles, silica particles having hydrophobization-treated surface (hydrophobic silica particles), or titanium oxide particles having hydrophobization-treated surface (hydrophobic titanium oxide particles) are preferred, and among these, it is more preferable to use at least two or more kinds of external additives.

The number average primary particle size of the external additives is preferably within the range of 1 to 200 nm, and more preferably 10 to 180 nm.

The amount of addition of the external additives is not particularly limited.

The amount of addition of these external additives is preferably 0.05% to 5% by mass, and more preferably 0.1% to 3% by mass, in the toner.

<Average Particle Size of Toner>

The average particle size of the toner is preferably 4 to 10 μm, and more preferably 6 to 9 μm, as a volume-based median diameter (D50). When the volume-based median diameter (D50) is in the above-described range, the transfer efficiency is increased, the half-tone image quality is enhanced, and the image quality of fine lines, dots, and the like is enhanced.

According to the present invention, the volume-based median diameter (D50) of the toner is measured and calculated using a measuring apparatus in which a computer system mounted with a software program for data processing "Software V3.51" (manufactured by Beckman Coulter, Inc.) is connected to "Coulter Counter 3" (manufactured by Beckman Coulter, Inc.).

Specifically, 0.02 g of a measurement sample (toner) is added to 20 mL of a surfactant solution (a surfactant solution obtained by diluting, for example, a neutral detergent including a surfactant component 10 times with pure water, for the purpose of dispersing toner particles) and then mixed thoroughly, subsequently ultrasonic dispersing is performed for one minute, and a toner dispersion is prepared. This toner dispersion is injected with a pipette into a beaker containing "ISOTONII" (manufactured by Beckman Coulter, Inc.) in a sample stand, until the displayed concentration of the measuring apparatus reaches 8%.

Here, by adjusting to this concentration range, measured values that are reproducible can be obtained. Then, for the measuring apparatus, the measurement particle count is set to 25,000, and the aperture diameter to 50 μm, and the frequency values for a measurement range of 1 to 30 μm partitioned into 256 segments are calculated. The particle size of 50% from the larger portions of the volume cumulative fraction is designated as the volume-based median diameter (D50).

[Method for Producing Toner]

The method for producing the toner of the present invention is not particularly limited. For example, in a case in which a toner that contains the compound having an azomethine part and does not contain a binder resin is produced, a production method including pulverizing the compound having an azomethine part obtained by the synthesis method described above, and as necessary, additives, using an apparatus such as a hammer mill, a feather mill, or a counter jet mill, and then classifying the resultant to have a desired particle size using a dry classifier such as a spin air sieve, a Classiel, or a Microclassifier, is preferred.

In a case in which a toner that contains the compound having an azomethine part and additives such as a colorant and does not contain a binder resin is produced, a production method including dissolving the compound having an azomethine part and the additives such as a colorant into a solution using a solvent that dissolves the compound having an azomethine part and the additives such as a colorant together, subsequently removing the solvent, and then performing pulverization and classification by a method similar to the method described above, is more preferred.

In the case of producing a toner containing the compound having an azomethine part, a binder resin, and additives such as a colorant, a production method utilizing an emulsion aggregation method, with which the control of the particle size and the shape is easy, is preferred.

It is preferable that such a production method includes steps of:

(1A) a binder resin particle dispersion preparation step of preparing a dispersion of binder resin particles;

(1B) a colorant particle dispersion preparation step of preparing a dispersion of colorant particles;

(1C) an azomethine part-containing compound particle dispersion preparation step of preparing a dispersion of azomethine part-containing compound particles;

(2) an association step of adding an aggregating agent into a water-based medium in which the binder resin particles, the colorant particles, and the azomethine part-containing compound particles are present, performing aggregation and fusion simultaneously with salting-out, and forming associated particles;

(3) an aging step of controlling the shape of the associated particles and thereby forming toner particles (toner base particles);

(4) a filtration and cleaning step of separating the toner particles (toner base particles) by filtration from the water-based medium and removing a surfactant and the like from the toner particles (toner base particles);

(5) a drying step of drying the cleaning-treated toner particles (toner base particles); and (6) an external additive addition step of adding external additives to the drying-treated toner particles (toner base particles). In the following description, the steps of (1A) to (1C) will be described.

(1A) Binder Resin Particle Dispersion Preparation Step

In the present step, resin particles are formed by conventionally known emulsion polymerization or the like, and these resin particles are aggregated and fused to form binder resin particles. As an example, polymerizable monomers that constitute a binder resin are introduced into a water-based medium and dispersed therein, these polymerizable monomers are polymerized using a polymerization initiator, and a dispersion of binder resin particles is produced.

Furthermore, as a method of obtaining a binder resin particle dispersion, in addition to the above-described method of polymerizing polymerizable monomers using a polymerization initiator in a water-based medium, for example, a method of performing a dispersion treatment in an aqueous medium without using a solvent; a method of dissolving a binder resin (crystalline resin or the like) in a solvent such as ethyl acetate to obtain a solution, emulsion dispersing the solution in an aqueous medium using a dispersing machine, and then performing a solvent removal treatment; or the like may be mentioned.

At this time, a release agent (wax) may be incorporated in advance in the binder resin, as necessary. Furthermore, for the dispersing, it is also preferable to perform polymerization in the presence of a known surfactant (for example, an anionic surfactant such as sodium polyoxyethylene (2) dodecyl ether sulfate, sodium dodecyl sulfate, or dodecyl benzenesulfonate) as appropriate. Meanwhile, apart from the binder resin particle dispersion, it is also acceptable that a release agent particle dispersion is prepared in the same manner as the colorant particle dispersion preparation step, and the release agent particle dispersion is incorporated in the water-based medium of the association step of the (2).

The volume-based median diameter of the binder resin particles in the dispersion is preferably 50 to 300 nm. The volume-based median diameter of the binder resin particles in the dispersion can be measured by a dynamic light scattering method using a "MICROTRAC UPA-150" (manufactured by Nikkiso Co., Ltd.).

(1B) Colorant Particle Dispersion Preparation Step

This colorant particle dispersion preparation step is a step of preparing a dispersion of colorant particles by dispersing a colorant in a microparticulate form in a water-based medium.

Dispersing of the colorant can be carried out by utilizing mechanical energy. The number-based median diameter of the colorant particles in the dispersion is preferably 10 to 300 nm, and more preferably 50 to 200 nm. The number-based median diameter of the colorant particles can be measured using an electrophoretic light scattering photometer "ELS-800" (manufactured by Otsuka Electronics Co., Ltd.).

(1C) Azomethine Part-Containing Compound Particle Dispersion Preparation Step

This azomethine part-containing compound particle dispersion preparation step is a step of dispersing a compound having an azomethine part in a microparticulate form in a water-based medium and thereby preparing a dispersion of particles of the compound having an azomethine part. On the occasion of preparing the azomethine part-containing compound particle dispersion, first, an emulsion of the compound having an azomethine part is prepared. Regarding the method for preparing an emulsion of the compound having an azomethine part, for example, a method of obtaining an azomethine part-containing compound solution in which the compound having an azomethine part is dissolved in an organic solvent, and then emulsifying the azomethine part-containing compound solution in a water-based medium, may be mentioned.

The method of dissolving a compound having an azomethine part in an organic solvent is not particularly limited, and for example, there is a method of adding a compound having an azomethine part in an organic solvent and then stirring and mixing so that the compound having an azomethine part dissolves therein. The proportion of addition of the compound having an azomethine part is preferably 5 parts by mass or more and 100 parts by mass or less, and more preferably 10 parts by mass or more and 50 parts by mass or less, with respect to 100 parts by mass of the organic solvent.

Next, the azomethine part-containing compound solution and the water-based medium are mixed, and the mixture is stirred using a known dispersing machine such as a homogenizer. Thereby, the compound having an azomethine part becomes liquid droplets, the liquid droplets are emulsified in a water-based medium, and thus an emulsion of the compound having an azomethine part is prepared.

The proportion of addition of the azomethine part-containing compound solution is preferably 10 parts by mass or more and 110 parts by mass or less with respect to 100 parts by mass of the water-based medium.

Furthermore, at the time of mixing the azomethine part-containing compound solution and the water-based medium, the respective temperatures of the azomethine part-containing compound solution and the water-based medium are in a temperature range of below the boiling point of the organic solvent, preferably 20° C. or higher and 80° C. or lower, and more preferably 30° C. or higher and 75° C. or lower. At the time of mixing the azomethine part-containing compound solution and the water-based medium, the temperature of the azomethine part-containing compound solution and the temperature of the water-based medium may be identical to each other or different from each other, and preferably, the temperatures are identical to each other.

Regarding the stirring conditions for the dispersing machine, for example, in a case in which the capacity is 1 to 3 L, the speed of rotation is preferably 7,000 rpm or more and 20,000 rpm or less, and the stirring time is preferably 10 minutes or more and 30 minutes or less.

The azomethine part-containing compound particle dispersion is prepared by removing the organic solvent from the emulsion of the compound having an azomethine part. Regarding the method of removing the organic solvent from the emulsion of the compound having an azomethine part, for example, known methods such as air blowing, heating, pressure reduction, or combined use of these may be mentioned.

As an example, when the emulsion of the compound having an azomethine part is heated, for example, in an inert gas atmosphere of nitrogen or the like, preferably at a temperature of 25° C. or higher and 90° C. or lower, and more preferably 30° C. or higher and 80° C. or lower, until about 80% by mass or more and 95% by mass or less of the initial amount of the organic solvent is removed, the organic solvent is removed. In this way, the organic solvent is removed from the water-based medium, and thereby an azomethine part-containing compound particle dispersion in which azomethine part-containing compound particles are dispersed in a water-based medium is prepared.

The mass average particle size of the azomethine part-containing compound particles in the azomethine part-containing compound particle dispersion is preferably 90 nm or more and 1,200 nm or less. The mass average particle size of the azomethine part-containing compound particles can be set to be within the above-described range by regulating the viscosity at the time of incorporating the compound having an azomethine part into the organic solvent, the mixing ratio between the azomethine part-containing compound solution and the water-based medium, the stirring speed of the dispersing machine at the time of preparing an emulsion of the compound having an azomethine part, and the like as appropriate. The mass average particle size of the azomethine part-containing compound particles in the azomethine part-containing compound particle dispersion can be measured using an electrophoretic light scattering photometer "ELS-800" (manufactured by Otsuka Electronics Co., Ltd.).

<Organic Solvent>

Regarding the organic solvent used in the present step, any organic solvent that can dissolve the compound having an azomethine part of the present invention can be used without any particular limitations. Specifically, examples include esters such as ethyl acetate and butyl acetate; ethers such as diethyl ether, diisopropyl ether, and tetrahydrofuran; ketones such as acetone and methyl ethyl ketone; saturated hydrocarbons such as hexane and heptane; and halogenated hydrocarbons such as dichloromethane, dichloroethane, and carbon tetrachloride.

These organic solvents can be used singly or as mixtures of two or more kinds thereof. Among these organic solvents, ketones and halogenated hydrocarbons are preferred, and methyl ethyl ketone and dichloromethane are more preferred.

<Water-Based Medium>

The water-based medium used in the present step may be water, or a water-based medium containing water as a main component, in which a water-soluble solvent such as an alcohol or a glycol, or optional components such as a surfactant and a dispersant are incorporated, for example. Regarding the water-based medium, preferably a mixture of water and a surfactant is used.

Examples of the surfactant include a cationic surfactant, an anionic surfactant, a nonionic surfactant, and the like. Examples of the cationic surfactant include dodecyl ammonium chloride, dodecyl ammonium bromide, dodecyl trimethylammonium bromide, dodecyl pyridinium chloride, dodecyl pyridinium bromide, hexadecyl trimethylammonium bromide, and the like. Examples of the anionic surfactant include fatty acid soaps such as sodium stearate and sodium dodecanoate; sodium dodecyl benzenesulfonate, sodium dodecyl sulfate, and the like. Furthermore, examples of the nonionic surfactant include polyoxyethylene dodecyl ether, polyoxyethylene hexadecyl ether, polyoxyethylene nonyl phenyl ether, polyoxyethylene lauryl ether, polyoxyethylene sorbitan monooleate ether, monodecanoyl sucrose, and the like.

These surfactants can be used singly or in combination of two or more kinds thereof. Among the surfactants, preferably an anionic surfactant, and more preferably sodium dodecyl benzenesulfonate is used.

The amount of addition of the surfactant is preferably 0.01 parts by mass or more and 10 parts by mass or less, and more preferably 0.04 parts by mass or more and 1 part by mass or less, with respect to 100 parts by mass of the water-based medium.

The steps from the (2) association step to the (6) external additive addition step can be carried out according to various conventionally known methods.

Meanwhile, the aggregating agent used in the (2) association step is not particularly limited; however, an aggregating agent selected from metal salts is suitably used. Examples of the metal salts include monovalent metal salts such as salts of alkali metals such as sodium, potassium, and lithium; divalent metal salts of calcium, magnesium, manganese, copper, and the like; trivalent metal salts of iron and aluminum, and the like; and the like. Specific examples of the metal salts include sodium chloride, potassium chloride, lithium chloride, calcium chloride, magnesium chloride, zinc chloride, copper sulfate, magnesium sulfate, manganese sulfate, and the like, and among these, from the viewpoint that aggregation can be carried out with a smaller amount, it is particularly preferable to use a divalent metal salt. These can be used singly or in combination of two or more kinds thereof.

[Developer]

Regarding the toner of the present invention, for example, a case in which a magnetic body is incorporated, and the toner is used as a one-component magnetic toner; a case in which the toner is mixed with a so-called carrier, and the toner is used as a two-component developer; a case in which a non-magnetic toner is used alone; and the like can be considered, and all can be suitably used.

Regarding the magnetic body, for example, magnetite, γ-hematite, various ferrites, or the like, can be used.

Regarding the carrier that constitutes a two-component developer, magnetic particles formed from conventionally known materials including metals such as iron, steel, nickel, cobalt, ferrite, and magnetite; alloys of those metals with metals such as aluminum and lead; and the like, can be used.

Regarding the carrier, it is preferable to use a coated carrier obtained by coating the surface of magnetic particles with a coating agent such as a resin, or a so-called resin-dispersed type carrier formed by dispersing a magnetic powder in a binder resin. The resin for coating is not particularly limited; however, for example, an olefin resin, a styrene resin, a styrene-acrylic resin, a silicone resin, a polyester resin, a fluororesin, or the like is used.

Furthermore, regarding the resin for constituting the resin-dispersed type carrier, any known resin can be used without particular limitations, and for example, an acrylic resin, a styrene-acrylic resin, a polyester resin, a fluororesin, a phenolic resin, or the like can be used.

The volume-based median diameter of the carrier is preferably 20 to 100 am, and more preferably 25 to 80 μm. The volume based median diameter of the carrier can be measured representatively using a laser diffraction type particle size distribution analyzer "HELOS" (manufactured by Sympatec GmbH) equipped with a wet dispersing machine.

The mixing amount of the toner is preferably 2% to 10% by mass on the basis of the total mass of the toner and the carrier as 100% by mass.

[Image Forming Method]

The toner of the present invention can be used for various known image forming methods of the electrophotographic method. For example, the toner can be used for a monochromatic image forming method or a full-color image forming method. The full-color image forming method can be applied to any image forming method such as a four-cycle system image forming method configured to include four kinds of color developing apparatus respectively related to yellow, magenta, cyan, and black and one photoreceptor; or a tandem system image forming method in which image forming units each having a color developing apparatus related to each color and a photoreceptor are mounted for the respective colors. In the image forming method according to an embodiment of the present invention, it is preferable that a step of forming a toner image formed from a toner containing the compound having an azomethine part on a recording medium; and a step of irradiating the toner image with light and thereby softening the toner image are included. Furthermore, from the viewpoint of sufficiently fluidizing the compound having an azomethine part in the toner and rapidly softening the toner image, the wavelength of light at the time of irradiating the toner image with light is preferably 280 nm or more and 480 nm or less. Furthermore, from the viewpoint of obtaining better fixability, it is preferable that a step of pressing the toner image is further included. From the viewpoint of obtaining even superior fixability, it is preferable that the toner image is further heated in the pressing step.

FIG. 1 is an outline configuration diagram illustrating an image forming apparatus 100 that is used for the image forming method according to an embodiment of the present invention. However, the image forming apparatus used for the present invention is not limited to the following form and the illustrated example. FIG. 1 illustrates an example of a monochromatic image forming apparatus 100; however, the present invention can also be applied to a color image forming apparatus.

The image forming apparatus 100 is an apparatus for forming an image on recording paper S as a recording medium, the apparatus including an image reading apparatus 71 and an automatic document feeder 72 and performs image forming by means of an image forming unit 10, an irradiation unit 40, and a compression unit 9 on the recording paper S that is conveyed by a paper conveyance system 7.

Furthermore, in the image forming apparatus 100, recording paper S is used as a recording medium; however, the medium that is considered as an object to be subjected to image forming may be anything other than paper.

The document d placed on a copy holder of the automatic document feeder 72 is scanned and exposed to light by means of an optical system of a scanning exposure apparatus of the image reading apparatus 71 and is read by an image sensor CCD. An analog signal that has been photoelectrically converted by the image sensor CCD is subjected to analog processing, A/D conversion, shading compensation, image compression processing, and the like in an image processing unit 20, and then is inputted into an exposure device 3 of the image forming unit 10.

The paper conveyance system 7 includes a plurality of trays 16, a plurality of paper feeders 11, conveyance rollers 12, a conveyance belt 13, and the like. The trays 16 accommodate recording papers S of an appointed sizes, and the recording papers S are supplied by operating the paper feeder 11 of a determined tray 16 according to the command from a control unit 90. The conveyance rollers 12 convey the recording paper S that has been sent from the tray 16 by the paper feeder 11 or the recording paper S that has been brought in from a manual paper feeder 15 to the image forming unit 10.

The image forming unit 10 is configured such that a charging device 2, an exposure device 3, a developing unit 4, a transfer unit 5, a discharging unit (not illustrated in the diagram), and a cleaning unit 8 are discharged in sequence around a photoreceptor 1 along the direction of rotation of the photoreceptor 1.

The photoreceptor 1 as an image carrier is an image carrier having a photoconductive layer formed on a surface and is configured to be capable of rotating in the direction of arrow in FIG. 1 by a driving apparatus that is not illustrated in the diagram. Near the photoreceptor 1, a thermometer/hygrometer 17 that detects temperature and humidity inside the image forming apparatus 100 is provided.

The charging device 2 uniformly applies electric charge to the surface of the photoreceptor 1 and evenly electrostatically charges the surface of the photoreceptor 1. The exposure device 3 includes a beam light source such as a laser diode, and the exposure device 3 irradiates the surface of the electrostatically charged photoreceptor 1 with beam light to thereby cause the electric charge of the irradiated portion to be lost, and forms an electrostatic latent image in accordance with the image data on the photoreceptor 1. The developing unit 4 supplies a toner that is accommodated therein to the photoreceptor 1 and produces a toner image based on the electrostatic latent image on the surface of the photoreceptor 1.

The transfer unit 5 faces the photoreceptor 1, with a recording paper S interposed therebetween, and transfers the toner image onto the recording paper S. The discharging unit performs charge removal on the photoreceptor 1 after the toner image is transferred. The cleaning unit 8 includes a blade 85. The surface of the photoreceptor 1 is cleaned by the blade 85, and the developer remaining on the surface of the photoreceptor 1 is removed.

The recording paper S having the toner image transferred thereon is conveyed to a compression unit 9 by a conveyance belt 13. The compression unit 9 is arbitrarily installed, and the compression unit 9 applies a fixing treatment to the recording paper S having the toner image transferred thereon by applying pressure only or applying heat and pressure by means of pressing members 91 and 92 and thereby fixes an image on the recording paper S. The recording paper S having the image fixed thereon is conveyed to a paper ejection unit 14 by conveyance rollers and is discharged out of the machine from the paper ejection unit 14.

Furthermore, the image forming apparatus 100 includes a paper inverting unit 24, and enables conveying the recording paper S that has been subjected to a heating and fixing treatment to the paper inverting unit 24 right before the paper ejection unit 14, inverting the front and back, and discharging the recording paper S, or conveying the recording paper S that has been subjected to inversion of the front and back, again to the image forming unit 10 and performing image formation on both surfaces of the recording paper S.

<Irradiation Unit>

Figure 2:
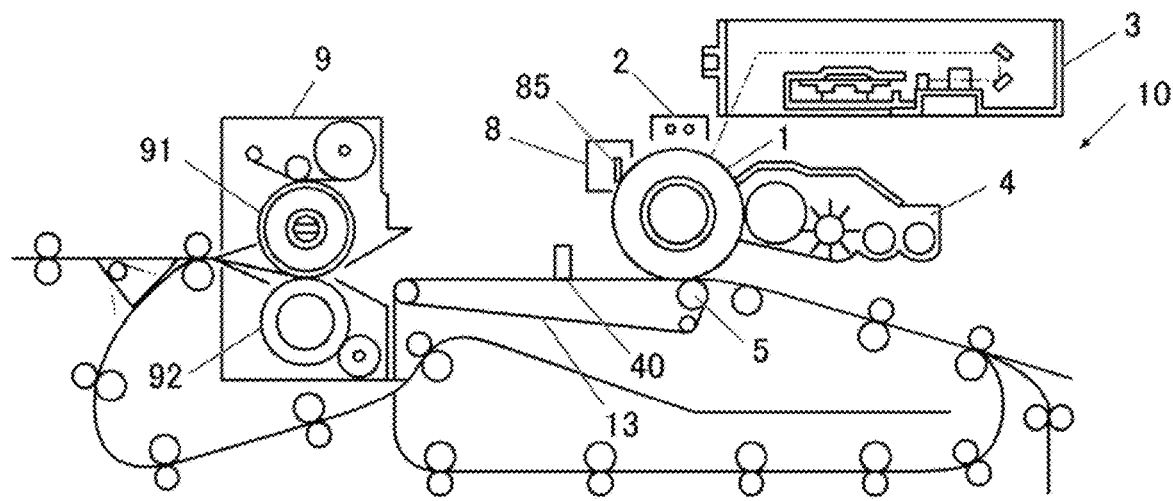
FIG. 2 is an outline configuration diagram of an irradiation unit in the image forming apparatus of FIG. 1.

FIG. 2 is an outline configuration diagram of the irradiation unit 40 in the image forming apparatus 100.

The image forming apparatus 100 according to an embodiment of the present invention includes an irradiation unit 40. Examples of apparatuses that constitute the irradiation unit 40 include a light emitting diode (LED), a laser light source, and the like.

The irradiation unit 40 melts and fluidizes a compound that undergoes phase transition by absorbing light (compound having an azomethine part of the present invention), which is included in the toner of the developer. The wavelength of light to be irradiated may be any wavelength to the extent that can cause sufficient fluidization, and light having a wavelength preferably in the range of 280 nm or more and 480 nm or less, more preferably in the range of 300 nm or more and 420 nm or less, and even more preferably in the range of 330 nm or more and 420 nm or less, is irradiated. The amount of irradiation of light at the irradiation unit 40 may be of the extent that can cause sufficient fluidization, and the amount of irradiation is preferably in the range of 0.1 to 200 J/cm$^2$, more preferably in the range of 0.1 to 100 J/cm$^2$, and even more preferably in the range of 0.1 to 50 J/cm$^2$.

When the compound having an azomethine part is non-fluidized (re-solidified), the compound may be non-fluidized by leaving the compound to stand untouched at room temperature (in the range of 25±15° C.).

That is, an image forming method according to an embodiment of the present invention includes a step of forming a toner image formed from the toner of the present invention on a recording medium; a step of irradiating the toner image with light having a wavelength of 280 nm or more and 480 nm or less and softening the toner image; and a step of leaving the softened toner image to stand at room temperature (in the range of 25±15° C.), thereby solidifying the toner image, and fixing the toner image on a recording medium. Meanwhile, it is preferable that the step of fixing further includes a step of pressing the softened toner image. In the step of pressing, it is preferable that the softened toner image is further heated. It is because the toner image can be further softened by heating.

The heating temperature at the time of further heating in the step of pressing is preferably 30° C. or higher and 100° C. or lower, and more preferably 40° C. or higher and 100° C. or lower.

The irradiation unit 40 radiates light toward a first surface on the photoreceptor side in the recording paper S that retains the toner image, and is disposed on the photoreceptor side with respect to the surface of the recording paper S that is nipped between the photoreceptor 1 and transfer roller 5, which constitute the transfer unit. Furthermore, the irradiation unit 40 is disposed along the direction of conveyance of the recording paper S (paper conveyance direction).

The irradiation unit 40 is disposed on the downstream side in the paper conveyance direction with respect to the position of nipping between the photoreceptor 1 and the transfer roller 5, and on the upstream side in the paper conveyance direction with respect to the compression unit 9.

According to the image forming method according to an embodiment of the present invention, the photoreceptor 1 is electrostatically charged by applying uniform electric charge thereto by a charging device 2, subsequently the photoreceptor 1 is scanned with the light flux radiated by the exposure device 3 based on the original image data, and an electrostatic latent image is formed. Next, a developer having a toner that includes a compound that undergoes phase transition by light absorption (compound having an azomethine part) is supplied onto the photoreceptor 1 by means of the developing unit 4.

When recording paper S is conveyed from the tray 16 to the image forming unit 10 in accordance with the timing at which the toner image supported on the surface of the photoreceptor 1 reaches the position of the transfer roller 5, which constitute the transfer unit, by rotation of the photoreceptor 1, the toner image on the photoreceptor 1 is transferred onto the recording paper S that is nipped between the transfer roller 5 and the photoreceptor 1 by a transfer bias applied to the transfer roller 5.

Furthermore, a transfer unit 5 also functions as a pressing member, and the transfer unit 5 can transfer the toner image from the photoreceptor 1 onto the recording paper S and can reliably adhere the compound having an azomethine part included in the toner image to the recording paper S.

After the toner image is transferred onto the recording paper S, a blade 85 of the cleaning unit 8 removes any developer remaining on the surface of the photoreceptor 1.

In the process in which the recording paper S having the toner image transferred thereon is conveyed to the compression unit 9 by a conveyance belt 13, the irradiation unit 40 irradiates the toner image transferred onto the recording paper S with light having a wavelength of 280 nm or more and 480 nm or less. When ultraviolet light is radiated toward the toner image of the first surface of the recording paper S by the irradiation unit 40, the toner image can be melted more reliably, and the fixability of the toner image to the recording paper S can be enhanced.

When the recording paper S retaining the toner image reaches the compression unit 9 by the conveyance belt 13, the pressing members 91 and 92 compresses the toner image to the first surface of the recording paper S. Since the toner image is softened by ultraviolet light irradiation by the irradiation unit 40 before a fixing treatment is provided by the compression unit 9, energy saving for image compression to the recording paper S can be promoted. It is preferable that the image forming method of the present invention further includes, in the step of solidifying the toner image and fixing the toner image onto the recording medium, a step of pressing the toner image by means of pressing members 91 and 92 while leaving the toner image to stand at room temperature (in the range of 25±15° C.). By applying pressure by the pressing members 91 and 92, the fixability of the toner image to the recording paper S is further enhanced.

The pressure at the time of pressing the toner image on the recording medium is not particularly limited; however, the pressure is preferably 0.01 to 5.0 MPa, and more preferably 0.05 to 1.0 MPa. When the pressure is adjusted to 0.01 MPa or higher, since the amount of deformation of the toner image can be increased, the contact area between the toner image and the recording paper S increases, and the fixability of the image can be increased more easily. Furthermore, when the pressure is adjusted to 5.0 MPa or less, the shock noise at the time of pressing can be suppressed.

Furthermore, in the step of pressing, it is preferable that the toner image is further heated. When pressure and heat are applied by the pressing members 91 and 92, the fixability of the toner image to the recording paper S is further enhanced. Specifically, regarding the pressing member 91, when the recording paper S passes through between the pressing members 91 and 92, the toner image that has been softened by light irradiation is pressed in a further softened state by heating, and thereby the fixability of the toner image to the recording paper S is further enhanced.

Thereafter, the toner image on the recording paper S is solidified in a natural environment (by leaving the toner image to stand at room temperature). Specifically, when the toner image is left in a natural environment (state of being left at room temperature) until the recording paper S that has passed through between the pressing members 91 and 92 reaches the paper ejection unit 14, the toner image on the recording paper S can be coagulated more reliably, and the fixability of the toner image to the recording paper S can be further enhanced.

In a case in which images are formed on both surfaces of the recording paper S, the recording paper S that has been subjected to compression treatment is conveyed to the paper inverting unit 24 right before the paper ejection unit 14 and is discharged after inverting the front and back, or the recording paper S having the front and back inverted is conveyed again to the image forming unit 10.

(Photosensitive Adhesive)

Since the compound of the present invention is reversibly fluidized and non-fluidized by being irradiated with light, a photosensitive adhesive (photoresponsive adhesive) that can be repeatedly utilized can be produced using the compound of the present invention. For example, the photosensitive adhesive can be applied to various adhesion technologies as a photosensitive adhesive that is capable of repeated photodesorption in response to changes in the viscosity (coefficient of friction).

The photosensitive adhesive (photoresponsive adhesive) of the present invention is also suitable for recycling utilization in addition to that the photosensitive adhesive can be used for temporary fixation, by which repeated utilization is enabled; however, the use is not limited to these.

EXAMPLES

First Embodiment

The effects of the first embodiment of the present invention will be described using the following Examples and Comparative Examples. However, the technical scope of the present invention is not intended to be limited to the following Examples only.

The compound having an azomethine part used in Examples 1-1 to 1-41, in which the heterocyclic ring of the Chemical Formula 1 is a thiophene ring, was synthesized by a method similar to the synthesis of compound 1-21 of Table 1-1 used in Example 1-16 described below. The synthesis method of Example 1-16 will be described as a representative example.

Synthesis of Compound Having Azomethine Part

Examples 1-16: Synthesis of Compound 1-21 of Table 1-1

Scheme 1

[Chemical Formula 17]

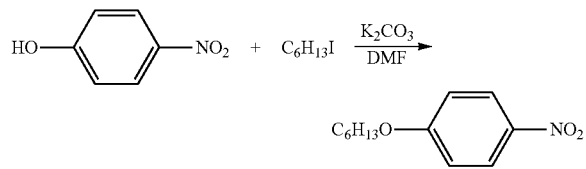

Scheme 2

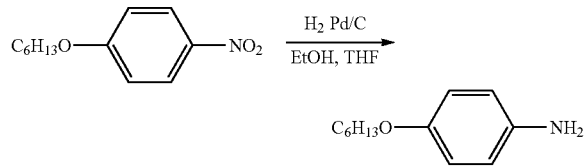

Scheme 3

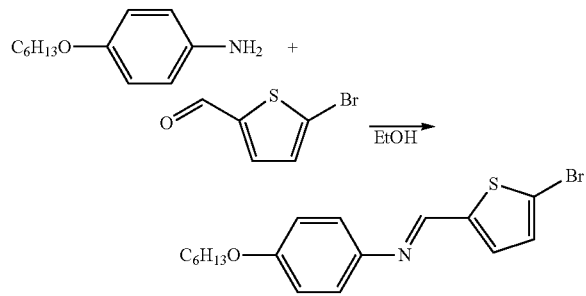

Scheme 1

Into a 100-ml four-necked flask equipped with a cooling tube, a nitrogen inlet tube, and a thermometer, 4-nitrophenol (4.2 g, 30.2 mmol), 1-iodohexane (19.2 g, 90.6 mmol), potassium carbonate (10.4 g, 75.5 mmol), and 50 ml of dimethylformamide were introduced, and the mixture was heated to reflux. The reaction liquid was washed with water and then concentrated, and the resultant was purified by column chromatography (ethyl acetate:heptane=1:9 (volume ratio)). Thus, 5.8 g (yield 86%) of 4-(hexyloxy)nitrobenzene was obtained.

Scheme 2

Into a 500-ml conical flask, 4-(hexyloxy)nitrobenzene (5.8 g, 26.1 mmol) and palladium-carbon (0.12 g, 258 mmol) were introduced, and 60 ml each of ethanol and tetrahydrofuran were introduced therein. The mixture was stirred while hydrogen ($H_2$) was enclosed. Palladium-carbon was removed from the reaction liquid, the solution thus obtained was concentrated, and then recrystallization was performed from ethanol. Thus, 3.8 g (yield 75%) of 4-(hexyloxy)aniline was obtained.

Scheme 3

Into a 100-ml four-necked flask equipped with a cooling tube, a nitrogen inlet tube, and a thermometer, 4-(hexyloxy)aniline (1.1 g, 5.7 mmol), 5-bromothiophene-2-carboxyaldehyde (1.1 g, 5.7 mmol), and 20 ml of ethanol were introduced, and the mixture was heated and stirred at 50° C. The reaction liquid was suction-filtered, and a powder thus obtained was washed with cold ethanol. Furthermore, recrystallization was performed with methanol/ethanol, and 0.85 g (yield 41%) of compound 1-21 as a target substance was obtained.

Production of compound 1-21 was confirmed by $^1$H-NMR. $^1$H NMR (400 MHz, $CDCl_3$); 8.35 ppm (s, 1H, CH=N), 7.71 ppm (d, 2H, aryl), 6.95 ppm (d, 2H, aryl), 6.89 ppm (d, 2H, thiophene), 4.08 ppm (t, 2H, methylene), 1.81 ppm (m, 2H, methylene), 1.45 ppm (m, 2H, methylene), 1.38 ppm (m, 4H, methylene), 0.85 ppm (t, 3H, methyl).

Figure 3A:
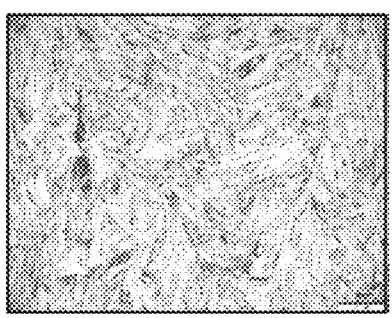
FIGS. 3A, 3B, and 3C are diagrams obtained, in order to check phase transition from a crystalline phase or a liquid crystal phase to an isotropic phase in the first embodiment, by sealing a compound 1-22 of Table 1-1 as a target substance in a glass sandwich cell, irradiating the compound with light at 365 nm under an observation with a polarizing microscope, and observing any change in the state. Among these.
Figure 3B:
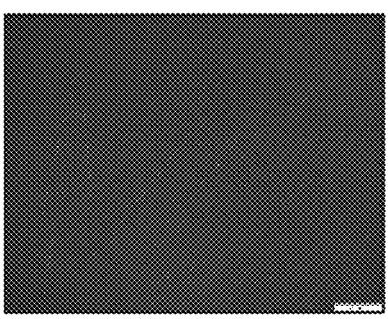
Figure 3C:
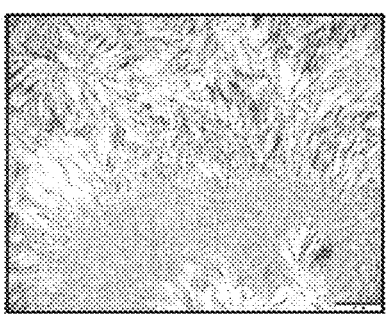

Furthermore, in order to check phase transition from a crystalline phase or a liquid crystal phase to an isotropic phase, polarizing microscopic observation was performed. Target compound 1-21 was sealed in a glass sandwich cell, the compound was irradiated with light at 365 nm under an observation with a polarizing microscope, and changes in the state were observed. FIGS. 3A, 3B, and 3C show photographs of polarizing microscopy of before light irradiation (FIG. 3A), after light irradiation (FIG. 3B), and after stopping of light irradiation (FIG. 3C). Isomerization and reversible phase change from the crystalline phase to the isotropic phase induced by light irradiation could be confirmed.

Other compounds were also synthesized by a similar method using the respective corresponding raw materials, and compounds having an azomethine part (see Table 1-2) of Examples 1-1 to 1-41, in which the heterocyclic ring of the Chemical Formula 1 was a thiophene ring, were obtained.

Examples 1-1 to 1-12: Synthesis of Compounds Having Azomethine Part in which Heterocyclic Ring of the Chemical Formula 1 is Thiophene Ring Compounds 1-1, 1-4 to 1-6, 1-8 to 1-10, and 1-12 to 1-16 of Examples 1-1 to 1-12 were synthesized in the same manner as in the synthesis of compound 1-21, except that 4-nitrophenol (30.2 mmol) was changed to 2-methyl-4-nitrophenol (30 mmol) in the respective Examples, and 5-bromothiophene-2-carboxyaldehyde (5.7 mmol) was changed to 5-hexylthiophene-2-carboxyaldehyde (5.0 mmol) in compound 1-1 of Example 1-1, to 5-propylthiophene-2-carboxyaldehyde (5.8 mmol) in compound 1-4 of Example 1-2, to 5-methylthiophene-2-carboxyaldehyde (5.2 mmol) in compound 1-5 of Example 1-3, to 5-hexyloxythiophene-2-carboxyaldehyde (5.1 mmol) in compound 1-6 of Example 1-4, to 5-hexyloxycarbonylthiophene-2-carboxyaldehyde (5.6 mmol) in compound 1-8 of Example 1-5, to 5-bromothiophene-2-carboxyaldehyde (5.8 mmol) in compound 1-9 of Example 1-6,
to 5-cyanothiophene-2-carboxyaldehyde (5-formylthiophene-2-carbonitrile) (5.1 mmol) in compound 1-10 of Example 1-7,
to 5-methoxythiophene-2-carboxyaldehyde (5.0 mmol) in compound 1-12 of Example 1-8,
to 5-hydroxythiophene-2-carboxyaldehyde (5.3 mmol) in compound 1-13 of Example 1-9,
to 2-thiophenecarboxyaldehyde (5.4 mmol) in compound 1-14 of Example 1-10,
to 5-hexyl-4-methylthiophene-2-carboxyaldehyde (5.4 mmol) in compound 1-15 of Example 1-11, and
to 5-hexyl-3-methylthiophene-2-carboxyaldehyde (5.5 mmol) in compound 1-16 of Example 1-12. Similarly to the compound 1-21, production of the compounds was confirmed by $^1$H-NMR, and it was found that the intended compounds were obtained.

Example 1-13: Synthesis of Compound Having Azomethine Part in which Heterocyclic Ring of Chemical Formula 1 is Thiophene Ring Compound 1-17 of Example 1-13 was synthesized in the same manner as in the synthesis of compound 1-21, except that
4-nitrophenol (30.2 mmol) was changed to 3-methyl-4-nitrophenol (30 mmol), and
5-bromothiophene-2-carboxyaldehyde (5.7 mmol) was changed to 5-hexylthiophene-2-carboxyaldehyde (5.3 mmol). Similarly to the compound 1-21, production of the compound was confirmed by $^1$H-NMR, and it was found that the intended compound was obtained.

Examples 1-14, 1-15, 1-17, and 1-18: Synthesis of Compounds Having Azomethine Part in which Heterocyclic Ring of Chemical Formula 1 is Thiophene Ring Compounds 1-19, 1-20, 1-22, and 1-23 of Examples 1-14, 1-15, 1-17, and 1-18 were synthesized in the same manner as in the synthesis of compound 21, except that
5-bromothiophene-2-carboxyaldehyde (5.7 mmol) was changed
to 5-hexylthiophene-2-carboxyaldehyde (5.0 mmol) in compound 1-19 of Example 1-14,
to 5-methylthiophene-2-carboxyaldehyde (5.1 mmol) in compound 1-20 of Example 1-15,
to 5-methoxythiophene-2-carboxyaldehyde (5.2 mmol) in compound 1-22 of Example 1-17, and
to 2-thiophenecarboxyaldehyde (5.3 mmol) in compound 1-23 of Example 1-18, respectively. Similarly to the compound 1-21, production of the compounds was confirmed by $^1$H-NMR, and it was found that the intended compounds were obtained.

Example 1-19: Synthesis of Compound 1-25 Having Azomethine Part in which Heterocyclic Ring of Chemical Formula 1 is Thiophene Ring Compound 1-25 of Example 1-19 was synthesized in the same manner as in the synthesis of compound 1-21, except that
4-nitrophenol (30.2 mmol) was changed to 2-methoxy-4-nitrophenol (20 mmol), and
5-bromothiophene-2-carboxyaldehyde (5.7 mmol) was changed to 5-hexylthiophene-2-carboxyaldehyde (5.0 mmol). Similarly to the compound 1-21, production of the compound was confirmed by $^1$H-NMR, and it was found that the intended compound was obtained.

Example 1-20: Synthesis of Compound 1-27 Having Azomethine Part in which Heterocyclic Ring of Chemical Formula 1 is Thiophene Ring Compound 1-27 of Example 1-20 was synthesized in the same manner as in the synthesis of compound 1-21, except that
4-nitrophenol (30.2 mmol) was changed to 2-methyl-4-nitrophenol (30 mmol),
1-iodohexane (90.6 mmol) was changed to 1-iodooctane (90 mmol), and
5-bromothiophene-2-carboxyaldehyde (5.7 mmol) was changed to 5-hexylthiophene-2-carboxyaldehyde (5.6 mmol). Similarly to the compound 1-21, production of the compound was confirmed by $^1$H-NMR, and it was found that the intended compound was obtained.

Example 1-21: Synthesis of Compound 1-29 Having Azomethine Part in which Heterocyclic Ring of Chemical Formula 1 is Thiophene Ring Compound 1-29 of Example 1-21 was synthesized in the same manner as in the synthesis of compound 1-21, except that
4-nitrophenol (30.2 mmol) was changed to 2-methyl-4-nitrobenzoic acid (10 mmol), and
5-bromothiophene-2-carboxyaldehyde (5.7 mmol) was changed to 5-hexylthiophene-2-carboxyaldehyde (5.7 mmol). Similarly to the compound 1-21, production of the compound was confirmed by $^1$H-NMR, and it was found that the intended compound was obtained.

Examples 1-22 to 1-27: Synthesis of Compounds 1-30 to 1-35 Having Azomethine Part in which Heterocyclic Ring of Chemical Formula 1 is Thiophene Ring Compounds 1-30 to 1-35 of Examples 1-22 to 1-27 were synthesized in the same manner as in the synthesis of compound 1-21, except that
4-nitrophenol (30.2 mmol) was changed to 2-methyl-4-nitrophenol (30 mmol) in Examples 1-22 to 1-24, and
5-bromothiophene-2-carboxyaldehyde (5.7 mmol) was changed to 4-hexylthiophene-2-carboxyaldehyde (5.3 mmol) in Examples 1-22 and 1-25, to 4-methylthiophene-2-carboxyaldehyde (5.2 mmol) in Examples 1-23 and 1-26, and to 4-bromothiophene-2-carboxyaldehyde (5.2 mmol) in Examples 1-24 and 1-27. Similarly to the compound 1-21, production of the compounds was confirmed by $^1$H-NMR, and it was found that the intended compounds were obtained.

Examples 1-28 to 1-35: Synthesis of Compounds 1-36 to 1-43 Having Azomethine Part in which Heterocyclic Ring of Chemical Formula 1 is Thiophene Ring Compounds 1-36 to 1-43 of Examples 1-28 to 1-35 were synthesized in the same manner as in the synthesis of compound 1-21, except that the processes of Schemes 1 and 2 were omitted while in Scheme 3, 4-(hexyloxy)aniline (5.7 mmol) was changed to 3-methyl-4-hexylaniline (6 mmol) in Examples 1-28 to 1-31, and to 4-hexylaniline (6 mmol) in Examples 1-32 to 1-35, and 5-bromothiophene-2-carboxyaldehyde (5.7 mmol) was changed to 5-hexylthiophene-2-carboxyaldehyde (5.1 mmol) in Examples 1-28 and 1-32, to 5-methylthiophene-2-carboxyaldehyde (5.2 mmol) in Examples 1-29 and 1-33, and to 5-methoxythiophene-2-carboxyaldehyde (5.1 mmol) in Examples 1-31 and 1-35. Similarly to the compound 1-21, production of the compounds was confirmed by $^1$H-NMR, and it was found that the intended compounds were obtained.

Examples 1-36 to 1-39: Synthesis of Compounds 1-44 to 1-47 Having Azomethine Part in which Heterocyclic Ring of Chemical Formula 1 is Thiophene Ring Compounds 1-44 to 1-47 of Examples 1-36 to 1-39 were synthesized in the same manner as in the synthesis of compound 1-21, except that the processes of Schemes 1 and 2 were omitted while in Scheme 3, 4-(hexyloxy)aniline (5.7 mmol) was changed to 4-hexylaniline (6 mmol), and 5-bromothiophene-2-carboxyaldehyde (5.7 mmol) was changed to 4-hexylthiophene-2-carboxyaldehyde (5.3 mmol) in Example 1-36, to 4-methylthiophene-2-carboxyaldehyde (5.2 mmol) in Example 1-37, to 4-bromothiophene-2-carboxyaldehyde (5.1 mmol) in Example 1-38, and to 4-methoxythiophene-2-carboxyaldehyde (5.0 mmol) in Example 1-39. Similarly to the compound 1-21, production of the compounds was confirmed by $^1$H-NMR, and it was found that the intended compounds were obtained.

Example 1-40: Synthesis of Compound 1-48 Having Azomethine Part in which Heterocyclic Ring of Chemical Formula 1 is Thiophene Ring Compound 1-48 of Example 1-40 was synthesized in the same manner as in the synthesis of compound 1-21, except that 4-nitrophenol (30.2 mmol) was changed to 3-nitrophenol (30 mmol), and 5-bromothiophene-2-carboxyaldehyde (5.7 mmol) was changed to 5-methylthiophene-2-carboxyaldehyde (5.5 mmol) Similarly to the compound 1-21, production of the compound was confirmed by $^1$H-NMR, and it was found that the intended compound was obtained.

Example 1-41: Synthesis of Compound 1-49 Having Azomethine Part in which Heterocyclic Ring of Chemical Formula 1 is Thiophene Ring Compound 1-49 of Example 1-41 was synthesized in the same manner as in the synthesis of compound 1-21, except that 5-bromothiophene-2-carboxyaldehyde (5.7 mmol) was changed to 5-methylthiophene-3-carboxyaldehyde (5.0 mmol). Similarly to the compound 1-21, production of the compound was confirmed by $^1$H-NMR, and it was found that the intended compound was obtained.

Compounds 1-50 and 1-51 having an azomethine part used in Examples 1-42 and 1-43, in which the heterocyclic ring of Chemical Formula 1 is a thiophene ring, were synthesized in the same manner as in the synthesis of compound 1-50 of Table 1-1 of Example 1-42 as described below. The synthesis method for the compound 1-50 of Example 1-42 will be described as a representative example.

Synthesis of Compound Having Azomethine Part

Example 1-42: Synthesis of Compound 1-50 of Table 1-1

Scheme 4

[Chemical Formula 18]

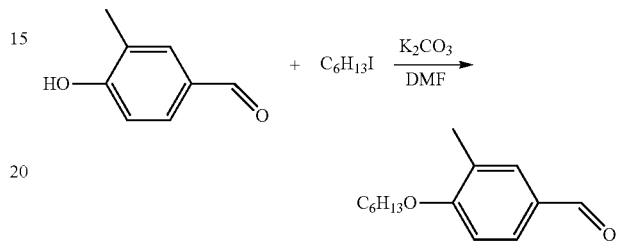

Scheme 5

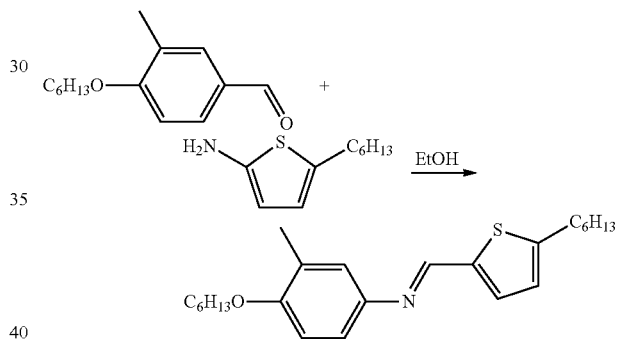

Scheme 4

Into a 100-ml four-necked flask equipped with a cooling tube, a nitrogen inlet tube, and a thermometer, 4-hydroxy-3-methylbenzaldehyde (3.0 g, 22.0 mmol), 1-iodohexane (14.0 g, 66.1 mmol), potassium carbonate (7.6 g, 55.1 mmol), and 30 ml of dimethylformamide were introduced, and the mixture was heated to reflux. The reaction liquid was washed with water and then concentrated, and the resultant was purified by column chromatography (ethyl acetate: heptane=1:9 (volume ratio)). Thus, 4.1 g (yield 84%) of 4-hexyloxy-3-methylbenzaldehyde was obtained.

Scheme 5

Into a 100-ml four-necked flask equipped with a cooling tube, a nitrogen inlet tube, and a thermometer, 4-hexyloxy-3-methylbenzaldehyde (1.0 g, 4.5 mmol), 5-hexylthiophene-2-amine (0.8 g, 4.5 mmol), and 20 ml of ethanol were introduced, and the mixture was heated and stirred at 50° C. The reaction liquid was suction-filtered, and a powder thus obtained was washed with cold ethanol. Furthermore, recrystallization was performed in a mixed solvent of methanol/ethanol, and 0.62 g (yield 35%) of compound 1-50 as a target substance was obtained.

Production of compound 1-50 was confirmed by $^1$H-NMR. $^1$H NMR (400 MHz, CDCl$_3$); 7.35 ppm (s, 1H, CH=N), 7.72 ppm (d, 2H, aryl), 7.38 ppm (s, 1H, thiophene), 7.00 ppm (d, 1H, aryl), 6.76 ppm (s, 1H, thiophene), 4.07 ppm (t, 2H, methylene), 2.85 ppm (t, 2H, methylene), 2.10 ppm (s, 3H, methyl), 1.78 ppm (m, 2H, methylene), 1.70 ppm (m, 2H, methylene), 1.45 ppm (m, 2H, methylene), 1.32 ppm (m, 10H, methylene), 0.86 ppm (t, 6H, methyl).

Example 1-43: Synthesis of Compound 1-51 Having Azomethine Part in which Heterocyclic Ring of Chemical Formula 1 is Thiophene Ring Compound 1-51 of Example 1-43 was synthesized in the same manner as in the synthesis of compound 1-50, except that 4-hydroxy-3-methylbenzaldehyde (22.0 mmol) was changed to 4-hyroxybenzaldehyde (20 mmol). Similarly to the compound 1-50, production of the compound was confirmed by ¹H-NMR, and it was found that the intended compound was obtained.

Compounds 1-55 to 1-57 having an azomethine part of Examples 1-44 to 1-46, in which the heterocyclic ring of Chemical Formula 1 was a furan ring, were synthesized in the same manner as in the case of the compound having an azomethine part, in which the heterocyclic ring of Chemical Formula 1 is a thiophene ring. The synthesis method for compound 1-55 of Example 1-44 will be described as a representative example.

Synthesis of Compound Having Azomethine Part

Example 1-44: Synthesis of Compound 1-55 of Table 1-1

Scheme 6

[Chemical Formula 19]

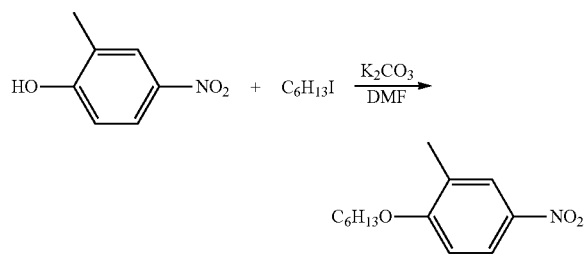

Scheme 7

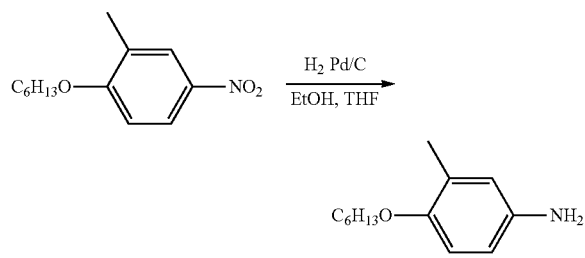

Scheme 8

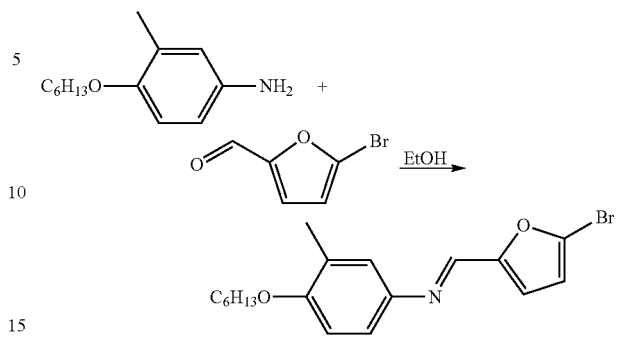

Scheme 6
Into a 100-ml four-necked flask equipped with a cooling tube, a nitrogen inlet tube, and a thermometer, 2-methyl-4-nitrophenol (3.1 g, 20 mmol), 1-iodohexane (12.9 g, 60.7 mmol), potassium carbonate (7.0 g, 50.6 mmol), and 30 ml of dimethylformamide were introduced, and the mixture was heated to reflux. The reaction liquid was washed with water and then concentrated, and the resultant was purified by column chromatography (ethyl acetate:heptane=1:9 (volume ratio)). Thus, 3.8 g (yield 79%) of 3-methyl-4-(hexyloxy)nitrobenzene was obtained.

Scheme 7
Into a 500-ml conical flask, 3-methyl-4-(hexyloxy)nitrobenzene (3.3 g, 14 mmol), palladium-carbon (0.07 g, 150 mmol), and 40 ml each of ethanol and tetrahydrofuran were introduced, and the mixture was stirred while hydrogen ($H_2$) was enclosed. Palladium-carbon was removed from the reaction liquid, a solution thus obtained was concentrated, and then recrystallization was performed from ethanol. Thus, 2.1 g (yield 73%) of 3-methyl-4-hexyloxybenzeneamine was obtained.

Scheme 8
Into a 100-ml four-necked flask equipped with a cooling tube, a nitrogen inlet tube, and a thermometer, 3-methyl-4-hexyloxybenzeneamine (1.0 g, 5.0 mmol), 5-bromo-2-furaldehyde (0.9 g, 5.0 mmol), and 20 ml of ethanol were introduced, and the mixture was heated and stirred at 50° C. The reaction liquid was suction-filtered, and a powder thus obtained was washed with cold ethanol. Furthermore, recrystallization was performed in a mixed solvent of methanol/ethanol, and 0.61 g (yield 33%) of compound 1-55 as a target substance was obtained.

Production of compound 1-55 was confirmed by ¹H-NMR. ¹H NMR (400 MHz, CDCl₃); 8.00 ppm (s, 1H, CH=N), 7.25 ppm (d, 1H, aryl), 7.21 ppm (s, 1H, aryl), 7.10 ppm (d, 1H, furan), 6.95 ppm (d, 1H, aryl), 6.82 ppm (d, 1H, furan), 4.09 ppm (t, 2H, methylene), 2.19 ppm (s, 3H, methyl), 1.80 ppm (m, 2H, methylene), 1.46 ppm (m, 2H, methylene), 1.34 ppm (m, 4H, methylene), 0.91 ppm (t, 3H, methyl).

Example 1-45: Synthesis of Compound 1-56 Having Azomethine Part in which Heterocyclic Ring of Chemical Formula 1 is Furan Ring Compound 1-56 of Example 1-45 was synthesized in the same manner as in the synthesis of compound 1-55, except that 5-bromo-2-furaldehyde (5.0 mmol) was changed to 4-bromo-2-furaldehyde (5.0 mmol). Similarly to the compound 1-55, production of the compound was confirmed by ¹H-NMR, and it was found that the intended compound was obtained.

Example 1-46: Synthesis of Compound 1-57 Having Azomethine Part in which Heterocyclic Ring of Chemical Formula 1 is Furan Ring Compound 1-57 of Example 1-46 was synthesized in the same manner as in the synthesis of compound 1-55, except that 2-methyl-4-nitrophenol (20 mmol) was changed to 4-nitrophenol (20 mmol). Similarly to the compound 1-55, production of the compound was confirmed by ¹H-NMR, and it was found that the intended compound was obtained.

Compounds 1-70, 1-72, and 1-74 having an azomethine part of Examples 1-47 to 1-49, in which the heterocyclic ring of Chemical Formula 1 is a pyrrole ring, were also synthesized in the same manner as in the case of the compound having an azomethine part, in which the heterocyclic ring of Chemical Formula 1 is a thiophene ring. The synthesis method for compound 1-70 of Example 1-47 will be described as a representative example.

Synthesis of Compound Having Azomethine Part

Example 1-47: Synthesis of Compound 1-70 of Table 1-1

Scheme 9

[Chemical Formula 20]

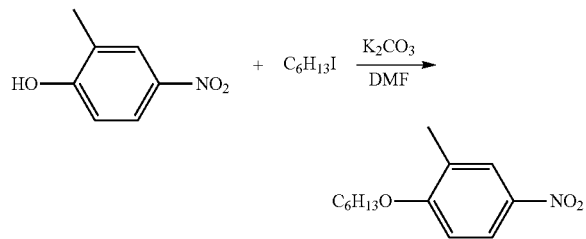

Scheme 10

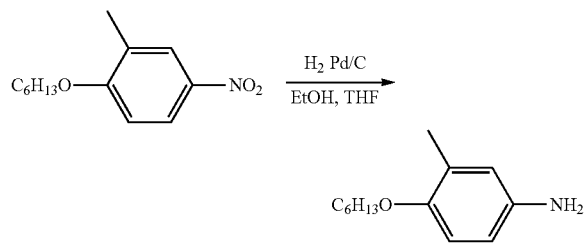

Scheme 11

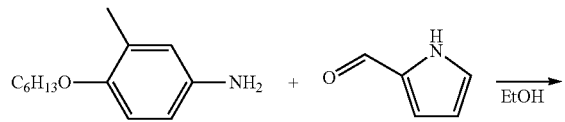

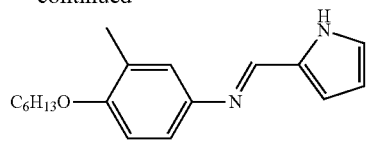

Scheme 9

Into a 100-ml four-necked flask equipped with a cooling tube, a nitrogen inlet tube, and a thermometer, 2-methyl-4-nitrophenol (3.0 g, 20.0 mmol), 1-iodohexane (12.5 g, 58.8 mmol), potassium carbonate (6.8 g, 49.0 mmol), and 50 ml of dimethylformamide were introduced, and the mixture was heated to reflux. The reaction liquid was washed with water and then concentrated, and the resultant was purified by column chromatography (ethyl acetate:heptane=1:9 (volume ratio)), and thus 3.6 g (yield 77%) of 4-hexyloxy-3-methylnitrobenzene was obtained.

Scheme 10

Into a 500-ml conical flask, 4-hexyloxy-3-methylnitrobenzene (3.1 g, 13.1 mmol) and palladium-carbon (0.06 g, 129 mmol) were introduced, and 30 ml each of ethanol and tetrahydrofuran were introduced therein. The mixture was stirred while hydrogen was enclosed. Palladium-carbon was removed from the reaction liquid, a solution thus obtained was concentrated, and then recrystallization was performed from ethanol. Thus, 1.9 g (yield 70%) of 4-hexyloxy-3-methylbenzeneamine was obtained.

Scheme 11 Into a 100-ml four-necked flask equipped with a cooling tube, a nitrogen inlet tube, and a thermometer, 4-hexyloxy-3-methylbenzeneamine (1.0 g, 5.0 mmol), pyrrole-2-carboxyaldehyde (0.47 g, 5.0 mmol), and 20 ml of ethanol were introduced, and the mixture was heated and stirred at 50° C. The reaction liquid was suction-filtered, and a powder thus obtained was washed with cold ethanol. Furthermore, recrystallization was performed in a mixed solvent of methanol/ethanol, and thus 0.71 g (yield 50%) of compound 1-70 as a target substance was obtained.

Production of compound 1-70 was confirmed by ¹H-NMR. ¹H NMR (400 MHz, CDCl₃); 9.3 ppm (s, 1H, NH), 8.06 ppm (s, 1H, CH=N), 7.26 ppm (d, 1H, aryl), 7.20 ppm (s, 1H, aryl), 6.96 ppm (d, 1H, pyrrol), 6.92 ppm (d, 1H, aryl), 6.54 ppm (d, 1H, pyrrol), 6.12 ppm (t, 1H, pyrrol), 4.13 ppm (t, 2H, methylene), 2.15 ppm (s, 3H, methyl), 1.78 ppm (m, 2H, methylene), 1.40 ppm (m, 2H, methylene), 1.37 ppm (m, 4H, methylene), 0.85 ppm (t, 3H, methyl).

Example 1-48: Synthesis of Compound 1-72 Having Azomethine Part in which Heterocyclic Ring of Chemical Formula 1 is Pyrrole Ring Compound 1-72 of Example 1-48 was synthesized in the same manner as in the synthesis of compound 1-70, except that pyrrole-2-carboxyaldehyde (5.0 mmol) was changed to 2-hexyl-1-methylpyrrole-5-carboxyaldehyde (5.0 mmol). Similarly to the compound 1-70, production of the compound was confirmed by ¹H-NMR, and it was found that the intended compound was obtained.

Example 1-49: Synthesis of Compound 1-74 Having Azomethine Part in which Heterocyclic Ring of Chemical Formula 1 is Pyrrole Ring Compound 1-74 of Example 1-49 was synthesized in the same manner as in the synthesis of compound 1-70, except that 2-methyl-4-nitrophenol (20 mmol) was changed to 4-nitrophenol (20 mmol), and pyrrole-2-carboxyaldehyde (5.0 mmol) was changed to 2-hexyl-1-methylpyrrole-5-carboxyaldehyde (5.0 mmol). Similarly to the compound 1-70, production of the compound was confirmed by $^1$H-NMR, and it was found that the intended compound was obtained.

Comparative Example 1-1: Synthesis of Azobenzene Compound 1-75

A compound represented by the following Chemical Formula (2) (azobenzene compound 1-75) was obtained in the same manner as in "(1-1-1) Synthesis of UV-softening material A" described in paragraphs "0217" to "0224" of Japanese Patent Application Laid-Open No. 2014-191078. Similarly to compound 1-70, production of the compound was confirmed by $^1$H-NMR, and it was found that the intended compound was obtained.

[Chemical Formula 21]

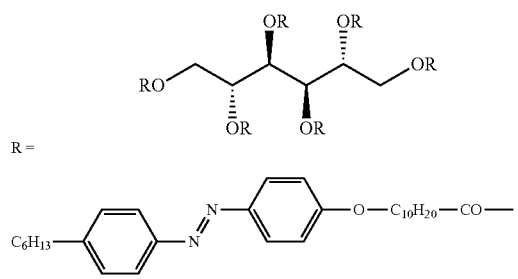

(2)

The numbers of compounds obtained in Examples 1-1 to 1-49 and Comparative Example 1-1 and structures thereof are shown in the following Table 1-2 (Table 1-2-1 and Table 1-2-2).

[Photoresponsive Adhesion Test]

Figure 4:
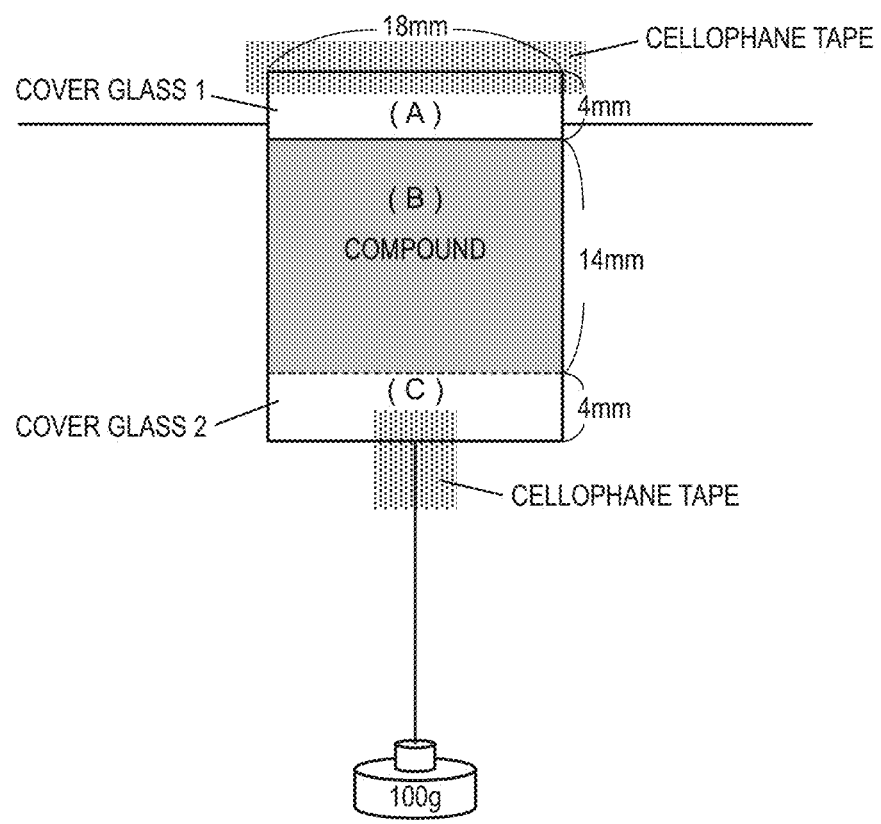
FIG. 4 is an outline diagram of an apparatus for measuring a change in the adhesiveness concomitant with light irradiation for the compounds synthesized in Examples and Comparative Examples.

Changes in the adhesiveness concomitant to light irradiation of the compounds synthesized in Examples 1-1 to 1-49 and Comparative Example 1-1 were evaluated by the following photoresponsive adhesion test using an apparatus as illustrated in FIG. 4. As shown in FIG. 4, 2 mg of a compound was mounted on a cover glass 1 measuring 18 mm on each of four sides, within a radius of 6 mm from the center of the glass, and a cover glass 2 having the same size was covered at a position shifted by about 4 mm in a direction parallel to the cover glass 1 so as to cover the entire compound. This was heated to melt the sample, and thus the cover glass 1 and the cover glass 2 were adhered. Each of the samples thus obtained was subjected to a non-fluidity→fluidity test as described below and was subsequently subjected to a fluidity→non-fluidity test as described below.

<Non-Fluidity→Fluidity Test (Fluidization Test)>

The part (A) shown in FIG. 4 was fixed to a holder with Cellophane tape, and a vinyl string 30 cm long loaded with a 100-g weight was fixed to the part (C) with Cellophane tape. The part (B) was irradiated with light having a wavelength of 365 nm in an amount of irradiation of 30 μm$^2$, it was checked whether the cover glass 2 would come off from the cover glass 1, and the result was judged according to the following evaluation criteria. The results thus obtained are shown in Table 1-2 (Table 1-2-1 and Table 1-2-2).

—Evaluation Criteria for Non-Fluidity→Fluidity Test (Fluidization Test)—

○: The cover glass 2 completely came off from the cover glass 1.

Δ: The cover glass 2 was shifted.

x: The cover glass 2 did not move.

<Fluidity→Non-Fluidity Test (Non-Fluidization Test)>

One hour after the initiation of the non-fluidity→fluidity test (for this one hour, left to stand in a natural environment, that is, at room temperature), a cover glass 3 (having the same size as the cover glasses 1 and 2) was mounted so as to cover the sample portion (part (B)) of the cover glass 1 used in the above-described test, it was checked whether the cover glass 1 and the cover glass 3 would adhere, and the result was judged according to the following evaluation criteria. The results thus obtained are shown in Table 1-2 (Table 1-2-1 and Table 1-2-2).

Furthermore, even when a similar experiment was carried out after 5 minutes (for the 5 minutes, left to stand in a natural environment, that is, at room temperature (in the range of 25±15° C.)) from the completion of light irradiation of the non-fluidity→fluidity test, similar results were obtained.

—Evaluation Criteria for Fluidity→Non-Fluidity Test (Non-Fluidization Test)—

○: Did not adhere (non-fluidized)

Δ: Partially adhered (a fluidized state was maintained in some portion)

x: Adhered (a fluidized state was maintained).

TABLE 1-2

| Example No. | Compound No. | X | $Z_1$ | $Z_2$ | $R_1$ | $R_2$ | $R_3$ | $R_4$ | $R_5$ |
|---|---|---|---|---|---|---|---|---|---|
| 1-1 | 1-1 | S | CH | N | $C_6H_{13}$ | H | H | Group of Formula 2 | H |
| 1-2 | 1-4 | | | | $C_3H_7$ | H | H | Group of Formula 2 | H |
| 1-3 | 1-5 | | | | $CH_3$ | H | H | Group of Formula 2 | H |
| 1-4 | 1-6 | | | | $OC_6H_{13}$ | H | H | Group of Formula 2 | H |
| 1-5 | 1-8 | | | | $COOC_6H_{13}$ | H | H | Group of Formula 2 | H |
| 1-6 | 1-9 | | | | Br | H | H | Group of Formula 2 | H |
| 1-7 | 1-10 | | | | CN | H | H | Group of Formula 2 | H |
| 1-8 | 1-12 | | | | $OCH_3$ | H | H | Group of Formula 2 | H |
| 1-9 | 1-13 | | | | OH | H | H | Group of Formula 2 | H |

TABLE 1-2-continued

| | | | | | | | | | |
|---|---|---|---|---|---|---|---|---|---|
| 1-10 | 1-14 | | | | H | H | H | Group of Formula 2 | H |
| 1-11 | 1-15 | | | | $C_6H_{13}$ | $CH_3$ | H | Group of Formula 2 | H |
| 1-12 | 1-16 | | | | $C_6H_{13}$ | H | $CH_3$ | Group of Formula 2 | H |
| 1-13 | 1-17 | | | | $C_6H_{13}$ | H | H | Group of Formula 2 | $CH_3$ |
| 1-14 | 1-19 | | | | $C_6H_{13}$ | H | H | Group of Formula 2 | H |
| 1-15 | 1-20 | | | | $CH_3$ | H | H | Group of Formula 2 | H |
| 1-16 | 1-21 | | | | Br | H | H | Group of Formula 2 | H |
| 1-17 | 1-22 | | | | $OCH_3$ | H | H | Group of Formula 2 | H |
| 1-18 | 1-23 | | | | H | H | H | Group of Formula 2 | H |
| 1-19 | 1-25 | | | | $C_6H_{13}$ | H | H | Group of Formula 2 | H |
| 1-20 | 1-27 | | | | $C_6H_{13}$ | H | H | Group of Formula 2 | H |
| 1-21 | 1-29 | | | | $C_6H_{13}$ | H | H | Group of Formula 2 | H |
| 1-22 | 1-30 | | | | H | $C_6H_{13}$ | H | Group of Formula 2 | H |
| 1-23 | 1-31 | | | | H | $CH_3$ | H | Group of Formula 2 | H |
| 1-24 | 1-32 | | | | H | Br | H | Group of Formula 2 | H |
| 1-25 | 1-33 | | | | H | $C_6H_{13}$ | H | Group of Formula 2 | H |
| 1-26 | 1-34 | S | CH | N | H | $CH_3$ | H | Group of Formula 2 | H |
| 1-27 | 1-35 | | | | H | Br | H | Group of Formula 2 | H |
| 1-28 | 1-36 | | | | $C_6H_{13}$ | H | H | Group of Formula 2 | H |
| 1-29 | 1-37 | | | | $CH_3$ | H | H | Group of Formula 2 | H |
| 1-30 | 1-38 | | | | Br | H | H | Group of Formula 2 | H |
| 1-31 | 1-39 | | | | $OCH_3$ | H | H | Group of Formula 2 | H |
| 1-32 | 1-40 | | | | $C_6H_{13}$ | H | H | Group of Formula 2 | H |
| 1-33 | 1-41 | | | | $CH_3$ | H | H | Group of Formula 2 | H |
| 1-34 | 1-42 | | | | Br | H | H | Group of Formula 2 | H |
| 1-35 | 1-43 | | | | $OCH_3$ | H | H | Group of Formula 2 | H |
| 1-36 | 1-44 | | | | H | $C_6H_{13}$ | H | Group of Formula 2 | H |
| 1-37 | 1-45 | | | | H | $CH_3$ | H | Group of Formula 2 | H |
| 1-38 | 1-46 | | | | H | Br | H | Group of Formula 2 | H |
| 1-39 | 1-47 | | | | H | $OCH_3$ | H | Group of Formula 2 | H |
| 1-40 | 1-48 | | | | $CH_3$ | H | H | Group of Formula 2 | H |
| 1-41 | 1-49 | | | | $C_6H_{13}$ | H | Group of Formula 2 | H | H |
| 1-42 | 1-50 | | N | CH | $C_6H_{13}$ | H | H | Group of Formula 2 | H |
| 1-43 | 1-51 | | | | $C_6H_{13}$ | H | H | Group of Formula 2 | H |
| 1-44 | 1-55 | O | CH | N | Br | H | H | Group of Formula 2 | H |
| 1-45 | 1-56 | | | | H | Br | H | Group of Formula 2 | H |
| 1-46 | 1-57 | | | | Br | H | H | Group of Formula 2 | H |
| 1-47 | 1-70 | $NR_{10}$ | CH | N | H | H | H | Group of Formula 2 | H |

TABLE 1-2-continued

| Example No. | Compound No. | | | | | |
|---|---|---|---|---|---|---|
| 1-48 | 1-72 | $C_6H_{13}$ | H | H | Group of Formula 2 | H |
| 1-49 | 1-74 | $C_6H_{13}$ | H | H | Group of Formula 2 | H |
| Comparative Example 1-1 | 1-75 | Azobenzene compound | | | | |

| Example No. | Compound No. | $R_6$ | $R_7$ | $R_8$ | $R_9$ | $R_{10}$ | Photoresponsive adhesion test | |
|---|---|---|---|---|---|---|---|---|
| | | | | | | | Fluidization test | Non-fluidization test |
| 1-1 | 1-1 | $CH_3$ | $OC_6H_{13}$ | H | H | — | ○ | ○ |
| 1-2 | 1-4 | $CH_3$ | $OC_6H_{13}$ | H | H | — | ○ | ○ |
| 1-3 | 1-5 | $CH_3$ | $OC_6H_{13}$ | H | H | — | ○ | ○ |
| 1-4 | 1-6 | $CH_3$ | $OC_6H_{13}$ | H | H | — | ○ | ○ |
| 1-5 | 1-8 | $CH_3$ | $OC_6H_{13}$ | H | H | — | ○ | ○ |
| 1-6 | 1-9 | $CH_3$ | $OC_6H_{13}$ | H | H | — | ○ | ○ |
| 1-7 | 1-10 | $CH_3$ | $OC_6H_{13}$ | H | H | — | ○ | ○ |
| 1-8 | 1-12 | $CH_3$ | $OC_6H_{13}$ | H | H | — | ○ | ○ |
| 1-9 | 1-13 | $CH_3$ | $OC_6H_{13}$ | H | H | — | ○ | ○ |
| 1-10 | 1-14 | $CH_3$ | $OC_6H_{13}$ | H | H | — | ○ | ○ |
| 1-11 | 1-15 | $CH_3$ | $OC_6H_{13}$ | H | H | — | ○ | ○ |
| 1-12 | 1-16 | $CH_3$ | $OC_6H_{13}$ | H | H | — | ○ | ○ |
| 1-13 | 1-17 | H | $OC_6H_{13}$ | H | H | — | ○ | ○ |
| 1-14 | 1-19 | H | $OC_6H_{13}$ | H | H | — | ○ | ○ |
| 1-15 | 1-20 | H | $OC_6H_{13}$ | H | H | — | ○ | ○ |
| 1-16 | 1-21 | H | $OC_6H_{13}$ | H | H | — | ○ | ○ |
| 1-17 | 1-22 | H | $OC_6H_{13}$ | H | H | — | ○ | ○ |
| 1-18 | 1-23 | H | $OC_6H_{13}$ | H | H | — | ○ | ○ |
| 1-19 | 1-25 | $OCH_3$ | $OC_6H_{13}$ | H | H | — | ○ | ○ |
| 1-20 | 1-27 | $CH_3$ | $OC_8H_{17}$ | H | H | — | ○ | ○ |
| 1-21 | 1-29 | $CH_3$ | $COOC_6H_{13}$ | H | H | — | ○ | ○ |
| 1-22 | 1-30 | $CH_3$ | $OC_6H_{13}$ | H | H | — | ○ | ○ |
| 1-23 | 1-31 | $CH_3$ | $OC_6H_{13}$ | H | H | — | ○ | ○ |
| 1-24 | 1-32 | $CH_3$ | $OC_6H_{13}$ | H | H | — | ○ | ○ |
| 1-25 | 1-33 | H | $OC_6H_{13}$ | H | H | — | ○ | ○ |
| 1-26 | 1-34 | H | $OC_6H_{13}$ | H | H | — | ○ | ○ |
| 1-27 | 1-35 | H | $OC_6H_{13}$ | H | H | — | ○ | ○ |
| 1-28 | 1-36 | $CH_3$ | $C_6H_{13}$ | H | H | — | ○ | ○ |
| 1-29 | 1-37 | $CH_3$ | $C_6H_{13}$ | H | H | — | ○ | ○ |
| 1-30 | 1-38 | $CH_3$ | $C_6H_{13}$ | H | H | — | ○ | ○ |
| 1-31 | 1-39 | $CH_3$ | $C_6H_{13}$ | H | H | — | ○ | ○ |
| 1-32 | 1-40 | H | $C_6H_{13}$ | H | H | — | ○ | ○ |
| 1-33 | 1-41 | H | $C_6H_{13}$ | H | H | — | ○ | ○ |
| 1-34 | 1-42 | H | $C_6H_{13}$ | H | H | — | ○ | ○ |
| 1-35 | 1-43 | H | $C_6H_{13}$ | H | H | — | ○ | ○ |
| 1-36 | 1-44 | H | $C_6H_{13}$ | H | H | — | ○ | ○ |
| 1-37 | 1-45 | H | $C_6H_{13}$ | H | H | — | ○ | ○ |
| 1-38 | 1-46 | H | $C_6H_{13}$ | H | H | — | ○ | ○ |
| 1-39 | 1-47 | H | $C_6H_{13}$ | H | H | — | ○ | ○ |
| 1-40 | 1-48 | $C_6H_{13}$ | H | H | H | — | ○ | ○ |
| 1-41 | 1-49 | $CH_3$ | $C_6H_{13}$ | H | H | — | ○ | ○ |
| 1-42 | 1-50 | $CH_3$ | $C_6H_{13}$ | H | H | — | ○ | ○ |
| 1-43 | 1-51 | H | $C_6H_{13}$ | H | H | — | ○ | ○ |
| 1-44 | 1-55 | $CH_3$ | $C_6H_{13}$ | H | H | — | ○ | ○ |
| 1-45 | 1-56 | $CH_3$ | $C_6H_{13}$ | H | H | — | ○ | ○ |
| 1-46 | 1-57 | H | $C_6H_{13}$ | H | H | — | ○ | ○ |
| 1-47 | 1-70 | $CH_3$ | $C_6H_{13}$ | H | H | H | ○ | ○ |
| 1-48 | 1-72 | $CH_3$ | $C_6H_{13}$ | H | H | $CH_3$ | ○ | ○ |
| 1-49 | 1-74 | H | $C_6H_{13}$ | H | H | $CH_3$ | ○ | ○ |
| Comparative Example 1-1 | 1-75 | Azobenzene compound | | | | | ○ | X |

The "Group of Formula 2" in $R_3$ and $R_4$ of Table 1-2 (Table 1-2-1 and Table 1-2-2) refers to a "group represented by the Chemical Formula 2". Furthermore, "1-75" in the column of Compound No. in Table 1-2-2 refers to the azobenzene compound 1-75 synthesized in Comparative Example 1-1.

As is obvious from Table 1-2 (Table 1-2-1 and Table 1-2-2), it was found that the compounds of the Examples are all fluidized by light irradiation and are reversibly non-fluidized. In contrast, in the azobenzene compound 1-75 in Comparative Example 1-1, reversible non-fluidization after fluidization was not recognized.

[Production of Binder Resin]

(Production of Styrene-Acrylic Resin Particle Dispersion 1 Containing Styrene-Acrylic Resin 1)

(First Stage Polymerization)

Into a reaction vessel equipped with a stirring apparatus, a temperature sensor, a cooling tube, and a nitrogen inlet apparatus, a solution obtained by dissolving 8 parts by mass of sodium dodecyl sulfate in 3,000 parts by mass of ion-exchanged water was introduced, and while the solution was stirred at a stirring rate of 230 rpm under a nitrogen gas stream, the internal temperature was increased to 80° C. After the temperature increase, a solution obtained by dissolving 10 parts by mass of potassium persulfate in 200 parts by mass of ion-exchanged water was added thereto, and the liquid temperature was adjusted again to 80° C. A polymerizable monomer solution containing 480 parts by mass of styrene, 250 parts by mass of n-butyl acrylate, 68.0 parts by mass of methacrylic acid, and 16.0 parts by mass of n-octyl-3-mercaptopropionate was added dropwise thereto over one hour, subsequently the mixture was heated and stirred for 2 hours at 80° C., and thereby polymerization was carried out. Thus, a styrene-acrylic resin particle dispersion (1A) containing styrene-acrylic resin particles (1a) was prepared.

(Second Stage Polymerization)

Into a reaction vessel equipped with a stirring apparatus, a temperature sensor, a cooling tube, and a nitrogen inlet apparatus, a solution obtained by dissolving 7 parts by mass of sodium polyoxyethylene-2-dodecyl ether sulfate in 800 parts by mass of ion-exchanged water was introduced, the solution was heated to 98° C., and then 260 parts by mass of the above-described styrene-acrylic resin particle dispersion (1A), and a polymerizable monomer solution obtained by dissolving 245 parts by mass of styrene, 120 parts by mass of n-butyl acrylate, 1.5 parts by mass of n-octyl-3-mercaptopropionate, and 67 parts by mass of paraffin wax "HNP-11" (manufactured by Nippon Seiro Co., Ltd.) as a release agent at 90° C. were added thereto. The mixture was mixed and dispersed for one hour using a mechanical dispersing machine "CREARMIX" (manufactured by M Technique Co., Ltd.) having a circulation path, and thus a dispersion including emulsion particles (oil droplets) was prepared.

Next, an initiator solution obtained by dissolving 6 parts by mass of potassium persulfate in 200 parts by mass of ion-exchanged water was added to this dispersion, and polymerization was performed by heating and stirring this system over one hour at 82° C. Thus, a styrene-acrylic resin particle dispersion (1B) containing styrene-acrylic resin particles (1b) was prepared.

(Third Stage Polymerization)

A solution obtained by dissolving 11 parts by mass of potassium persulfate in 400 parts by mass of ion-exchanged water was added to the above-described styrene-acrylic resin particle dispersion (1B), and a polymerizable monomer solution containing 435 parts by mass of styrene, 130 parts by mass of n-butyl acrylate, 33 parts by mass of methacrylic acid, and 8 parts by mass of n-octyl-3-mercaptopropionate was added dropwise thereto over one hour under the temperature conditions of 82° C. After completion of the dropwise addition, polymerization was carried out by heating and stirring the mixture over 2 hours, and then the resulting liquid was cooled to 28° C. Thus, a styrene-acrylic resin particle dispersion 1 containing a styrene-acrylic resin 1 was obtained. Furthermore, the glass transition point Tg of this styrene-acrylic resin 1 was measured, and the glass transition point was 45° C.

(Production of Polyester Resin Particle Dispersion 1 Containing Polyester Resin 1)

Into a four-necked flask having a capacity of 10 liters and equipped with a nitrogen inlet tube, a dehydrating tube, a stirring device, and a thermocouple, 524 parts by mass of a bisphenol A propylene oxide 2-mol adduct, 105 parts by mass of terephthalic acid, 69 parts by mass of fumaric acid, and 2 parts by mass of tin octoate (esterification catalyst) were introduced, and a polycondensation reaction was carried out at a temperature of 230° C. for 8 hours. Furthermore, the polycondensation reaction was continued for one hour at 8 kPa, subsequently the system was cooled to 160° C., and a polyester resin 1 was obtained. 100 parts by mass of the polyester resin 1 was pulverized with "ROUNDEL MILL Model: RM" (manufactured by Tokuju Corporation) and was mixed with 638 parts by mass of a 0.26 mass % aqueous solution of sodium lauryl sulfate that had been produced in advance. While being stirred, the mixture was ultrasonically dispersed using an ultrasonic homogenizer "US-150T" (manufactured by Nissei Corporation) with V-LEVEL at 300 μA for 30 minutes, and thus a polyester resin particle dispersion 1 was obtained. Furthermore, the glass transition point Tg of this polyester resin 1 was measured, and the glass transition point was 42° C.

Example 1-51: Production of Toner 1-51

(Preparation of Cyan Dispersion)

11.5 parts by mass of sodium n-dodecyl sulfate was dissolved in 160 parts by mass of pure water, and 20 parts by mass of copper phthalocyanine (C.I. Pigment Blue 15:3) was slowly added thereto. Next, a cyan dispersion was prepared using "CLEARMIX (registered trademark) W-MOTION CLM-0.8 (manufactured by M Technique Co., Ltd.).

(Preparation of Azomethine Part-Containing Compound Particle Dispersion 1)

80 parts by mass of dichloromethane and 20 parts by mass of the compound 1-1 were mixed and stirred while being heated to 50° C., and a liquid containing the compound 1-1 was obtained. To 100 parts by mass of this liquid, a mixed liquid of 99.5 parts by mass of distilled water that had been warmed to 50° C. and 0.5 parts by mass of a 20 mass % aqueous solution of sodium dodecyl benzenesulfonate was added. Subsequently, the mixture was stirred for 20 minutes at 16,000 rpm using a homogenizer (manufactured by Heidolph Instruments GmbH & CO. KG) equipped with a shaft generator 18F to be emulsified, and thereby an emulsion 1 of a compound having an azomethine part was obtained.

The emulsion 1 of the compound having an azomethine part thus obtained was introduced into a separable flask, and while nitrogen was supplied into the gas phase, the emulsion was heated and stirred for 90 minutes at 40° C. to remove the organic solvent. Thereby, an azomethine part-containing compound particle dispersion 1 was obtained.

(Aggregation and Fusion)

504 parts by mass in terms of the solid content of the styrene-acrylic resin particle dispersion 1 produced as described above, 216 parts by mass in terms of the solid content of the azomethine part-containing compound particle dispersion, 900 parts by mass of ion-exchanged water, and 70 parts by mass in terms of the solid content of the cyan dispersion were introduced into a reaction apparatus equipped with a stirring apparatus, a temperature sensor, and a cooling tube. The temperature inside the vessel was maintained at 30° C., and a 5 mol/liter aqueous solution of sodium hydroxide was added thereto to adjust the pH to 10.

Next, an aqueous solution obtained by dissolving 2 parts by mass of magnesium chloride hexahydrate in 1,000 parts by mass of ion-exchanged water was added dropwise thereto over 10 minutes under stirring, and then temperature increase was initiated. This system was heated up to 70° C. for 60 minutes, 70° C. was maintained, and a particle growth reaction was continued. The particle size of associated particles was measured in this state using a "MULTISIZER- 3" (manufactured by Beckman Coulter, Inc.), and at the time point when the volume based median diameter (D50) became 6.5 μm, an aqueous solution obtained by dissolving 190 parts by mass of sodium chloride in 760 parts by mass of ion-exchanged water was added thereto to terminate particle growth. The mixture was stirred for one hour at 70° C., subsequently temperature increase was further carried out, and the mixture was heated and stirred in a state of 75° C. to thereby implement fusion of the particles. Subsequently, the mixture was cooled to 30° C., and thus a dispersion of toner particles was obtained.

The dispersion of toner particles obtained as described above was subjected to solid-liquid separation with a centrifuge, and a wet cake of the toner particles was formed. The wet cake was washed with ion-exchanged water at 35° C. using the centrifuge until the electrical conductivity of the filtrate reached 5 μS/cm, subsequently the wet cake was transferred to "FLASH JET DRYER (manufactured by Seishin Enterprise Co., Ltd.)", and the wet cake was dried until the moisture amount reached 0.5% by mass. Thus, a toner 1-51 was produced.

Production of Toners 1-52 to 1-108 of Examples 1-52 to 1-108 and Toner 1-109 of Comparative Example 1-2

Toners 1-52 to 1-109 were produced in the same manner as in the production of the toner 1-51 of Example 1-51 by appropriately changing according to the matters described in Table 1-3 (Table 1-3-1 and Table 1-3-2).

[Production of Developer]

The toners 1-51 to 1-109 produced as described above were mixed with ferrite carrier particles having a volume average particle size of 30 μm and coated with a copolymer resin of cyclohexane methacrylate and methyl methacrylate (monomer mass ratio 1:1) so as to obtain a toner particle concentration of 6% by mass, and developers 1-51 to 1-109 were obtained. Mixing was carried out for 30 minutes using a V-type mixer.

<Evaluation Method>

[Image Forming Method]

A toner image was formed on plain paper as a recording medium using each of the developers thus obtained, and a print was obtained. Specifically, a developer was disposed between a pair of parallel flat plate (aluminum) electrodes, one electrode being provided with the developer and the other electrode being provided with gloss coated paper (basis weight: 128 g/m$^2$), while the developer was caused to slide by magnetic force, and the toner was developed at a gap between the electrodes of 0.5 mm under the conditions of the DC bias and the AC bias so that the amount of toner attachment would be 4 g/m$^2$. Thus, a toner image was formed on the surface of the plain paper, the toner image was fixed with a fixing apparatus, and thus a print was obtained.

[Evaluation: Fixability Test]

The image measuring 1 cm on each of four sides on this print was rubbed 10 times by applying a pressure of 50 kPa with "JK WIPER (registered trademark)" (manufactured by Nippon Paper Crecia Co., Ltd.), and the fixing ratio of the image was evaluated. A fixing ratio of 50% or higher was considered acceptable. The evaluation results (fixing ratio) of the fixability test thus obtained are shown in the following Table 1-3. Meanwhile, the fixing ratio of the image is a value, expressed in percentage, obtained by measuring the densities of the image after printing and the image after rubbing with a reflection density meter "RD-918" (manufactured by Sakata Inx Engineering Co., Ltd.), and dividing the reflection density of the solid image after rubbing by the reflection density of the solid image after printing.

Regarding the fixing apparatus, the following three kinds of apparatuses configured by appropriately modifying the apparatus illustrated in FIG. 2 were used.

Fixing apparatus No. 1: The compression unit 9 of FIG. 2 is absent, the wavelength of the ultraviolet light irradiated from the irradiation unit 40 is 365 nm (light source: LED light source having an emission wavelength of 365 nm±10 nm), and the amount of irradiation is 10 J/cm$^2$. Furthermore, the toner softened by ultraviolet light irradiation was solidified (the compound was non-fluidized) and fixed in a natural environment, that is, in a state of being left to stand at room temperature (20° C.), until the toner reached the paper ejection unit 14 (see FIG. 1).

Fixing apparatus No. 2: There is the compression unit 9 of FIG. 2, the temperature of the pressing member 91 is 20° C., and the pressure at the time of pressing is 0.2 MPa. The light source and the amount of irradiation of the irradiation unit are similar to those of No. 1. Furthermore, the toner that had been softened by ultraviolet light irradiation was fixed by pressing by the pressing member 91, and subsequently, the toner was solidified (the compound was non-fluidized) in a state of leaving to stand at room temperature (20° C.) until the toner reached the paper ejection unit 14 (see FIG. 1).

Fixing apparatus No. 3: There is the compression unit 9 of FIG. 2, and the temperature of the pressing member 91 is 80° C. The light source and the amount of irradiation of the irradiation unit are similar to those of No. 1. Furthermore, the pressure at the time of pressing with the pressing member 91 is similar to that of No. 2. Furthermore, the toner that had been softened by ultraviolet light irradiation was further softened and fixed by pressing and heating by the pressing member 91. Subsequently, the toner was solidified (the compound was non-fluidized) in a state of being left to stand at room temperature (20° C.) until the toner reached the paper ejection unit 14 (see FIG. 1).

[Evaluation of Color Reproducibility]

For the images of Examples obtained as described above, the color reproducibility was evaluated by a visual evaluation made by ten monitors according to the following evaluation criteria. Specifically, regarding the toners described in Examples, as samples for evaluation and comparison, toners excluding the compound having an azomethine part were produced and developed in the same manner as in (Image formation), and fixing was performed with a fixing apparatus No. 4 as described below.

Fixing Apparatus No. 4:

There is the compression unit 9 of FIG. 2, the temperature of the pressing member 91 is 150° C., the pressure at the time of pressing is 0.2 MPa, and light irradiation is not carried out.

The samples for evaluation and comparison and the samples described in Examples were shown in sequence to the ten monitors, and the monitors were questioned about whether the colors of two images were clearly different. The determination results based on the following evaluation criteria for color reproducibility are shown in the following Table 1-3 (Table 1-3-1 and Table 1-3-2).

—Evaluation Criteria for Color Reproducibility—
⊙: Two or fewer people answered that the colors were clearly different.
○: Three or four people answered that the colors were clearly different.
Δ: Five to seven people answered that the colors were clearly different.
x: Eight or more people answered that the colors were clearly different.

The configurations of the toners, the type of the fixing apparatus, and the evaluation results are shown in the following Table 1-3 (Table 1-3-1 and Table 1-3-2).

TABLE 1-3

| | Compound having azomethine part | | | | | Evaluation | |
|---|---|---|---|---|---|---|---|
| Example No. | Compound No. | Azomethine derivative:binder resin (mass ratio) | Binder resin | Colorant | Fixing apparatus | Fixability | Color reproducibility |
| 1-51 | 1-1 | 30:70 | Styrene-acrylic | Cyan | 1 | 90 | ⊙ |
| 1-52 | 1-4 | 30:70 | Styrene-acrylic | Cyan | 1 | 89 | ⊙ |
| 1-53 | 1-5 | 30:70 | Styrene-acrylic | Cyan | 1 | 89 | ⊙ |
| 1-54 | 1-6 | 30:70 | Styrene-acrylic | Cyan | 1 | 82 | ⊙ |
| 1-55 | 1-8 | 30:70 | Styrene-acrylic | Cyan | 1 | 80 | ⊙ |
| 1-56 | 1-9 | 30:70 | Styrene-acrylic | Cyan | 1 | 88 | ⊙ |
| 1-57 | 1-10 | 30:70 | Styrene-acrylic | Cyan | 1 | 85 | ⊙ |
| 1-58 | 1-12 | 30:70 | Styrene-acrylic | Cyan | 1 | 90 | ⊙ |
| 1-59 | 1-13 | 30:70 | Styrene-acrylic | Cyan | 1 | 82 | ⊙ |
| 1-60 | 1-14 | 30:70 | Styrene-acrylic | Cyan | 1 | 77 | ⊙ |
| 1-61 | 1-15 | 30:70 | Styrene-acrylic | Cyan | 1 | 82 | ⊙ |
| 1-62 | 1-16 | 30:70 | Styrene-acrylic | Cyan | 1 | 80 | ⊙ |
| 1-63 | 1-17 | 30:70 | Styrene-acrylic | Cyan | 1 | 81 | ⊙ |
| 1-64 | 1-19 | 30:70 | Styrene-acrylic | Cyan | 1 | 89 | ⊙ |
| 1-65 | 1-20 | 30:70 | Styrene-acrylic | Cyan | 1 | 88 | ⊙ |
| 1-66 | 1-21 | 30:70 | Styrene-acrylic | Cyan | 1 | 89 | ⊙ |
| 1-67 | 1-22 | 30:70 | Styrene-acrylic | Cyan | 1 | 89 | ⊙ |
| 1-68 | 1-23 | 30:70 | Styrene-acrylic | Cyan | 1 | 87 | ⊙ |
| 1-69 | 1-25 | 30:70 | Styrene-acrylic | Cyan | 1 | 80 | ⊙ |
| 1-70 | 1-27 | 30:70 | Styrene-acrylic | Cyan | 1 | 78 | ⊙ |
| 1-71 | 1-29 | 30:70 | Styrene-acrylic | Cyan | 1 | 77 | ⊙ |
| 1-72 | 1-30 | 30:70 | Styrene-acrylic | Cyan | 1 | 90 | ⊙ |
| 1-73 | 1-31 | 30:70 | Styrene-acrylic | Cyan | 1 | 89 | ⊙ |
| 1-74 | 1-32 | 30:70 | Styrene-acrylic | Cyan | 1 | 88 | ⊙ |
| 1-75 | 1-33 | 30:70 | Styrene-acrylic | Cyan | 1 | 89 | ⊙ |
| 1-76 | 1-34 | 30:70 | Styrene-acrylic | Cyan | 1 | 88 | ⊙ |
| 1-77 | 1-35 | 30:70 | Styrene-acrylic | Cyan | 1 | 89 | ⊙ |
| 1-78 | 1-36 | 30:70 | Styrene-acrylic | Cyan | 1 | 82 | ⊙ |
| 1-79 | 1-37 | 30:70 | Styrene-acrylic | Cyan | 1 | 85 | ⊙ |
| 1-80 | 1-38 | 30:70 | Styrene-acrylic | Cyan | 1 | 83 | ⊙ |
| 1-81 | 1-39 | 30:70 | Styrene-acrylic | Cyan | 1 | 85 | ⊙ |
| 1-82 | 1-40 | 30:70 | Styrene-acrylic | Cyan | 1 | 89 | ⊙ |
| 1-83 | 1-41 | 30:70 | Styrene-acrylic | Cyan | 1 | 88 | ⊙ |
| 1-84 | 1-42 | 30:70 | Styrene-acrylic | Cyan | 1 | 89 | ⊙ |
| 1-85 | 1-43 | 30:70 | Styrene-acrylic | Cyan | 1 | 89 | ⊙ |
| 1-86 | 1-44 | 30:70 | Styrene-acrylic | Cyan | 1 | 89 | ⊙ |
| 1-87 | 1-45 | 30:70 | Styrene-acrylic | Cyan | 1 | 87 | ⊙ |
| 1-88 | 1-46 | 30:70 | Styrene-acrylic | Cyan | 1 | 89 | ⊙ |
| 1-89 | 1-47 | 30:70 | Styrene-acrylic | Cyan | 1 | 87 | ⊙ |
| 1-90 | 1-48 | 30:70 | Styrene-acrylic | Cyan | 1 | 73 | ⊙ |
| 1-91 | 1-49 | 30:70 | Styrene-acrylic | Cyan | 1 | 79 | ⊙ |
| 1-92 | 1-50 | 30:70 | Styrene-acrylic | Cyan | 1 | 77 | ⊙ |
| 1-93 | 1-51 | 30:70 | Styrene-acrylic | Cyan | 1 | 80 | ⊙ |
| 1-94 | 1-55 | 30:70 | Styrene-acrylic | Cyan | 1 | 74 | ⊙ |
| 1-95 | 1-56 | 30:70 | Styrene-acrylic | Cyan | 1 | 71 | ⊙ |
| 1-97 | 1-70 | 30:70 | Styrene-acrylic | Cyan | 1 | 80 | ⊙ |
| 1-98 | 1-72 | 30:70 | Styrene-acrylic | Cyan | 1 | 82 | ⊙ |
| 1-99 | 1-74 | 30:70 | Styrene-acrylic | Cyan | 1 | 82 | ⊙ |
| 1-100 | 1-1 | 10:90 | Styrene-acrylic | Cyan | 1 | 86 | ⊙ |
| 1-101 | 1-1 | 50:50 | Styrene-acrylic | Cyan | 1 | 90 | ⊙ |
| 1-102 | 1-1 | 70:30 | Styrene-acrylic | Cyan | 1 | 83 | ⊙ |
| 1-103 | 1-1 | 90:10 | Styrene-acrylic | Cyan | 1 | 86 | ⊙ |
| 1-104 | 1-1 | 30:70 | Polyester | Cyan | 1 | 89 | ⊙ |
| 1-105 | 1-1 | 10:90 | Polyester | Cyan | 1 | 85 | ⊙ |
| 1-106 | 1-1 | 50:50 | Polyester | Cyan | 1 | 89 | ⊙ |
| 1-107 | 1-1 | 30:70 | Styrene-acrylic | Cyan | 2 | 92 | ⊙ |
| 1-108 | 1-1 | 30:70 | Styrene-acrylic | Cyan | 3 | 93 | ⊙ |
| Comparative Example 1-2 | 1-75 (Azobenzene compound) | 30:70 | Styrene-acrylic | Cyan | 1 | 79 | X |

The "azomethine derivative" in Table 1-3 (Table 1-3-1 and Table 1-3-2) refers to a compound having an azomethine part as represented by the Chemical Formula 1. The number of a compound refers to the number of a compound having an azomethine part in Table 1-1 (Table 1-1-1 to Table 1-1-3) and Table 1-2 (Table 1-2-1 to Table 1-2-2). The "Azomethine derivative:binder resin (mass ratio)" in Table 1-3 (Table 1-3-1 and Table 1-3-2) represents the compound having an azomethine part:binder resin (mass ratio) in the toner. The "azomethine derivative:binder resin (mass ratio)" of Comparative Example 1-2 in Table 1-3-2 represents "azobenzene compound:binder resin (mass ratio)".

As is obvious from Table 1-3 (Table 1-3-1 and Table 1-3-2), the toners of Examples 1-51 to 1-108 exhibited high fixability and excellent color reproducibility. On the other hand, it was found that the toner of Comparative Example 1-2 had satisfactory fixability but low color reproducibility. Since the light source of ultraviolet radiation and the conditions for ultraviolet irradiation used in the fixability test were constant throughout Examples 1-51 to 1-108 and Comparative Example 1-2, it can be said that in the toners of Examples, the effects provided by the compound having an azomethine part, by which the toner is reversibly fluidized and non-fluidized by being irradiated with light and does not undergo noticeable coloration, are sufficiently exhibited compared to the toner of Comparative Example.

When a comparison of the fixing apparatuses is made, it could be seen that rather than using the fixing apparatus of No. 1 in which the same toner 1-1 was used and irradiated with ultraviolet radiation under the same conditions while no pressing member was used, superior fixability is obtained by using the fixing apparatus of No. 2 in which the toner was pressed with a pressing member, or further, by using the fixing apparatus of No. 3 in which the toner was pressed while heated with a pressing member (comparison of Example 1-51, 1-107, and 1-108).

In view of the compounds used in Examples 1-51 to 1-99 in which the compound having an azomethine part in the toner was changed, the detailed reason is not clearly known; however, suitable compounds are compounds No. 1-1, 1-4 to 1-5, 1-9, 1-12, 1-19 to 1-23, 1-30 to 1-35, and 1-40 to 1-47.

Second Embodiment

The effects of the second embodiment of the present invention will be described using the following Examples and Comparative Examples. However, the technical scope of the present invention is not intended to be limited to the following Examples only.

Compounds 2-1 to 2-59 and the compound of Comparative Example 2-1 were synthesized, and the activation energy thereof was calculated. The compounds 2-1 to 2-11 and 2-13 to 2-59 and the compound having an azomethine part used in Comparative Example 2-1 were synthesized in the same manner as in the synthesis of the following compound 2-12. The synthesis method of compound 2-12 will be described as a representative example.

Synthesis of Compound Having Azomethine Part

Synthesis of Compound 2-12

[Chemical Formula 22]

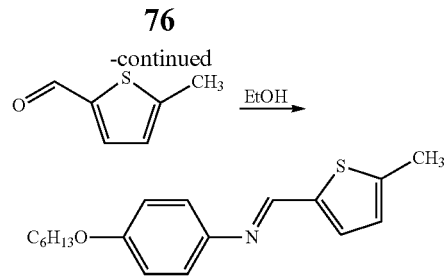

Into a 100-ml four-necked flask equipped with a cooling tube, a nitrogen inlet tube, and a thermometer, 4-hexyloxybenzeneamine (4-hexyloxyaniline) (7.7 mmol), 5-methylthiophene-2-carboxyaldehyde (7.7 mmol), and 20 ml of ethanol were introduced, and the mixture was heated and stirred. The reaction liquid was suction-filtered, and a powder thus obtained was washed with cold ethanol. Furthermore, recrystallization was performed from methanol/ethanol, and compound 2-12 as a target substance was obtained at a yield of 42%.

Production of the compound 2-12 was confirmed by $^1$H-NMR. $^1$H NMR (400 MHz, CDCl$_3$); 8.35 ppm (s, 1H, CH=N), 7.39 ppm (d, 2H, aryl), 7.08 ppm (d, 1H, thiophene), 6.96 ppm (d, 2H, aryl), 6.67 ppm (d, 2H, thiophene), 4.11 ppm (t, 2H, methylene), 2.44 ppm (s, 3H, methyl), 1.80 ppm (m, 2H, methylene), 1.47 ppm (m, 2H, methylene), 1.37 ppm (m, 4H, methylene), 0.89 ppm (t, 3H, methyl).

Other compounds were also synthesized by a similar method using the respective corresponding raw materials, and the compounds 2-1 to 2-59 and the compound having an azomethine part of Comparative Example 2-1 were obtained. Furthermore, production of the intended compounds was similarly confirmed by $^1$H-NMR.

Comparative Example 2-2: Synthesis of Azobenzene Compound

A compound represented by the following Chemical Formula (2) (azobenzene compound) was obtained in the same manner as in the "(1-1-1) Synthesis of UV-softening material A" described in paragraphs "0217" to "0224" of Japanese Patent Application Laid-Open No. 2014-191078. Similarly to the compound having an azomethine part described above, production of the compound was confirmed by $^1$H-NMR, and it was found that the intended compound was obtained.

[Chemical Formula 23]

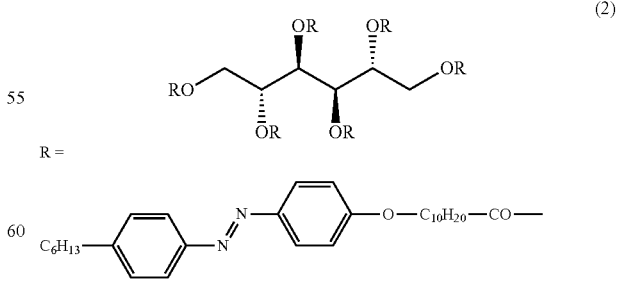

[Theoretical Calculation]

The calculation of the most stable molecular structure (molecular structure of the cis-form), the total energy of the cis-form, the molecular structure of the transition state, and the total energy of the transition state of the compounds 2-1 to 2-59 of Examples and the compound of Comparative Example 2-1 was carried out using Gaussian 16 (Revision B.01, M. J. Frisch, G. W. Trucks, H. B. Schlegel, G. E. Scuseria, M. A. Robb, J. R. Cheeseman, G. Scalmani, V. Barone, G. A. Petersson, H. Nakatsuji, X. Li, M. Caricato, A. V. Marenich, J. Bloino, B. G. Janesko, R. Gomperts, B. Mennucci, H. P. Hratchian, J. V. Ortiz, A. F. Izmaylov, J. L. Sonnenberg, D. Williams-Young, F. Ding, F. Lipparini, F. Egidi, J. Goings, B. Peng, A. Petrone, T. Henderson, D. Ranasinghe, V. G. Zakrzewski, J. Gao, N. Rega, G. Zheng, W. Liang, M. Hada, M. Ehara, K. Toyota, R. Fukuda, J. Hasegawa, M. Ishida, T. Nakajima, Y. Honda, O. Kitao, H. Nakai, T. Vreven, K. Throssell, J. A. Montgomery, Jr., J. E. Peralta, F. Ogliaro, M. J. Bearpark, J. J. Heyd, E. N. Brothers, K. N. Kudin, V. N. Staroverov, T. A. Keith, R. Kobayashi, J. Normand, K. Raghavachari, A. P. Rendell, J. C. Burant, S. S. Iyengar, J. Tomasi, M. Cossi, J. M. Millam, M. Klene, C. Adamo, R. Cammi, J. W. Ochterski, R. L. Martin, K. Morokuma, O. Farkas, J. B. Foresman, and D. J. Fox, Gaussian, Inc., Wallingford Conn., 2016) software manufactured by Gaussian, Inc. in the USA. As the calculation technique, a density functional method (B3LYP/6-31G(d)) was used. From the calculation value thus obtained, the value of the activation energy Ea was determined according to the Formula (1).

Regarding the molecular structure of the cis-form, the most stable molecular structure, that is, a molecular structure having the lowest total energy, of an isomer represented by the General Formula (3) was calculated, and this total energy was designated as the total energy of the cis-form. Regarding the molecular structure of the transition state, for the transition state represented by the General Formula (2), the saddle point of the corresponding molecular structure was calculated, and the total energy obtained at this time was designated as the total energy of the transition state. From the calculation value obtained as such, the value of the activation energy Ea was determined according to the Formula (1).

The structures and the activation energy of the compounds 2-1 to 2-59 of Examples and the compound obtained in Comparative Example 2-1 are shown in the following Table 2-1 (Tables 2-1-1 to 2-1-14).

[Photoresponsive Adhesion Test]

The changes in the adhesiveness concomitant to light irradiation of the compounds 2-1 to 2-59 and the compounds synthesized in Comparative Examples 2-1 and 2-2 were evaluated in the following photoresponsive adhesion test using an apparatus illustrated in FIG. 4. As shown in FIG. 4, 2 mg of a compound was mounted on a cover glass 1 measuring 18 mm on each of four sides, within a radius of 6 mm from the center of the glass, and a cover glass 2 having the same size was covered at a position shifted by about 4 mm in a direction parallel to the cover glass 1 so as to cover the entire compound. This was heated to melt the sample, and thus the cover glass 1 and the cover glass 2 were adhered. Each of the samples thus obtained was subjected to a non-fluidity→fluidity test as described below and was subsequently subjected to a fluidity→non-fluidity test as described below.

<Non-Fluidity→Fluidity Test (Fluidization Test)>

The part (A) shown in FIG. 4 was fixed to a holder with Cellophane tape, and a vinyl string 30 cm long loaded with a 100-g weight was fixed to the part (C) with Cellophane tape. The part (B) was irradiated with light having a wavelength of 365 nm in an amount of irradiation of 30 J/cm$^2$, it was checked whether the cover glass 2 would come off from the cover glass 1, and the result was judged according to the following evaluation criteria. The results thus obtained are shown in Table 2-2.

—Evaluation Criteria for Non-Fluidity→Fluidity Test (Fluidization Test)—

○: The cover glass 2 completely came off from the cover glass 1.

Δ: The cover glass 2 was shifted.

x: The cover glass 2 did not move.

<Fluidity→Non-Fluidity Test (Non-Fluidization Test)>

After completion of the non-fluidity→fluidity test, a sample in which the cover glass 2 completely came off and a sample in which the cover glass 2 was shifted were subjected to the following experiment. Meanwhile, for the sample in which the cover glass 2 was shifted, the cover glasses 1 and 2 were detached with hands After the sample was left to stand for 5 minutes (for the 5 minutes, left to stand in a natural environment, that is, at room temperature (in the range of 25±15° C.)) from the completion of light irradiation of the non-fluidity→fluidity test, a cover glass 3 (having the same size as the cover glasses 1 and 2) was mounted so as to cover the sample portion (part (B)) of the cover glass 1 used in the above-described test, it was checked whether the cover glass 1 and the cover glass 3 would adhere, and the result was judged according to the following evaluation criteria. The results thus obtained are shown in Table 2-2.

—Evaluation Criteria for Fluidity→Non-Fluidity Test (Non-Fluidization Test)—

○: Did not adhere (non-fluidized)

Δ: Partially adhered (a fluidized state was maintained in some portion)

x: Adhered (a fluidized state was maintained).

TABLE 2

| Compound No. | $Z_1$ | $Z_2$ | $R_1$ | $R_2$ | A $R_3$ | $R_4$ | $R_5$ | $R_6$ | $R_7$ | B $R_8$ | $R_9$ | $R_{10}$ | Ea (kJ/mol) |
|---|---|---|---|---|---|---|---|---|---|---|---|---|---|
| 2-1 | N | CH | H | H | $OC_6H_{13}$ | H | H | H | H | $OC_6H_{13}$ | H | H | 62.83 |
| 2-2 | N | CH | H | H | $OC_6H_{13}$ | H | H | H | $CH_3$ | $OC_6H_{13}$ | H | H | 63.08 |
| 2-3 | N | CH | H | H | $OC_4H_9$ | H | H | H | $CH_3$ | $OC_4H_9$ | H | H | 62.86 |
| 2-4 | N | CH | H | $CH_3$ | $OC_6H_{13}$ | H | H | H | H | $N(CH_3)_2$ | H | H | 71.21 |
| 2-5 | N | CH | H | $CH_3$ | $OC_6H_{13}$ | H | H | H | H | $N(C_2H_5)_2$ | H | H | 63.10 |
| 2-6 | N | CH | $CH_3$ | H | $OC_6H_{13}$ | H | H | H | H | $N(C_2H_5)_2$ | H | H | 71.22 |
| 2-7 | N | CH | H | H | $OC_6H_{13}$ | H | H | H | H | $N(C_3H_7)_2$ | H | H | 72.60 |
| 2-8 | N | CH | H | H | $OC_6H_{13}$ | H | H | H | H | $NH_2$ | H | H | 71.84 |
| 2-9 | N | CH | H | H | $OC_{12}H_{25}$ | H | H | H | H | $N(C_2H_5)_2$ | H | H | 62.69 |
| 2-10 | N | CH | H | H | $N(C_2H_5)_2$ | H | H | H | H | $N(C_2H_5)_2$ | H | H | 67.99 |

| Compound No. | $Z_1$ | $Z_2$ | $R_1$ | $R_2$ | A $R_3$ | $R_4$ | $R_5$ | X | $R_{11}$ | $R_{12}$ | B $R_{12}$ | $R_{13}$ | $R_{14}$ | Ea (kJ/mol) |
|---|---|---|---|---|---|---|---|---|---|---|---|---|---|---|
| 2-11 | N | CH | H | H | $OC_6H_{13}$ | H | H | O | — | — | H | H | H | 73.87 |
| 2-12 | N | CH | H | H | $OC_6H_{13}$ | H | H | S | — | — | $CH_3$ | H | H | 68.99 |
| 2-13 | N | CH | H | H | $OC_6H_{13}$ | H | H | S | — | — | $OCH_3$ | H | H | 69.28 |
| 2-14 | N | CH | H | H | $OC_6H_{13}$ | H | H | S | — | — | $N(CH_3)_2$ | H | H | 70.10 |
| 2-15 | N | CH | H | H | $C_6H_{13}$ | H | H | S | — | — | H | H | H | 65.68 |
| 2-16 | N | CH | H | H | $N(CH_3)_2$ | H | H | S | — | — | $C_4H_9$ | H | H | 68.17 |
| 2-17 | N | CH | H | H | $N(CH_3)_2$ | H | H | S | — | — | $C_6H_{13}$ | H | H | 68.16 |

TABLE 2-continued

| Compound No. | $Z_1$ | $Z_2$ | $R_1$ | $R_2$ | $R_3$ | $R_4$ | $R_5$ | X | $R_{11}$ | $R_{12}'$ | $R_{13}'$ | $R_{14}'$ | Ea (kJ/mol) |
|---|---|---|---|---|---|---|---|---|---|---|---|---|---|
| 2-18 | N | CH | H | H | $OC_6H_{13}$ | H | H | $NR_{11}$ | $CH_3$ | H | H | H | 72.39 |
| 2-19 | N | CH | H | H | $C_6H_{13}$ | H | H | $NR_{11}$ | $CH_3$ | H | H | H | 68.15 |
| 2-20 | N | CH | H | H | $N(C_2H_5)_2$ | H | H | $NR_{11}$ | $CH_3$ | H | H | H | 72.16 |
| 2-21 | N | CH | H | H | $OC_6H_{13}$ | H | H | $NR_{11}$ | H | $C_6H_{13}$ | H | H | 73.10 |
| 2-22 | N | CH | H | H | $OC_4H_9$ | H | H | $NR_{11}$ | H | H | H | H | 72.74 |
| 2-23 | N | CH | H | H | $OC_2H_5$ | H | H | $NR_{11}$ | H | $CH_3$ | H | H | 72.33 |
| 2-24 | N | CH | H | H | $OC_6H_{13}$ | H | H | $NR_{11}$ | H | H | H | H | 72.76 |

A

B

| Compound No. | $Z_1$ | $Z_2$ | $R_1$ | $R_2$ | $R_3$ | $R_4$ | $R_5$ | X | $R_{11}$ | Ea (kJ/mol) |
|---|---|---|---|---|---|---|---|---|---|---|
| 2-25 | N | CH | H | H | $OC_6H_{13}$ | H | H | $NR_{11}$ | $C_6H_{13}$ | 71.22 |
| 2-26 | N | CH | H | H | $OC_4H_9$ | H | H | $NR_{11}$ | H | 71.10 |
| 2-27 | N | CH | H | H | $OC_2H_5$ | H | H | $NR_{11}$ | $CH_3$ | 71.16 |
| 2-28 | N | CH | H | H | $OC_6H_{13}$ | H | H | $NR_{11}$ | H | 71.12 |

A

B

| Compound No. | $Z_1$ | $Z_2$ | $R_1$ | $R_2$ | $R_3$ | $R_4$ | $R_5$ | $R_{15}$ | $R_{16}$ | $R_{17}$ | Ea (kJ/mol) |
|---|---|---|---|---|---|---|---|---|---|---|---|
| 2-29 | N | CH | H | H | $OC_6H_{13}$ | H | H | H | H | H | 71.84 |
| 2-30 | N | CH | H | H | $OC_4H_9$ | H | H | $C_4H_9$ | H | H | 71.84 |
| 2-31 | N | CH | $CH_3$ | H | $OC_2H_5$ | H | H | H | H | H | 72.32 |
| 2-32 | N | CH | H | H | $C_6H_{13}$ | H | H | H | H | H | 67.58 |
| 2-33 | N | CH | H | H | $N(CH_3)_2$ | H | H | H | H | H | 70.81 |

TABLE 2-continued

![Structure A: substituted phenyl with R1-R5 connected via N=N (Z1=Z2) to imidazole ring with R18, R19, R20]

| Compound No. | Z₁ | Z₂ | R₁ | R₂ | R₃ | R₄ | R₅ | R₁₈ | R₁₉ | R₂₀ | Ea (kJ/mol) |
|---|---|---|---|---|---|---|---|---|---|---|---|
| 2-34 | CH | CH | H | H | OC₆H₁₃ | H | H | CH₃ | H | H | 66.74 |
| 2-35 | CH | N | H | H | C₆H₁₃ | H | H | CH₃ | H | H | 65.33 |
| 2-36 | CH | N | H | H | N(C₂H₅)₂ | H | H | CH₃ | H | H | 75.02 |

|       |    |    |    | A  |    |    |    |     | B   |     |         |
|-------|----|----|----|----|----|----|----|-----|-----|-----|---------|
| Compound No. | Z₁ | Z₂ | R₁ | R₂ | R₃ | R₄ | R₅ | R₁₈ | R₁₉ | R₂₀ | Ea (kJ/mol) |
| 2-37 | N  | CH | H  | H  | OC₈H₁₇ | H | H | H    | H     | H | 71.95 |
| 2-38 | N  | CH | H  | H  | OC₆H₁₃ | H | H | CH₃  | H     | H | 71.25 |
| 2-39 | N  | CH | H  | H  | C₆H₁₃  | H | H | H    | H     | H | 67.97 |
| 2-40 | N  | CH | H  | H  | OC₂H₁₃ | H | H | CH₃  | H     | H | 73.06 |
| 2-41 | N  | CH | H  | CH₃| N(C₂H₅)₂ | H | H | H  | C₂H₅  | H | 78.81 |
| 2-42 | CH | N  | H  | H  | OC₆H₁₃ | H | H | H    | H     | H | 71.64 |
| 2-43 | CH | N  | H  | H  | C₄H₉   | H | H | H    | H     | H | 72.89 |

![Structure A: trisubstituted phenyl with R1-R5 and methyl; B: indole variants 1, 2, 3]

| Compound No. | Z₁ | Z₂ | R₁ | R₂ | R₃ | R₄ | R₅ | B | Ea (kJ/mol) |
|---|---|---|---|---|---|---|---|---|---|
| 2-44 | N  | CH | H | CH₃ | OC₆H₁₃    | H | H | 2 | 64.41 |
| 2-45 | N  | CH | H | CH₃ | OC₆H₁₃    | H | H | 3 | 74.61 |
| 2-46 | N  | CH | H | H   | N(C₂H₅)₂  | H | H | 1 | 68.76 |
| 2-47 | CH | N  | H | H   | OC₆H₁₃    | H | H | 1 | 63.92 |
| 2-48 | CH | N  | H | H   | C₆H₁₃     | H | H | 1 | 63.44 |

B structures:
1: 5-methyl-1H-indole
2: 4-methyl-2,3-dihydro-1H-indole
3: 3-methyl-1H-indole TABLE 2-continued

| Compound No. | A | | | | | | B | | Ea (kJ/mol) |
|---|---|---|---|---|---|---|---|---|---|
| | $Z_1$ | $Z_2$ | $R_1$ | $R_2$ | $R_3$ | $R_4$ | $R_5$ | $R_{21}$ | |
| 2-49 | N | CH | H | H | $N(C_2H_5)_2$ | H | H | $C_6H_{13}$ | 62.26 |

| Compound No. | A | | | | | | B | | | | Ea (kJ/mol) |
|---|---|---|---|---|---|---|---|---|---|---|---|
| | $Z_1$ | $Z_2$ | X | $R_{12}$ | $R_{13}$ | $R_{14}$ | $R_{15}$ | $R_{16}$ | $R_{17}$ | | |
| 2-50 | CH | N | S | $C_6H_{13}$ | H | H | $CH_3$ | H | H | | 76.76 |

| Compound No. | A | | | | | | B | | | | Ea (kJ/mol) |
|---|---|---|---|---|---|---|---|---|---|---|---|
| | $Z_1$ | $Z_2$ | X | $R_{11}$ | $R_{12}$ | $R_{13}$ | $R_{14}$ | $R_{18}$ | $R_{19}$ | $R_{20}$ | |
| 2-51 | N | CH | S | — | $C_6H_{13}$ | H | H | $CH_3$ | H | H | 66.42 |
| 2-52 | CH | N | S | — | $C_2H_5$ | H | H | $OC_4H_9$ | H | H | 76.64 |
| 2-53 | N | CH | $NR_{11}$ | H | $C_{10}H_{21}$ | H | H | H | H | H | 65.85 |
| 2-54 | CH | N | $NR_{11}$ | H | $CH_3$ | H | H | $CH_3$ | H | H | 83.45 |

TABLE 2-continued
| Compound No. | Z₁ | Z₂ | A | | | | | | B | Ea (kJ/mol) |
|---|---|---|---|---|---|---|---|---|---|---|
| | | | | X | R₁₁ | R₁₂ | R₁₃ | R₁₄ | | |
| 2-55 | CH | N | 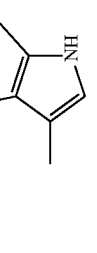 | NR₁₁ | H | CH₃ | H | H | 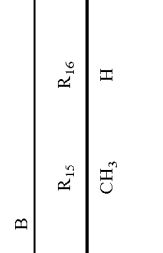 | 63.23 |
| Compound No. | Z₁ | Z₂ | A | | | | B | | | | Ea (kJ/mol) |
|---|---|---|---|---|---|---|---|---|---|---|---|
| | | | | R₁₅ | R₁₆ | R₁₇ | | R₁₅ | R₁₆ | R₁₇ | |
| 2-56 | N | CH | 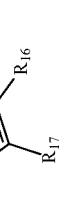 | CH₃ | H | H |  | CH₃ | H | H | 73.77 |
| Compound No. | Z₁ | Z₂ | A | | | | B | | | | Ea (kJ/mol) |
|---|---|---|---|---|---|---|---|---|---|---|---|
| | | | | R₁₅ | R₁₆ | R₁₇ | | R₁₈ | R₁₉ | R₂₀ | |
| 2-57 | N | CH | 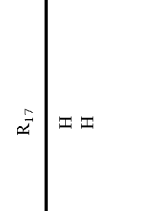 | C₄H₉ | H | H | 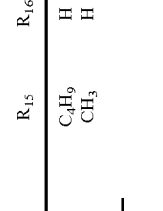 | C₄H₉ | H | H | 64.35 |
| 2-58 | CH | N | | CH₃ | H | H | | CH₃ | H | H | 81.32 |

TABLE 2-continued

| Compound No. | A | | | | | | | | | B | | | | | Ea (kJ/mol) |
|---|---|---|---|---|---|---|---|---|---|---|---|---|---|---|---|
| | $Z_1$ | $Z_2$ | $R_{15}$ | $R_{16}$ | $R_{17}$ | | | | | | | | | | |
| 2-59 | N | CH | CH$_3$ | H | H | | | | | (3-methyl-1H-indol-yl structure) | | | | | 79.38 |

| | A | | | | | | | B | | | | | Ea (kJ/mol) |
|---|---|---|---|---|---|---|---|---|---|---|---|---|---|
| | $Z_1$ | $Z_2$ | $R_1$ | $R_2$ | $R_3$ | $R_4$ | $R_5$ | $R_6$ | $R_7$ | $R_8$ | $R_9$ | $R_{10}$ | |
| Comparative Example 2-1 | N | CH | H | H | H | H | H | H | H | H | H | H | 56.93 |

TABLE 2-2

| Compound No. | Photoresponsive adhesion test | |
| --- | --- | --- |
| | Fluidization test | Non-fluidization test |
| 2-1 | ○ | ○ |
| 2-2 | ○ | ○ |
| 2-3 | ○ | ○ |
| 2-4 | ○ | ○ |
| 2-5 | ○ | ○ |
| 2-6 | ○ | ○ |
| 2-7 | ○ | ○ |
| 2-8 | ○ | ○ |
| 2-9 | ○ | ○ |
| 2-10 | ○ | ○ |
| 2-11 | ○ | ○ |
| 2-12 | ○ | ○ |
| 2-13 | ○ | ○ |
| 2-14 | ○ | ○ |
| 2-15 | ○ | ○ |
| 2-16 | ○ | ○ |
| 2-17 | ○ | ○ |
| 2-18 | ○ | ○ |
| 2-19 | ○ | ○ |
| 2-20 | ○ | ○ |
| 2-21 | ○ | ○ |
| 2-22 | ○ | ○ |
| 2-23 | ○ | ○ |
| 2-24 | ○ | ○ |
| 2-25 | ○ | ○ |
| 2-26 | ○ | ○ |
| 2-27 | ○ | ○ |
| 2-28 | ○ | ○ |
| 2-29 | ○ | ○ |
| 2-30 | ○ | ○ |
| 2-31 | ○ | ○ |
| 2-32 | ○ | ○ |
| 2-33 | ○ | ○ |
| 2-34 | ○ | ○ |
| 2-35 | ○ | ○ |
| 2-36 | ○ | ○ |
| 2-37 | ○ | ○ |
| 2-38 | ○ | ○ |
| 2-39 | ○ | ○ |
| 2-40 | ○ | ○ |
| 2-41 | ○ | ○ |
| 2-42 | ○ | ○ |
| 2-43 | ○ | ○ |
| 2-44 | ○ | ○ |
| 2-45 | ○ | ○ |
| 2-46 | ○ | ○ |
| 2-47 | ○ | ○ |
| 2-48 | ○ | ○ |
| 2-49 | ○ | ○ |
| 2-50 | ○ | ○ |
| 2-51 | ○ | ○ |
| 2-52 | ○ | ○ |
| 2-53 | ○ | ○ |
| 2-54 | ○ | ○ |
| 2-55 | ○ | ○ |
| 2-56 | ○ | ○ |
| 2-57 | ○ | ○ |
| 2-58 | ○ | ○ |
| 2-59 | ○ | ○ |
| Comparative Example 2-1 | X | X |
| Comparative Example 2-2 (azobenzene compound) | ○ | X |

As is obvious from Table 2-2, it was found that the compounds 2-1 to 2-59 of Examples are all fluidized by light irradiation and are reversibly non-fluidized. In contrast, it was found that in the compound of Comparative Example 2-1 in which the activation energy Ea for an isomerization reaction from the cis-form to the trans-form is lower than 60 kJ/mol, fluidization caused by light irradiation and non-fluidization do not occur. Furthermore, in the azobenzene compound according to Comparative Example 2-2, reversible non-fluidization after fluidization was not recognized.

[Production of Toner]
[Production of Binder Resin]
(Production of Styrene-Acrylic Resin Particle Dispersion 1 Containing Styrene-Acrylic Resin 1)
(First Stage Polymerization)

Into a reaction vessel equipped with a stirring apparatus, a temperature sensor, a cooling tube, and a nitrogen inlet apparatus, a solution obtained by dissolving 8 parts by mass of sodium dodecyl sulfate in 3,000 parts by mass of ion-exchanged water was introduced, and while the solution was stirred at a stirring rate of 230 rpm under a nitrogen gas stream, the internal temperature was increased to 80° C. After temperature increase, a solution obtained by dissolving 10 parts by mass of potassium persulfate in 200 parts by mass of ion-exchanged water was added thereto, the liquid temperature was adjusted to 80° C. again, and a polymerizable monomer solution containing 480 parts by mass of styrene, 250 parts by mass of n-butyl acrylate, 68.0 parts by mass of methacrylic acid, and 16.0 parts by mass of n-octyl-3-mercaptopropionate was added dropwise thereto over one hour. Subsequently, the mixture was heated and stirred for 2 hours at 80° C., and thereby polymerization was carried out. Thus, a styrene-acrylic resin particle dispersion (1A) containing styrene-acrylic resin particles (1a) was prepared.

(Second Stage Polymerization)

Into a reaction vessel equipped with a stirring apparatus, a temperature sensor, a cooling tube, and a nitrogen inlet apparatus, a solution obtained by dissolving 7 parts by mass of sodium polyoxyethylene-2-dodecyl ether sulfate in 800 parts by mass of ion-exchanged water was introduced, the solution was heated to 98° C., and then 260 parts by mass of the above-mentioned styrene-acrylic resin particle dispersion (1A), and a polymerizable monomer solution obtained by dissolving 245 parts by mass of styrene, 120 parts by mass of n-butyl acrylate, 1.5 parts by mass of n-octyl-3-mercaptopropionate, and 67 parts by mass of paraffin wax "HNP-11" (manufactured by Nippon Seiro Co., Ltd.) as a release agent at 90° C. were added thereto. The mixture was mixed and dispersed for one hour using a mechanical dispersing machine "CREARMIX" (manufactured by M Technique Co., Ltd.) having a circulation path, and thereby a dispersion including emulsion particles (oil droplets) was prepared.

Next, an initiator solution obtained by dissolving 6 parts by mass of potassium persulfate in 200 parts by mass of ion-exchanged water was added to this dispersion, and polymerization was carried out by heating and stirring this system over one hour at 82° C. Thus, a styrene-acrylic resin particle dispersion (1B) containing styrene-acrylic resin particles (1b) was prepared.

(Third Stage Polymerization)

A solution obtained by dissolving 11 parts by mass of potassium persulfate in 400 parts by mass of ion-exchanged water was added to the above-described styrene-acrylic resin particle dispersion (1B), and under the temperature conditions of 82° C., a polymerizable monomer solution containing 435 parts by mass of styrene, 130 parts by mass of n-butyl acrylate, 33 parts by mass of methacrylic acid, and 8 parts by mass of n-octyl-3-mercaptopropionate was added dropwise thereto over one hour. After completion of the dropwise addition, the mixture was heated and stirred over 2 hours to thereby perform polymerization, and then the liquid was cooled to 28° C. Thus, a styrene-acrylic resin particle dispersion 1 containing a styrene-acrylic resin 1 was obtained. Furthermore, the glass transition point Tg of this styrene-acrylic resin 1 was measured, and the glass transition point was 45° C.

(Production of Polyester Resin Particle Dispersion 1 Containing Polyester Resin 1)

Into a four-necked flask having a capacity of 10 liters and equipped with a nitrogen inlet tube, a dehydrating tube, a stirring device, and a thermocouple, 524 parts by mass of a bisphenol A propylene oxide 2-mol adduct, 105 parts by mass of terephthalic acid, 69 parts by mass of fumaric acid, and 2 parts by mass of tin octoate (esterification catalyst) were introduced, and a polycondensation reaction was carried out for 8 hours at a temperature of 230° C. Furthermore, the polycondensation reaction was continued for one hour at 8 kPa, subsequently the liquid was cooled to 160° C., and a polyester resin 1 was obtained. 100 parts by mass of the polyester resin 1 was pulverized with "ROUNDEL MILL Model: RM" (manufactured by Tokuju Corporation) and was mixed with 638 parts by mass of a 0.26 mass % aqueous solution of sodium lauryl sulfate that had been produced in advance. While being stirred, the mixture was ultrasonically dispersed using an ultrasonic homogenizer "US-150T" (manufactured by Nissei Corporation) with V-LEVEL at 300 µA for 30 minutes, and thus a polyester resin particle dispersion 1 was obtained. Furthermore, the glass transition point Tg of this polyester resin 1 was measured, and the glass transition point was 42° C.

[Production of Toner 2-1]

(Preparation of Carbon Black Dispersion)

11.5 parts by mass of sodium n-dodecyl sulfate was dissolved in 160 parts by mass of pure water, 20 parts by mass of carbon black "MOGUL L (manufactured by Cabot Corporation)" was slowly added thereto, and then a carbon black dispersion was prepared using "CLEARMIX (registered trademark) W-MOTION CLM-0.8 (manufactured by M Technique Co., Ltd.)".

(Preparation of Azomethine Part-Containing Compound Particle Dispersion 1)

80 parts by mass of dichloromethane and 20 parts by mass of the compound 2-2 were mixed and stirred while being heated at 50° C., and a liquid containing the compound 2-2 was obtained. To 100 parts by mass of this liquid, a mixed liquid of 99.5 parts by mass of distilled water that had been warmed to 50° C. and 0.5 parts by mass of a 20 mass % aqueous solution of sodium dodecyl benzenesulfonate was added. Subsequently, the mixture was stirred for 20 minutes at 16,000 rpm using a homogenizer equipped with a shaft generator 18F (manufactured by Heidolph Instruments GmbH & CO. KG) to emulsify the mixture, and thus an emulsion 1 of the compound having an azomethine part was obtained.

The emulsion 1 of the compound having an azomethine part thus obtained was introduced into a separable flask, and while nitrogen was supplied into the gas phase, the emulsion was heated and stirred for 90 minutes at 40° C. to remove the organic solvent. Thereby, an azomethine part-containing compound particle dispersion 1 was obtained.

(Aggregation and Fusion)

504 parts by mass in terms of the solid content of the styrene-acrylic resin particle dispersion 1 produced as described above, 216 parts by mass in terms of the solid content of the azomethine part-containing compound particle dispersion 1, 900 parts by mass of ion-exchanged water, and 70 parts by mass in terms of the solid content of the carbon black dispersion were introduced into a reaction apparatus equipped with a stirring apparatus, a temperature sensor, and a cooling tube. The temperature inside the container was maintained at 30° C., a 5 mol/liter aqueous solution of sodium hydroxide was added thereto to adjust the pH to 10.

Next, an aqueous solution obtained by dissolving 2 parts by mass of magnesium chloride hexahydrate in 1,000 parts by mass of ion-exchanged water was added dropwise thereto over 10 minutes under stirring, and then temperature increase was initiated. This system was heated up to 70° C. for 60 minutes, 70° C. was maintained, and a particle growth reaction was continued. The particle size of associated particles was measured in this state using a "MULTISIZER-3" (manufactured by Beckman Coulter, Inc.), and at the time point when the volume based median diameter (D50) became 6.5 µm, an aqueous solution obtained by dissolving 190 parts by mass of sodium chloride in 760 parts by mass of ion-exchanged water was added thereto to terminate particle growth. The mixture was stirred for one hour at 70° C., subsequently temperature increase was further carried out, and the mixture was heated and stirred in a state of 75° C. to thereby implement fusion of the particles. Subsequently, the mixture was cooled to 30° C., and thus a dispersion of toner base particles was obtained.

The dispersion of toner base particles obtained as described above was subjected to solid-liquid separation with a centrifuge, and a wet cake of the toner base particles was formed. The wet cake was washed with ion-exchanged water at 35° C. using the centrifuge until the electrical conductivity of the filtrate reached 5 µS/cm, subsequently the wet cake was transferred to "FLASH JET DRYER (manufactured by Seishin Enterprise Co., Ltd.)", and the wet cake was dried until the moisture amount reached 0.5% by mass. Thus, toner base particles were produced.

With respect to 100% by mass of the toner base particles thus obtained, 1% by mass of hydrophobic silica (number average primary particle size: 12 nm) and 0.3% by mass of hydrophobic titania (number average primary particle size: 20 nm) were added, and the mixture was mixed using a HENSCHEL MIXER (registered trademark). Thereby, a toner 2-1 was obtained.

[Production of Toners 2-2 to 2-51 and Toners of Comparative Examples 2-1 and 2-2]

Toners 2-2 to 2-51 and toners of Comparative Examples 2-1 and 2-2 were produced in the same manner as in the production of the toner 2-1 by appropriately changing according to the matters described in Tables 2-1 and 2-3. Specifically, with regard to toners 2-2 to 2-43, the toners 2-2 to 2-43 were produced in the same manner as in the case of the toner 2-1, except that the compound 2-2 was changed to the compounds described in Tables 2-1 and 2-3.

With regard to the toners 2-44 to 2-47, the compound 2-2 was changed to compound 2-12 in the production of the toner 2-1, and the amount of addition (in terms of the solid content) of the azomethine part-containing compound particle dispersion and the amount of addition (in terms of the solid content) of the styrene-acrylic resin particle dispersion 1 were regulated so as to obtain the ratio of the compound: binder resin as described in the following Table 2-3.

With regard to the toners 2-48 to 2-51, the compound 2-2 was changed to the compound 2-12 in the production of the toner 2-1, the styrene-acrylic resin particle dispersion 1 was changed to the polyester resin particle dispersion 1 produced as described above, and the amount of addition (in terms of the solid content) of the azomethine part-containing compound particle dispersion and the amount of addition (in terms of the solid content) of the polyester resin particle dispersion 1 were regulated so as to obtain the ratio of the compound:binder resin as described in the following Table 2-3.

With regard to the toner of Comparative Examples 2-1 and 2-2, the compound 2-2 was changed to the compounds of Comparative Examples 2-1 and 2-2, respectively, in the production of the toner 2-1 as described above.

[Production of Developer]

Each of the toners of Examples and Comparative Examples produced as described above was mixed with ferrite carrier particles having a volume average particle size of 30 μm and coated with a copolymer resin of cyclohexane methacrylate and methyl methacrylate (monomer mass ratio 1:1) such that the toner particle concentration would be 6% by mass, and developers 2-1 to 2-51 were obtained. Mixing was carried out for 30 minutes using a V-type mixer.

[Evaluation: Fixability Test]

Toner images were formed on plain paper as a recording medium using the developers thus obtained, and prints were obtained. Specifically, a developer was disposed between a pair of parallel flat plate (aluminum) electrodes, one electrode being provided with the developer and the other electrode being provided with gloss coated paper (basis weight: 128 g/m$^2$), while the developer was caused to slide by magnetic force, and the toner was developed at a gap between the electrodes of 0.5 mm under the conditions of the DC bias and the AC bias so that the amount of toner attachment would be 4 g/m$^2$. Thus, a toner image was formed on the surface of the plain paper, the toner image was fixed with a fixing apparatus, and thus a print was obtained.

Regarding the fixing apparatus, the following three kinds of apparatuses configured by appropriately modifying the apparatus illustrated in FIG. 2 were used.

Fixing apparatus No. 1: The compression unit 9 of FIG. 2 is absent, the wavelength of the ultraviolet light irradiated from the irradiation unit 40 is 365 nm (light source: LED light source having an emission wavelength of 365 nm±10 nm), and irradiation was carried out with an amount of irradiation of 8 and 12 J/cm$^2$. Furthermore, the toner softened by ultraviolet light irradiation was solidified (the compound was non-fluidized) and fixed in a natural environment, that is, in a state of being left to stand at room temperature (20° C.), until the toner reached the paper ejection unit 14 (see FIG. 1).

Fixing apparatus No. 2: There is the compression unit 9 of FIG. 2, the temperature of the pressing member 91 is 20° C., and the pressure at the time of pressing is 0.2 MPa. The light source and the amount of irradiation of the irradiation unit are similar to those of No. 1. Furthermore, the toner that had been softened by ultraviolet light irradiation was fixed by pressing by the pressing member 91, and subsequently, the toner was solidified (the compound was non-fluidized) in a state of leaving to stand at room temperature (20° C.), until the toner reached the paper ejection unit 14 (see FIG. 1).

Fixing apparatus No. 3: There is the compression unit 9 of FIG. 2, and the temperature of the pressing member 91 is 80° C. The light source and the amount of irradiation of the irradiation unit are similar to those of No. 1. Furthermore, the pressure at the time of pressing with the pressing member 91 is similar to that of No. 2. Furthermore, the toner that had been softened by ultraviolet light irradiation was further softened and fixed by pressing and heating by the pressing member 91. Subsequently, the toner was solidified (the compound was non-fluidized) in a state of being left to stand at room temperature (20° C.) until the toner reached the paper ejection unit 14 (see FIG. 1).

The print obtained as such was folded using a folding machine such that a load was applied, and then compressed air at 0.35 MPa was sprayed to the image portion. The fold line portion was evaluated by ranking according to the following evaluation criteria, and grade 3 or higher was considered acceptable.

6: There is no fold line at all.

5: There is only slight peeling along the fold line.

4: There is partial peeling along the fold line.

3: There is peeling in the form of a fine line along the fold line.

2: There is peeling in the form of a thick line along the fold line.

1: There is heavy peeling along the fold line.

[Evaluation of Color Reproducibility]

For the images of Examples and Comparative Examples obtained as described above, the color reproducibility was evaluated by a visual evaluation made by ten monitors according to the following evaluation criteria. Specifically, regarding the toners described in Examples, as samples for evaluation and comparison, toners excluding a photoresponsive compound were produced and developed as described above, and fixing was performed with a fixing apparatus No. 4 as described below.

Fixing Apparatus No. 4:

There is the compression unit 9 of FIG. 2, the temperature of the pressing member 91 is 150° C., the pressure at the time of pressing is 0.2 MPa, and light irradiation is not carried out.

The samples for evaluation and comparison and the samples described in Examples were shown in sequence to the ten monitors, and the monitors were questioned about whether the colors of two images were clearly different. The determination results based on the following evaluation criteria for color reproducibility are shown in the following Table 2-3.

—Evaluation Criteria for Color Reproducibility—

⊙: Two or fewer people answered that the colors were clearly different.

○: Three or four people answered that the colors were clearly different.

Δ: Five to seven people answered that the colors were clearly different.

x: Eight or more people answered that the colors were clearly different.

The configurations of the toners, the type of the fixing apparatus, and the evaluation results are shown in the following Table 2-3.

TABLE 2-3

| Toner No. | Compound No. | Compound:binder resin (mass ratio) | Binder resin | Colorant | Fixing apparatus | Folding evaluation (amount of irradiation) 8 J/cm² | 12 J/cm² | Color reproducibility |
|---|---|---|---|---|---|---|---|---|
| 2-1 | 2-2 | 30:70 | Styrene-acrylic resin | Black | 1 | 3 | 4 | ⊙ |
| 2-2 | 2-6 | 30:70 | Styrene-acrylic resin | Black | 1 | 3 | 4 | ⊙ |
| 2-3 | 2-8 | 30:70 | Styrene-acrylic resin | Black | 1 | 3 | 4 | ⊙ |
| 2-4 | 2-9 | 30:70 | Styrene-acrylic resin | Black | 1 | 3 | 4 | ⊙ |
| 2-5 | 2-12 | 30:70 | Styrene-acrylic resin | Black | 1 | 5 | 5 | ⊙ |
| 2-6 | 2-13 | 30:70 | Styrene-acrylic resin | Black | 1 | 5 | 5 | ⊙ |
| 2-7 | 2-14 | 30:70 | Styrene-acrylic resin | Black | 1 | 4 | 5 | ⊙ |
| 2-8 | 2-15 | 30:70 | Styrene-acrylic resin | Black | 1 | 5 | 5 | ⊙ |
| 2-9 | 2-16 | 30:70 | Styrene-acrylic resin | Black | 1 | 4 | 5 | ⊙ |
| 2-10 | 2-17 | 30:70 | Styrene-acrylic resin | Black | 1 | 4 | 5 | ⊙ |
| 2-11 | 2-18 | 30:70 | Styrene-acrylic resin | Black | 1 | 5 | 5 | ⊙ |
| 2-12 | 2-19 | 30:70 | Styrene-acrylic resin | Black | 1 | 5 | 5 | ⊙ |
| 2-13 | 2-20 | 30:70 | Styrene-acrylic resin | Black | 1 | 4 | 5 | ⊙ |
| 2-14 | 2-21 | 30:70 | Styrene-acrylic resin | Black | 1 | 5 | 5 | ⊙ |
| 2-15 | 2-22 | 30:70 | Styrene-acrylic resin | Black | 1 | 5 | 5 | ⊙ |
| 2-16 | 2-23 | 30:70 | Styrene-acrylic resin | Black | 1 | 4 | 5 | ⊙ |
| 2-17 | 2-24 | 30:70 | Styrene-acrylic resin | Black | 1 | 5 | 5 | ⊙ |
| 2-18 | 2-25 | 30:70 | Styrene-acrylic resin | Black | 1 | 5 | 5 | ⊙ |
| 2-19 | 2-26 | 30:70 | Styrene-acrylic resin | Black | 1 | 5 | 5 | ⊙ |
| 2-20 | 2-27 | 30:70 | Styrene-acrylic resin | Black | 1 | 4 | 5 | ⊙ |
| 2-21 | 2-28 | 30:70 | Styrene-acrylic resin | Black | 1 | 5 | 5 | ⊙ |
| 2-22 | 2-30 | 30:70 | Styrene-acrylic resin | Black | 1 | 4 | 5 | ⊙ |
| 2-23 | 2-32 | 30:70 | Styrene-acrylic resin | Black | 1 | 4 | 5 | ⊙ |
| 2-24 | 2-33 | 30:70 | Styrene-acrylic resin | Black | 1 | 3 | 4 | ⊙ |
| 2-25 | 2-35 | 30:70 | Styrene-acrylic resin | Black | 1 | 4 | 5 | ⊙ |
| 2-26 | 2-37 | 30:70 | Styrene-acrylic resin | Black | 1 | 5 | 5 | ⊙ |
| 2-27 | 2-38 | 30:70 | Styrene-acrylic resin | Black | 1 | 5 | 5 | ⊙ |
| 2-28 | 2-39 | 30:70 | Styrene-acrylic resin | Black | 1 | 4 | 5 | ⊙ |
| 2-29 | 2-41 | 30:70 | Styrene-acrylic resin | Black | 1 | 4 | 5 | ⊙ |
| 2-30 | 2-42 | 30:70 | Styrene-acrylic resin | Black | 1 | 4 | 5 | ⊙ |
| 2-31 | 2-44 | 30:70 | Styrene-acrylic resin | Black | 1 | 4 | 5 | ⊙ |
| 2-32 | 2-45 | 30:70 | Styrene-acrylic resin | Black | 1 | 4 | 5 | ⊙ |
| 2-33 | 2-46 | 30:70 | Styrene-acrylic resin | Black | 1 | 3 | 4 | ⊙ |
| 2-34 | 2-48 | 30:70 | Styrene-acrylic resin | Black | 1 | 3 | 4 | ⊙ |
| 2-35 | 2-50 | 30:70 | Styrene-acrylic resin | Black | 1 | 4 | 5 | ⊙ |
| 2-36 | 2-51 | 30:70 | Styrene-acrylic resin | Black | 1 | 3 | 4 | ⊙ |
| 2-37 | 2-52 | 30:70 | Styrene-acrylic resin | Black | 1 | 3 | 4 | ⊙ |
| 2-38 | 2-53 | 30:70 | Styrene-acrylic resin | Black | 1 | 3 | 4 | ⊙ |
| 2-39 | 2-54 | 30:70 | Styrene-acrylic resin | Black | 1 | 3 | 4 | ⊙ |
| 2-40 | 2-55 | 30:70 | Styrene-acrylic resin | Black | 1 | 3 | 4 | ⊙ |
| 2-41 | 2-56 | 30:70 | Styrene-acrylic resin | Black | 1 | 3 | 4 | ⊙ |
| 2-42 | 2-57 | 30:70 | Styrene-acrylic resin | Black | 1 | 3 | 4 | ⊙ |
| 2-43 | 2-59 | 30:70 | Styrene-acrylic resin | Black | 1 | 3 | 4 | ⊙ |
| 2-44 | 2-12 | 10:90 | Styrene-acrylic resin | Black | 1 | 4 | 5 | ⊙ |
| 2-45 | 2-12 | 50:50 | Styrene-acrylic resin | Black | 1 | 4 | 5 | ⊙ |
| 2-46 | 2-12 | 70:30 | Styrene-acrylic resin | Black | 1 | 4 | 5 | ⊙ |
| 2-47 | 2-12 | 90:10 | Styrene-acrylic resin | Black | 1 | 3 | 4 | ⊙ |
| 2-48 | 2-12 | 30:70 | Polyester resin | Black | 1 | 4 | 5 | ⊙ |
| 2-49 | 2-12 | 10:90 | Polyester resin | Black | 1 | 3 | 4 | ⊙ |
| 2-50 | 2-12 | 50:50 | Polyester resin | Black | 1 | 4 | 5 | ⊙ |
| 2-51 | 2-12 | 70:30 | Polyester resin | Black | 1 | 4 | 5 | ⊙ |
| 2-5 | 2-12 | 30:70 | Styrene-acrylic resin | Black | 2 | 6 | 6 | ⊙ |
| 2-5 | 2-12 | 30:70 | Styrene-acrylic resin | Black | 3 | 6 | 6 | ⊙ |
| Comparative Example 2-1 | Comparative Example 2-1 | 30:70 | Styrene-acrylic resin | Black | 1 | 1 | 1 | ⊙ |
| Comparative Example 2-2 | Comparative Example 2-2 | 30:70 | Styrene-acrylic resin | Black | 1 | 4 | 5 | X |

The "Compound" in Table 2-3 refers to a compound having an azomethine part represented by the General Formula (1). The number of a compound refers to the number of a compound having an azomethine part in Table 2-1 and Table 2-2. The "Compound: binder resin (mass ratio)" in Table 2-3 represents the compound having an azomethine part: binder resin (mass ratio) in the toner. However, with regard to Comparative Example 2-2, the term represents "Azobenzene compound:binder resin (mass ratio)".

As is obvious from Table 2-3, the toners 2-1 to 2-51 of Examples all exhibited high fixability and excellent color reproducibility. On the other hand, in the toner of Comparative Example 2-1 using a compound having an activation energy of lower than 60 kJ/mol, sufficient fixability induced by light irradiation cannot be obtained. Furthermore, in the toner of Comparative Example 2-2 using an azobenzene compound, fixability is satisfactory; however, color reproducibility is low. Since the light source of ultraviolet radiation and the conditions for ultraviolet irradiation used in the fixability test were constant throughout the Examples and Comparative Examples, in the toners of Examples, it can be said that the effects provided by the compound having an azomethine part, by which the toner is fluidized by being irradiated with light and reversibly non-fluidized and does not undergo noticeable coloration, are sufficiently exhibited compared to the toner of Comparative Examples.

When a comparison of the fixing apparatuses is made, it could be seen that rather than using the fixing apparatus of No. 1 in which the same toner 2-5 was used and irradiated with ultraviolet radiation under the same conditions while no pressing member was used, superior fixability is obtained by using the fixing apparatus of No. 2 in which the toner was pressed with a pressing member, and the fixing apparatus of No. 3 in which the toner was pressed while heated with a pressing member.

Although embodiments of the present invention have been described and illustrated in detail, it is clearly understood that the same is by way of illustration and example only and not limitation, the scope of the present invention should be interpreted by terms of the appended claims.

What is claimed is:

1. A compound represented by a following Chemical Formula 1:

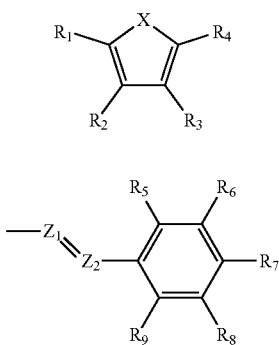

<Chemical Formula 1>

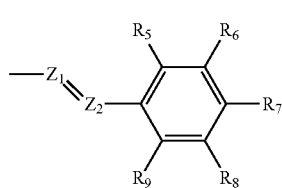

<Chemical Formula 2> wherein X represents $NR_{10}$ or S;
$Z_1$ represents CH and $Z_2$ represents N;
$R_1$ represents a hydrogen atom, an alkyl group, an alkoxy group, an acyl group having 2 to 19 carbon atoms, an alkoxycarbonyl group, a cyano group, or a hydroxy group;
$R_2$ represents a hydrogen atom, a halogen atom, an alkyl group, an alkoxy group, an acyl group having 2 to 19 carbon atoms, an alkoxycarbonyl group, a cyano group, a nitro group, or a hydroxy group;
$R_3$ represents a group represented by Chemical Formula 2, a hydrogen atom, a halogen atom, an alkyl group, an alkoxy group, an acyl group having 2 to 19 carbon atoms, an alkoxycarbonyl group, a cyano group, a nitro group, dialkylamino group, or a hydroxy group;
$R_4$ represents a hydrogen atom or the group represented by Chemical Formula 2;
either of $R_3$ and $R_4$ represents the group represented by Chemical Formula 2;
$R_{10}$ represents a hydrogen atom, a halogen atom, an alkyl group, an alkoxycarbonyl group, or a hydroxy group;
$R_5$, $R_6$, $R_8$, and $R_9$ each independently represent a hydrogen atom, a halogen atom, an alkyl group, an alkoxy group, an acyl group having 2 to 19 carbon atoms, an alkoxycarbonyl group, a cyano group, a nitro group, or a hydroxy group;
$R_7$ represents an alkoxy group having 6 to 12 carbon atoms, an acyl group having 5 to 13 carbon atoms, or an alkoxycarbonyl group having 5 to 13 carbon atoms; and
when $R_1$ represents the hydrogen atom, at least one of $R_2$ to $R_4$ in the Chemical Formula 1 represents a halogen atom, a cyano group, a nitro group, a hydroxy group, an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms, and/or $R_{10}$ represents a halogen atom, a hydroxy group, an alkyl group having 1 to 18 carbon atoms, or an alkoxycarbonyl group having 2 to 19 carbon atoms.

2. The compound according to claim 1, wherein at least one of $R_5$, $R_6$, $R_8$, and $R_9$ represents an alkyl group having 1 to 4 carbon atoms which may be branched, an alkoxy group having 1 to 4 carbon atoms which may be branched, or a halogen atom.

3. A toner comprising a compound represented by a following Chemical Formula 1:

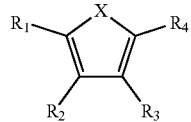

<Chemical Formula 1>

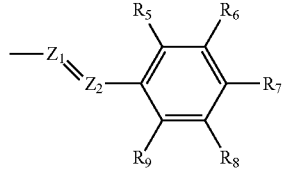

<Chemical Formula 2> wherein X represents $NR_{10}$ or S;
$Z_1$ represents CH and $Z_2$ represents N;
$R_1$ represents a hydrogen atom, an alkyl group, an alkoxy group, an acyl group having 2 to 19 carbon atoms, an alkoxycarbonyl group, a cyano group, or a hydroxy group;
$R_2$ represents a hydrogen atom, a halogen atom, an alkyl group, an alkoxy group, an acyl group having 2 to 19 carbon atoms, an alkoxycarbonyl group, a cyano group, a nitro group, or a hydroxy group;
$R_3$ represents a group represented by Chemical Formula 2, a hydrogen atom, a halogen atom, an alkyl group, an alkoxy group, an acyl group having 2 to 19 carbon atoms, an alkoxycarbonyl group, a cyano group, a nitro group, dialkylamino group, or a hydroxy group;
$R_4$ represents a hydrogen atom or the group represented by Chemical Formula 2;
either of $R_3$ and $R_4$ represents the group represented by Chemical Formula 2;
$R_{10}$ represents a hydrogen atom, a halogen atom, an alkyl group, an alkoxycarbonyl group, or a hydroxy group;

$R_5$, $R_6$, $R_8$, and $R_9$ each independently represent a hydrogen atom, a halogen atom, an alkyl group, an alkoxy group, an acyl group having 2 to 19 carbon atoms, an alkoxycarbonyl group, a cyano group, a nitro group, or a hydroxy group;

$R_7$ represents an alkoxy group having 6 to 12 carbon atoms, an acyl group having 5 to 13 carbon atoms, or an alkoxycarbonyl group having 5 to 13 carbon atoms; and when $R_1$ represents the hydrogen atom, at least one of $R_2$ to $R_4$ in the Chemical Formula 1 represents a halogen atom, a cyano group, a nitro group, a hydroxy group, an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms, and/or $R_{10}$ represents a halogen atom, a hydroxy group, an alkyl group having 1 to 18 carbon atoms, or an alkoxycarbonyl group having 2 to 19 carbon atoms.

4. The toner according to claim 3, further comprising a binder resin.

5. The toner according to claim 4, wherein the binder resin includes a styrene-acrylic resin, a polyester resin, or a combination thereof.

6. The toner according to claim 3, further comprising a colorant.

7. The toner according to claim 3, further comprising a release agent.

8. A photosensitive adhesive comprising a compound represented by a following Chemical Formula 1:

<Chemical Formula 1>

<Chemical Formula 2>

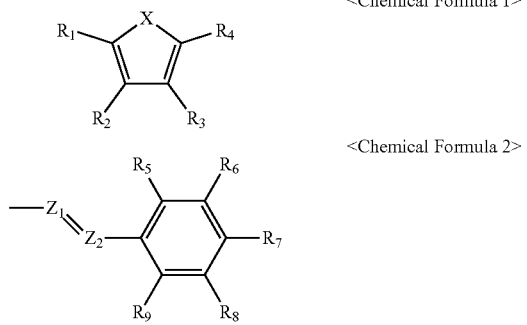

wherein X represents $NR_{10}$ or S;

$Z_1$ represents CH and $Z_2$ represents N;

$R_1$ represents a hydrogen atom, an alkyl group, an alkoxy group, an acyl group having 2 to 19 carbon atoms, an alkoxycarbonyl group, a cyano group, or a hydroxy group;

$R_2$ represents a hydrogen atom, a halogen atom, an alkyl group, an alkoxy group, an acyl group having 2 to 19 carbon atoms, an alkoxycarbonyl group, a cyano group, a nitro group, or a hydroxy group;

$R_3$ represents a group represented by Chemical Formula 2, a hydrogen atom, a halogen atom, an alkyl group, an alkoxy group, an acyl group having 2 to 19 carbon atoms, an alkoxycarbonyl group, a cyano group, a nitro group, dialkylamino group, or a hydroxy group;

$R_4$ represents a hydrogen atom or the group represented by Chemical Formula 2;

either of $R_3$ and $R_4$ represents the group represented by Chemical Formula 2;

$R_{10}$ represents a hydrogen atom, a halogen atom, an alkyl group, an alkoxycarbonyl group, or a hydroxy group;

$R_5$, $R_6$, $R_8$, and $R_9$ each independently represent a hydrogen atom, a halogen atom, an alkyl group, an alkoxy group, an acyl group having 2 to 19 carbon atoms, an alkoxycarbonyl group, a cyano group, a nitro group, or a hydroxy group;

$R_7$ represents an alkoxy group having 6 to 12 carbon atoms, an acyl group having 5 to 13 carbon atoms, or an alkoxycarbonyl group having 5 to 13 carbon atoms; and when $R_1$ represents the hydrogen atom, at least one of $R_2$ to $R_4$ in the Chemical Formula 1 represents a halogen atom, a cyano group, a nitro group, a hydroxy group, an alkyl group having 1 to 18 carbon atoms, an alkoxy group having 1 to 18 carbon atoms, an acyl group having 2 to 19 carbon atoms, or an alkoxycarbonyl group having 2 to 19 carbon atoms, and/or $R_{10}$ represents a halogen atom, a hydroxy group, an alkyl group having 1 to 18 carbon atoms, or an alkoxycarbonyl group having 2 to 19 carbon atoms.

9. The compound according to claim 1, wherein $R_4$ represents the group represented by Chemical Formula 2.

10. The compound according to claim 1, wherein $R_1$ represents an alkyl group, and $R_4$ represents the group represented by Chemical Formula 2.

* * * * *